(12) United States Patent
Sperl et al.

(10) Patent No.: US 12,209,073 B2
(45) Date of Patent: Jan. 28, 2025

(54) POLYMORPHS OF A DIHYDROOROTATE DEHYDROGENASE (DHOD) INHIBITOR

(71) Applicant: KIORA PHARMACEUTICALS GmbH, Vienna (AT)

(72) Inventors: Stefan Sperl, Vienna (AT); Lisa Plasser, Vienna (AT); Osama Suleiman, Cambridge (GB); Christopher Daniel Scott, Cambridge (GB); Susana Del Rio Gancedo, Cambridge (GB); Joseph Stephen Harris, Cambridge (GB)

(73) Assignee: Kiora Pharmaceuticals GmbH, Vienna (AT)

( * ) Notice: Subject to any disclaimer, the term of this patent is extended or adjusted under 35 U.S.C. 154(b) by 0 days.

(21) Appl. No.: 18/172,656

(22) Filed: Feb. 22, 2023

(65) Prior Publication Data

US 2023/0286938 A1    Sep. 14, 2023

Related U.S. Application Data

(60) Provisional application No. 63/318,281, filed on Mar. 9, 2022.

(51) Int. Cl.
   *C07D 333/02*    (2006.01)
(52) U.S. Cl.
   CPC ........ *C07D 333/02* (2013.01); *C07B 2200/13* (2013.01)

(58) Field of Classification Search
   CPC .. C07D 333/02; C07D 333/38; C07D 409/12; C07B 2200/13
   See application file for complete search history.

(56) References Cited

U.S. PATENT DOCUMENTS

| | | |
|---|---|---|
| 7,365,094 B2 | 4/2008 | Leban et al. |
| 8,354,433 B2 | 1/2013 | Vitt et al. |
| 9,795,590 B2 | 10/2017 | Strobl |
| 2017/0071904 A1 | 3/2017 | Sperl et al. |
| 2019/0025313 A1 | 1/2019 | Si et al. |

FOREIGN PATENT DOCUMENTS

| | | | | |
|---|---|---|---|---|
| WO | WO-2004056797 A1 | * | 7/2004 | ............. A61P 11/02 |
| WO | WO-2022214691 A1 | * | 10/2022 | |

OTHER PUBLICATIONS

Substance Detail for CAS Registry No. 717142-73-9. Accessed Dec. 4, 2023 (Year: 2023).*

(Continued)

*Primary Examiner* — Clinton A Brooks
*Assistant Examiner* — Kyle Nottingham
(74) *Attorney, Agent, or Firm* — Knobbe, Martens, Olson & Bear LLP

(57) ABSTRACT

The present disclosure provides polymorphs of 3-(2,3,5,6-tetrafluoro-3'-trifluoromethoxy-biphenyl-4-ylcarbamoyl)-thiophene-2-carboxylic acid, and methods of making such polymorphs. The present disclosure further provides pharmaceutical compositions and kits comprising polymorphs of the invention, and methods of treating, preventing, or ameliorating a disease or condition comprising administering a polymorph of the invention.

20 Claims, 50 Drawing Sheets

(56) References Cited

OTHER PUBLICATIONS

Marschall, Manfred, et al. "Assessment of Drug Candidates for Broad-Spectrum Antiviral Therapy Targeting Cellular Pyrimidine Biosynthesis." Antiviral Research, vol. 100, No. 3, Dec. 2013, pp. 640-648. ScienceDirect, https://doi.org/10.1016/j.antiviral.2013.10.003. (Year: 2013).*

Supporting information for Marschall, Manfred, et al. "Assessment of Drug Candidates for Broad-Spectrum Antiviral Therapy Targeting Cellular Pyrimidine Biosynthesis." Antiviral Research, vol. 100, No. 3, Dec. 2013, pp. 640-648. ScienceDirect, https://doi.org/10.1016/j.antiviral.2013.10.003. (Year: 2013).*

International Search Report and Written Opinion of PCT/US2023/062994, mailed May 15, 2023.

* cited by examiner

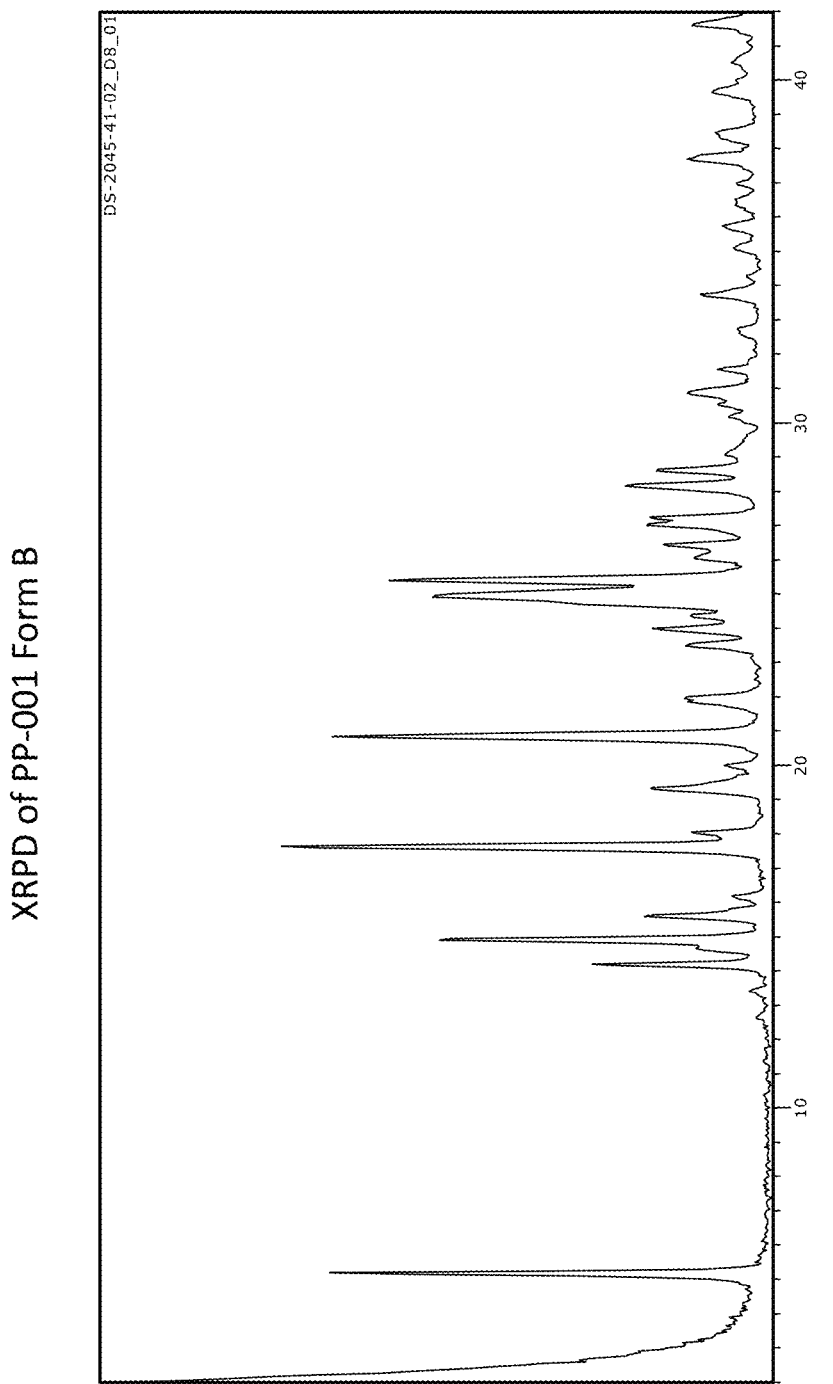

Solubility Assessment of PP-001 Form A, part 1

| Sample ID | Solvent | Vol 5 | 10 | 20 | 30 | 50 | 80 | Obs. | Obs. At 50°C | Treatment |
|---|---|---|---|---|---|---|---|---|---|---|
| DS-2045-08-01 | n-Heptane | X | X | X | X | X | | Suspension | Suspension | Maturation Cycling (RT/50°C) |
| DS-2045-08-02 | Diethyl ether | X | X | X | X | X | | Suspension | Not Run | Maturation at RT |
| DS-2045-08-03 | Propyl acetate | X | X | X | X | P | √ | Clear Solution | N/A | Cool to 5°C |
| DS-2045-08-04 | Ethyl acetate | X | X | X | X | √ | | Clear Solution | N/A | Cool to 5°C |
| DS-2045-08-05 | Isopropyl acetate | X | X | X | X | P | √ | Clear Solution | N/A | Cool to 5°C |
| DS-2045-08-06 | MIBK | X | X | X | P | √ | | Clear Solution | N/A | Cool to 5°C |
| DS-2045-08-07 | 2-Propanol | X | X | X | X | P | P* | Opaque Solution | Clear Solution | Cool to 5°C |
| DS-2045-08-08 | MEK | X | X | √ | X | | | Clear Solution | N/A | Cool to 5°C |
| DS-2045-08-09 | 1-Propanol | X | X | √ | X | P | P* | Opaque Solution | Clear Solution | Cool to 5°C |
| DS-2045-08-10 | Acetone | X | X | X | X | | | Clear Solution | N/A | Cool to 5°C |
| DS-2045-08-11 | Ethanol | X | X | X | X | √ | | Clear Solution | N/A | Cool to 5°C |
| DS-2045-08-12 | Dimethyl sulfoxide | √ | | | | | | Clear Solution | N/A | Antisolvent (H2O) |
| DS-2045-08-13 | Acetonitrile | X | X | X | X | X | | Suspension | Clear Solution | Cool to 5°C |
| DS-2045-08-14 | tert-Butylmethyl ether | X | X | X | X | P | √ | Clear Solution | N/A | Cool to 5°C |

Key: X = suspension, √ = Clear solution, P = Partial Dissolution, P*: Clear solution, but some particulates noted

Fig. 3A

Solubility Assessment of PP-001 Form A, part 2

| Sample ID | Solvent | Vol 5 | Vol 10 | Vol 20 | Vol 30 | Vol 50 | Vol 80 | Obs. | Obs. At 50°C | Treatment |
|---|---|---|---|---|---|---|---|---|---|---|
| DS-2045-08-15 | 1,4-Dioxane | X | | - | - | - | - | Clear Solution | N/A | Evap at RT |
| DS-2045-08-16 | Toluene | X | X | X | X | X | X | Suspension | Suspension | Maturation cycling (RT/50°C) |
| DS-2045-08-17 | Chloroform | X | X | X | X | X | X | Suspension | Suspension | Maturation cycling (RT/50°C) |
| DS-2045-08-18 | Tetrahydrofuran | | | - | - | - | - | Solution | N/A | Cool to 5°C |
| DS-2045-08-19 | Methanol | X | - | X | X | P | Y | Clear Solution | N/A | Cool to 5°C |
| DS-2045-08-20 | Water | X | X | X | X | X | X | Suspension | Suspension | Maturation cycling (RT/50°C) |
| DS-2045-08-21 | Methanol: water (3%) | X | X | X | X | X | P* | Clear Solution, small particulates | Clear Solution | Cool to 5°C |
| DS-2045-08-22 | Methanol: water (5%) | X | X | X | X | X | X | Suspension | Clear Solution | Cool to 5°C |
| DS-2045-08-23 | Ethanol: water (5%) | X | X | X | X | X | P* | Clear Solution, small particulates | Clear Solution | Cool to 5°C |
| DS-2045-08-24 | IPA: Water (5%) | X | X | X | X | X | P* | Clear Solution, small particulates | Clear Solution | Cool to 5°C |
| DS-2045-08-25 | Acetone: Water (5%) | X | √ | - | - | - | - | Clear Solution | N/A | Cool to 5°C |
| DS-2045-08-26 | Acetone: Water (10%) | X | √ | - | - | - | - | Clear Solution | N/A | Cool to 5°C |
| DS-2045-08-27 | IPA: Water (25%) | X | X | X | X | X | X | Suspension | Clear Solution | Cool to 5°C |
| DS-2045-08-28 | THF: Water (10%) | √ | - | - | - | - | - | Clear Solution | N/A | Cool to 5°C |

Key: X = suspension, √ = Clear solution, p = Partial Dissolution, p* = Clear solution, but some particulates noted

Fig. 3B

Results from the polymorph screen of PP-001, part 1

| Sample ID | Solvent | Obs. After Treatment | Further Treatment | Obs. After Treatment | XRPD (W/EMP) | XRPD (D/EMP) |
|---|---|---|---|---|---|---|
| DS-2045-08-01 | n-Heptane | Suspension | N/A | N/A | Form A | N/A |
| DS-2045-08-02 | Diethyl ether | Suspension | N/A | N/A | Form A | N/A |
| DS-2045-08-03 | Propyl acetate | Solution | Evap at RT | Crystalline powder | N/A | Form A |
| DS-2045-08-04 | Ethyl acetate | Solution | Evap at RT | Rectangular single crystals (small) | N/A | Form A |
| DS-2045-08-05 | Isopropyl acetate | Solution | Evap at RT | Crystalline powder | N/A | Form B |
| DS-2045-08-06 | MIBK | Solution | Evap at RT | Crystalline powder | N/A | Form A |
| DS-2045-08-07 | 2-Propanol | Solution | Evap at RT | Rectangular single crystals (small) | N/A | Form A |
| DS-2045-08-08 | MEK | Solution | Evap at RT | Crystalline Needles + Dendrites Structures | N/A | Form A |
| DS-2045-08-09 | 1-Propanol | Solution | Evap at RT | Rectangular single crystals | N/A | Form A |
| DS-2045-08-10 | Acetone | Suspension | Hold at 5°C | Thin Suspension | Insufficient material | N/A |
| DS-2045-08-11 | Ethanol | Solution | Evap at RT | Crystalline powder (needle-like) | N/A | Form A |
| DS-2045-08-12 | Dimethyl sulfoxide | Thin Suspension | N/A | N/A | Amorphous | N/A |
| DS-2045-08-13 | Acetonitrile | Suspension | Hold at 5°C | Suspension | Form A | N/A |
| DS-2045-08-14 | tert-Butylmethyl ether | Solution | Evap at RT | Clumped powder + dendrite structures | N/A | Form B |

Key: Evap = Slow evaporation, W = Wet, D = Dry

Fig. 4A

Results from the polymorph screen of PP-001, part 2

| Sample ID | Solvent | Obs. After Treatment | Further Treatment | Obs. After Treatment | XRPD (W/EMP) | XRPD (D/EMP) |
|---|---|---|---|---|---|---|
| DS-2045-08-15 | 1,4-Dioxane | N/A | N/A | Clumped powder | Form B | Form B |
| DS-2045-08-16 | Toluene | Suspension | N/A | N/A | Form A | N/A |
| DS-2045-08-17 | Chloroform | Suspension | N/A | N/A | Form A | N/A |
| DS-2045-08-18 | Tetrahydrofuran | Solution | Evap at RT | Clumped powder | N/A | Form B |
| DS-2045-08-19 | Methanol | Solution | Evap at RT | Rectangular single crystals (large) | N/a | Form A |
| DS-2045-08-20 | Water | Suspension | N/A | N/A | Form A | N/A |
| DS-2045-08-21 | Methanol: water (3%) | Solution* | Hold at 5°C | Thin Suspension | Insufficient material | N/A |
| DS-2045-08-22 | Methanol: water (5%) | Suspension | Hold at 5°C | Suspension | Form A | N/A |
| DS-2045-08-23 | Ethanol: water (5%) | Solution | Evap at RT | Rectangular single crystals (small) | N/A | Form A |
| DS-2045-08-24 | IPA: Water (5%) | Solution | Evap at RT | Rectangular single crystals (large) | N/A | Form A |
| DS-2045-08-25 | Acetone: Water (5%) | Solution | Evap at RT | Crystalline powder + dendrite structures | N/A | Form A |
| DS-2045-08-26 | Acetone: Water (10%) | Solution | Evap at RT | Crystalline powder | N/A | Form A + Form B |
| DS-2045-08-27 | IPA: Water (25%) | Suspension | Hold at 5°C | Suspension | N/A | N/A |
| DS-2045-08-28 | THF: Water (10%) | Solution | Evap at RT | Clumped powder | N/A | Form B |

Key: Evap = Slow evaporation, W = Wet, D = Dry

Fig. 4B

Summary of result of solubility screen prior to lyophilization

| Sample ID | Solvent | Vol 5 | 10 | 20 | 30 | 40 | 60 | Obs. | Treatment | Obs. After Treatment | XRPD (Wet) | XRPD (Dry) |
|---|---|---|---|---|---|---|---|---|---|---|---|---|
| DS-2045-09-01 | THF:Water (70:30) | P | P | ✓ | - | - | - | Clear Solution | Freeze Dry | White Powder | N/A | Amorphous |
| DS-2045-09-02 | ACN:Water (1:1) | X | X | X | X | X | X | Suspension | Maturation Cycling (RT/50°C) | Suspension | Form A | N/A |
| DS-2045-09-03 | t-BuOH | X | X | P | P | P | P | Opaque Solution | Maturation Cycling (RT/50°C) | Solution | N/A | Form B* |
| DS-2045-09-04 | DCM | X | X | X | X | X | X | Suspension | Maturation at RT | Suspension | Form A | N/A |
| DS-2045-09-05 | 1,4-Dioxane | - | P | P | ✓ | - | - | Clear Solution | Freeze Dry | White Powder | N/A | Amorphous |
| DS-2045-09-06 | t-BuOH/Water (1:1) | X | X | X | X | X | X | Suspension | Maturation Cycling (RT/50°C) | Suspension | Form A | N/A |

Key: X = suspension, ✓ = Clear solution, P = Partial Dissolution
*Solution subjected to slow evaporation at RT until dry

Fig. 5

Observations and results from the maturation of amorphous material at 5 °C, part 1

| Sample ID | Solvent | Obs. After Treatment | Further Treatment | Obs. After Treatment | XRPD (W) Pattern 3 (WD) | XRPD (D) Pattern 3 |
|---|---|---|---|---|---|---|
| DS-2045-21-01 | n-Heptane | Swollen Solid/Gel | Additional Maturation (1 Day) | Swollen Solid/Gel | Pattern 3 | Pattern 3 |
| DS-2045-21-02 | Diethyl ether | Suspension | N/A | N/A | Form B | N/A |
| DS-2045-21-03 | Propyl acetate | Suspension | N/A | N/A | Form B | N/A |
| DS-2045-21-04 | Ethyl acetate | Suspension | N/A | N/A | Form A | N/A |
| DS-2045-21-05 | Isopropyl acetate | Suspension | N/A | N/A | Form B | N/A |
| DS-2045-21-06 | MIBK | Suspension | N/A | N/A | Form A | N/A |
| DS-2045-21-07 | 2-Propanol | Suspension | N/A | N/A | Form A | N/A |
| DS-2045-21-08 | MEK | Suspension | N/A | N/A | Form A | N/A |
| DS-2045-21-09 | 1-Propanol | Suspension | N/A | N/A | Form A | N/A |
| DS-2045-21-10 | Acetone | Suspension | N/A | N/A | Form A | N/A |
| DS-2045-21-11 | Ethanol | Suspension | N/A | N/A | Form A | N/A |
| DS-2045-21-12 | DMSO | Froze | Addition of 1500 ul of MeCN (10 equiv.) | Solution | No further work | N/A |
| DS-2045-21-13 | Acetonitrile | Suspension | N/A | N/A | Form A | N/A |
| DS-2045-21-14 | TBME | Suspension | N/A | N/A | Form B | N/A |

Key: W = wet, D = dry, WD = weak diffraction

Fig. 6A

Observations and results from the maturation of amorphous material at 5 C, part 2

| Sample ID | Solvent | Obs. After Treatment | Further Treatment | Obs. After Treatment | XRPD (W) |
|---|---|---|---|---|---|
| DS-2045-21-15 | 1,4-Dioxane | Partially Froze / Slurry | N/A | N/A | Form B |
| DS-2045-21-16 | Toluene | Suspension | N/A | N/A | Form B |
| DS-2045-21-17 | Chloroform | Suspension | N/A | N/A | Form B |
| DS-2045-21-18 | THF / Heptane (1:1) | Suspension | N/A | N/A | Form B |
| DS-2045-21-19 | Methanol | Suspension | N/A | N/A | Form A |
| DS-2045-21-20 | Water | Suspension | N/A | N/A | Form A (WD) |
| DS-2045-21-21 | Methanol: water (3%) | Suspension | N/A | N/A | Form A |
| DS-2045-21-22 | Methanol: water (5%) | Suspension | N/A | N/A | Form A |
| DS-2045-21-23 | Ethanol: water (5%) | Suspension | N/A | N/A | Form B |
| DS-2045-21-24 | IPA: Water (5%) | Suspension | N/A | N/A | Form A |
| DS-2045-21-25 | Acetone: Water (5%) | Suspension | N/A | N/A | Form A |
| DS-2045-21-26 | Acetone: Water (10%) | Suspension | N/A | N/A | Form A |
| DS-2045-21-27 | IPA:Water (25%) | Suspension | N/A | N/A | Form B |
| DS-2045-21-28 | THF: Water (50%) | Clear Solution + Gummy Solid | N/A | N/A | Form A |

Key: W = wet, WD = weak diffraction

Fig. 6B

Observations and results from the maturation cycling of amorphous material, part 1

| Sample ID | Solvent | Obs. After Treatment | Further Treatment | XRPD (W) |
|---|---|---|---|---|
| DS-2045-24-01 | n-Heptane | Swollen Solid/Gel | N/A | Form B |
| DS-2045-24-02 | Diethyl ether | Not Run | N/A | N/A |
| DS-2045-24-03 | Propyl acetate | Suspension | N/A | Form A |
| DS-2045-24-04 | Ethyl acetate | Clear solution + solid on vial walls | N/A | Form A |
| DS-2045-24-05 | Isopropyl acetate | Suspension | N/A | Form A |
| DS-2045-24-06 | MIBK | Suspension | N/A | Form A |
| DS-2045-24-07 | 2-Propanol | Suspension | N/A | Form A |
| DS-2045-24-08 | MEK | Suspension | N/A | Form A |
| DS-2045-24-09 | 1-Propanol | Suspension | N/A | Form A |
| DS-2045-24-10 | Acetone | Clear solution + solid on vial walls | N/A | Form A |
| DS-2045-24-11 | Ethanol | Thin Suspension | N/A | Form A |
| DS-2045-24-12 | DMSO / Water (1:1) | Suspension | N/A | Form A (WD) |
| DS-2045-24-13 | Acetonitrile | Suspension | N/A | Form A |
| DS-2045-24-14 | TBME | Suspension | N/A | Form B |

Key: W = wet, WD = weak diffraction

Fig. 8A

Observations and results from the maturation cycling of amorphous material, part 2

| Sample ID | Solvent | Obs. After Treatment | Further Treatment | XRPD (W) |
|---|---|---|---|---|
| DS-2045-24-15 | 1,4-Dioxane / Heptane (1:1) | Suspension | N/A | Form A |
| DS-2045-24-16 | Toluene | Suspension | N/A | Form B |
| DS-2045-24-17 | Chloroform | Suspension | N/A | Form B |
| DS-2045-24-18 | THF / Heptane (1:1) | Suspension | N/A | Form A |
| DS-2045-24-19 | Methanol | Suspension | N/A | Form A |
| DS-2045-24-20 | Water | Suspension | N/A | Form A |
| DS-2045-24-21 | Methanol: water (3%) | Suspension | N/A | Form A |
| DS-2045-24-22 | Methanol: water (5%) | Suspension | N/A | Form A |
| DS-2045-24-23 | Ethanol: water (5%) | Suspension | N/A | Form A |
| DS-2045-24-24 | IPA: Water (5%) | Suspension | N/A | Form B |
| DS-2045-24-25 | Acetone: Water (5%) | Solution | 150 ul of water added at 50 °C | Form B |
| DS-2045-24-26 | Acetone: Water (10%) | Thin Suspension | N/A | Form A |
| DS-2045-24-27 | IPA:Water (25%) | Suspension | N/A | Form A |
| DS-2045-24-28 | THF: Water (50%) | Suspension | N/A | Form A |

Key: W = wet

Fig. 8B

Observations and results from the maturation of amorphous material at 50 °C, part 1

| Sample ID | Solvent | Obs. After Treatment | XRPD (W/EMP) |
|---|---|---|---|
| DS-2045-31-01 | n-Heptane | Swollen Solid/Gel | Form B |
| DS-2045-31-02 | Diethyl ether | Not Run | N/A |
| DS-2045-31-03 | Propyl acetate | Solid on vial walls + solution | Form A |
| DS-2045-31-04 | Ethyl acetate | Solid on vial walls + solution | Form A |
| DS-2045-31-05 | Isopropyl acetate | Solid on vial walls + solution | Form B to Form A* |
| DS-2045-31-06 | MIBK | Solid on vial walls + solution | Form A |
| DS-2045-31-07 | 2-Propanol | Suspension | Form A |
| DS-2045-31-08 | MEK | Solid on vial walls + solution | Form A |
| DS-2045-31-09 | 1-Propanol | Solid on vial walls + solution | Form A |
| DS-2045-31-10 | Acetone | Solid on vial walls + solution | Form A |
| DS-2045-31-11 | Ethanol | Solid on vial walls + solution | Form A |
| DS-2045-31-12 | DMSO / Water (1:1) | Suspension | Form A |
| DS-2045-31-13 | Acetonitrile | Suspension | Form A |
| DS-2045-31-14 | TBME | Solid on vial walls + solution | Form B |

Key: W = wet
* = *Isopropyl acetate sample transitioned to Form A between or on isolation

Fig. 9A

Observations and results from the maturation of amorphous material at 50 °C, part 2

| Sample ID | Solvent | Treatment | Obs. After Treatment | XRPD (A/EMP) | Further Treatment | XRPD (W/EMP) |
|---|---|---|---|---|---|---|
| DS-2045-31-15 | 1,4-Dioxane / Heptane (1:1) | Maturation (50°C) | Suspension | N/A | N/A | Form A |
| DS-2045-31-16 | Toluene | Maturation (50°C) | Suspension | N/A | N/A | Form B |
| DS-2045-31-17 | Chloroform | Maturation (50°C) | Suspension | N/A | N/A | Form A |
| DS-2045-31-18 | THF / Heptane (1:1) | Maturation (50°C) | Suspension | N/A | N/A | Form A |
| DS-2045-31-19 | Methanol | Maturation (50°C) | Solid on vial walls + solution | N/A | N/A | Form A |
| DS-2045-31-20 | Water | Maturation (50°C) | Suspension | N/A | N/A | Form A |
| DS-2045-31-21 | Methanol: water (3%) | Maturation (50°C) | Suspension | N/A | N/A | Form A |
| DS-2045-31-22 | Methanol: water (5%) | Maturation (50°C) | Suspension | N/A | N/A | Form A |
| DS-2045-31-23 | Ethanol: water (5%) | Maturation (50°C) | Suspension | N/A | N/A | Form A |
| DS-2045-31-24 | IPA: Water (5%) | Maturation (50°C) | Solid on vial walls + solution | N/A | N/A | Form A |
| DS-2045-31-25 | Acetone: Water (5%) | Antisolvent Addition* (50°C) | Suspension | Form B | Maturation (50°C) | Form A |
| DS-2045-31-26 | Acetone: Water (10%) | Maturation (50°C) | Solution | N/A | 450µl of ACN added at RT | Form A |
| DS-2045-31-27 | IPA:Water (13.5) | Maturation (50°C) | Suspension | N/A | N/A | Form A |
| DS-2045-31-28 | THF: Water (50%) | Maturation (50°C) | Suspension | N/A | N/A | Form A |

Key: A = aliquot, W = wet
* = 150 µl of water added

Fig. 9B

Observations and results from the antisolvent addition polymorph screen

| Sample ID | Solvent (S)/Antisolvent (A) | Temp | Final Ratio (S:A) | Obs. | Aliquot 1 (1 hour) | Aliquot 2 (24 hours) | XRPD (Isolated) |
|---|---|---|---|---|---|---|---|
| DS-2045-32-01 | 1,4-Dioxane / Water | RT | 1:1 | Suspension | Form B | Form A | N/A |
| DS-2045-32-02 | IPA / Water | 50°C | 1:2 | Suspension | WD | N/A | Form B |
| DS-2045-32-03 | Acetone / Water | RT | 1:1 | Suspension | Form B | Form A (WD) | Form A |
| DS-2045-32-04 | THF / Water | RT | 1:2 | Suspension | Form B | Form A | Form A |
| DS-2045-32-05 | MeOH / Water | 30°C | 1:3 | Suspension | WD | Form A | Form A |
| DS-2045-32-06 | Ethyl Acetate / Heptane | RT | 1:3 | Suspension | WD | WD | Form B |
| DS-2045-32-07 | MEK / Heptane | RT | 1:3 | Suspension | WD | Form A (WD) | Form A |
| DS-2045-32-08 | Acetone / Heptane | RT | 1:3 | Suspension | WD | Form A (WD) | Form B |
| DS-2045-32-09 | THF / Heptane | RT | 1:1 | Suspension | Form B | Form B | Form B |
| DS-2045-32-10 | IPA / Heptane | 50°C | 1:5 | Solution* | N/A | N/A | Form B |
| DS-2045-32-11 | Ethyl Acetate / Toluene | RT | 1:5 | Solution* | N/A | N/A | Form B |
| DS-2045-32-12 | MEK / Toluene | RT | 1:5 | Solution* | N/A | N/A | Form B |
| DS-2045-32-13 | Acetone / Toluene | RT | 1:5 | Solution* | N/A | N/A | Form B |
| DS-2045-32-14 | THF / Toluene | RT | 1:5 | Solution* | N/A | N/A | Form B |
| DS-2045-32-15 | MeOH / Toluene | 30°C | 1:5 | Solution* | N/A | N/A | Form B |

Key: WD = weak diffraction
\* = Solutions subjected to slow evaporation at RT

Fig. 10

B. Scanning Electron Microscopy (SEM) of PP-001 Form A

A. Polarized Light Microscopy (PLM) of PP-001 Form A

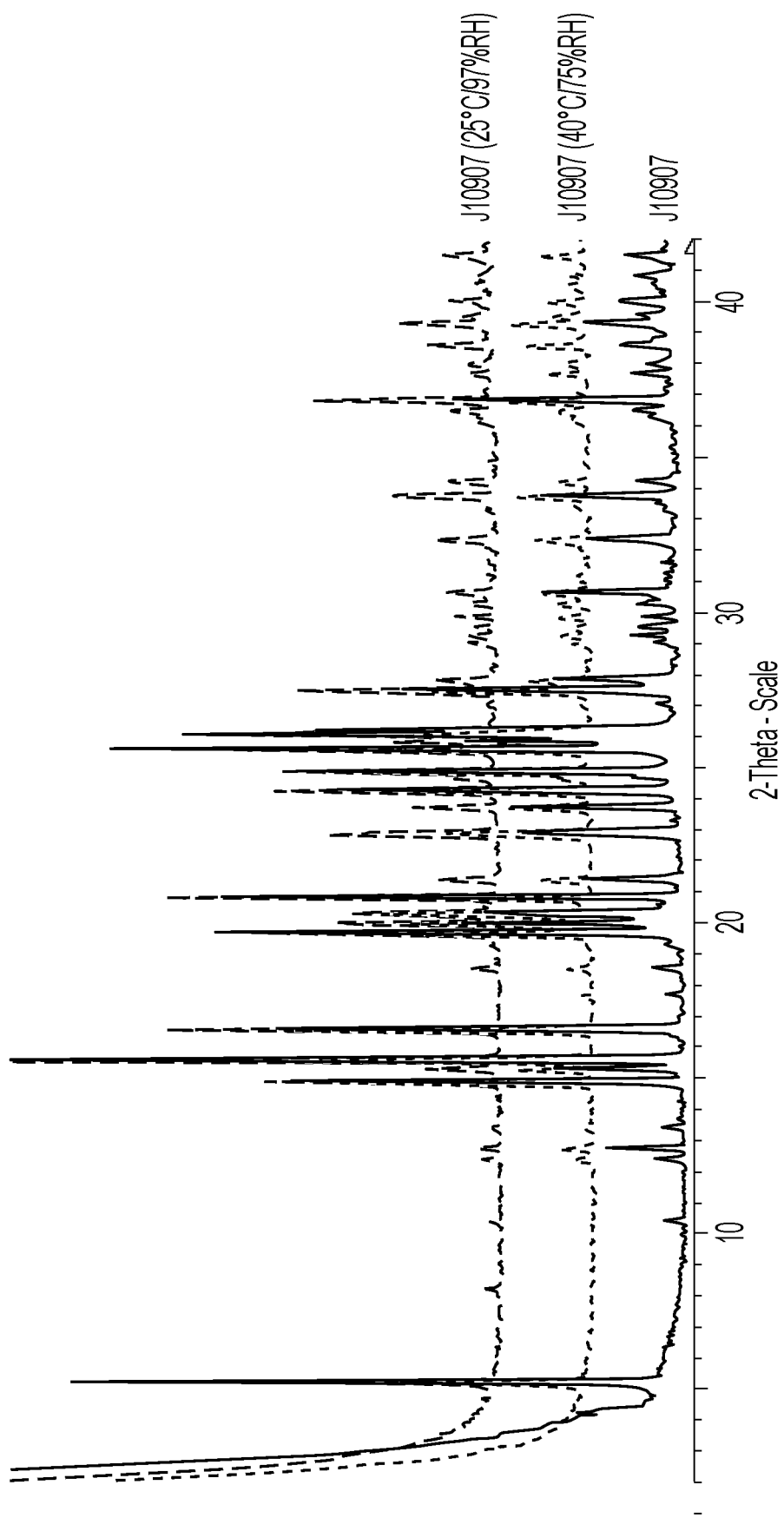

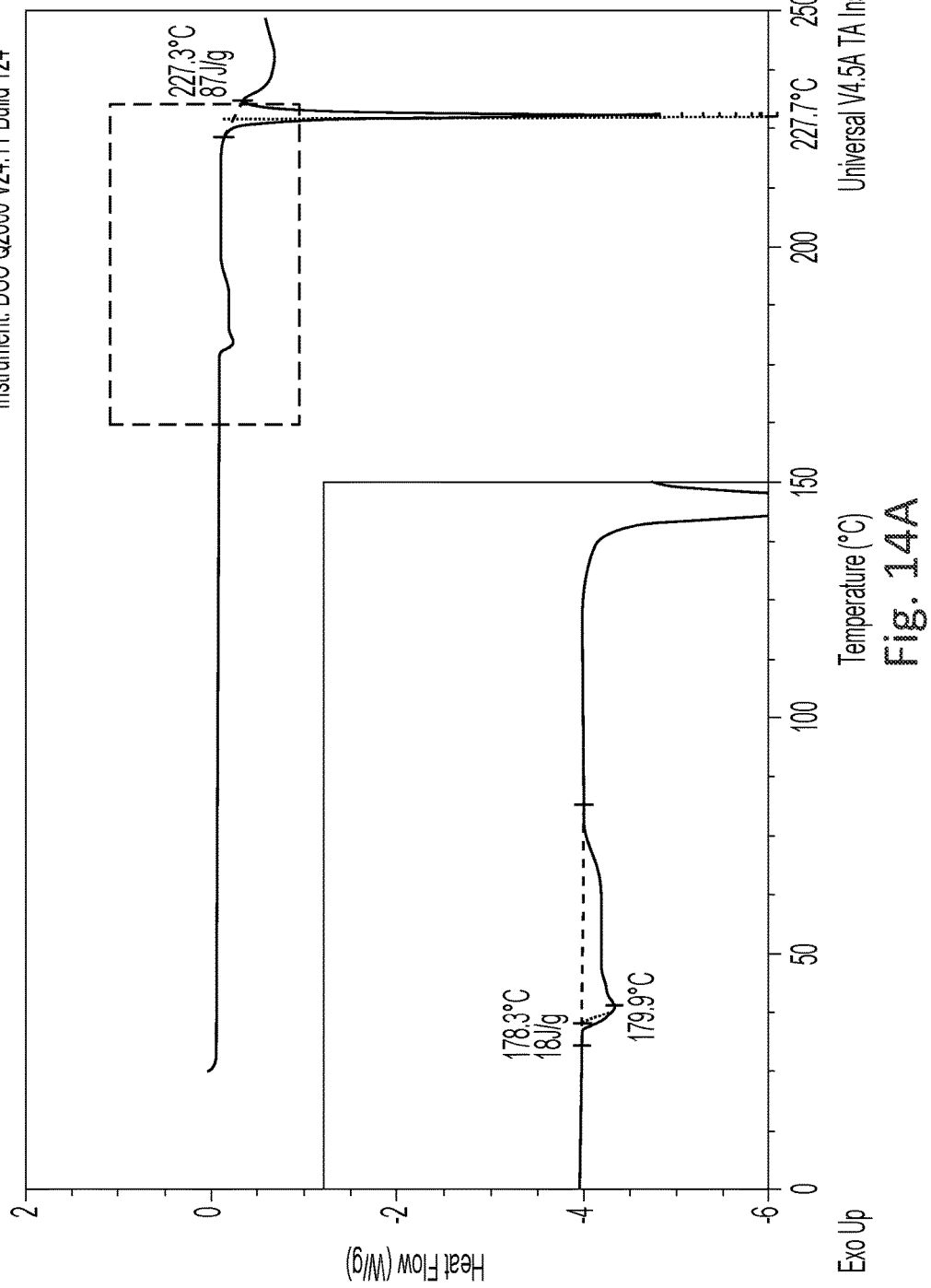

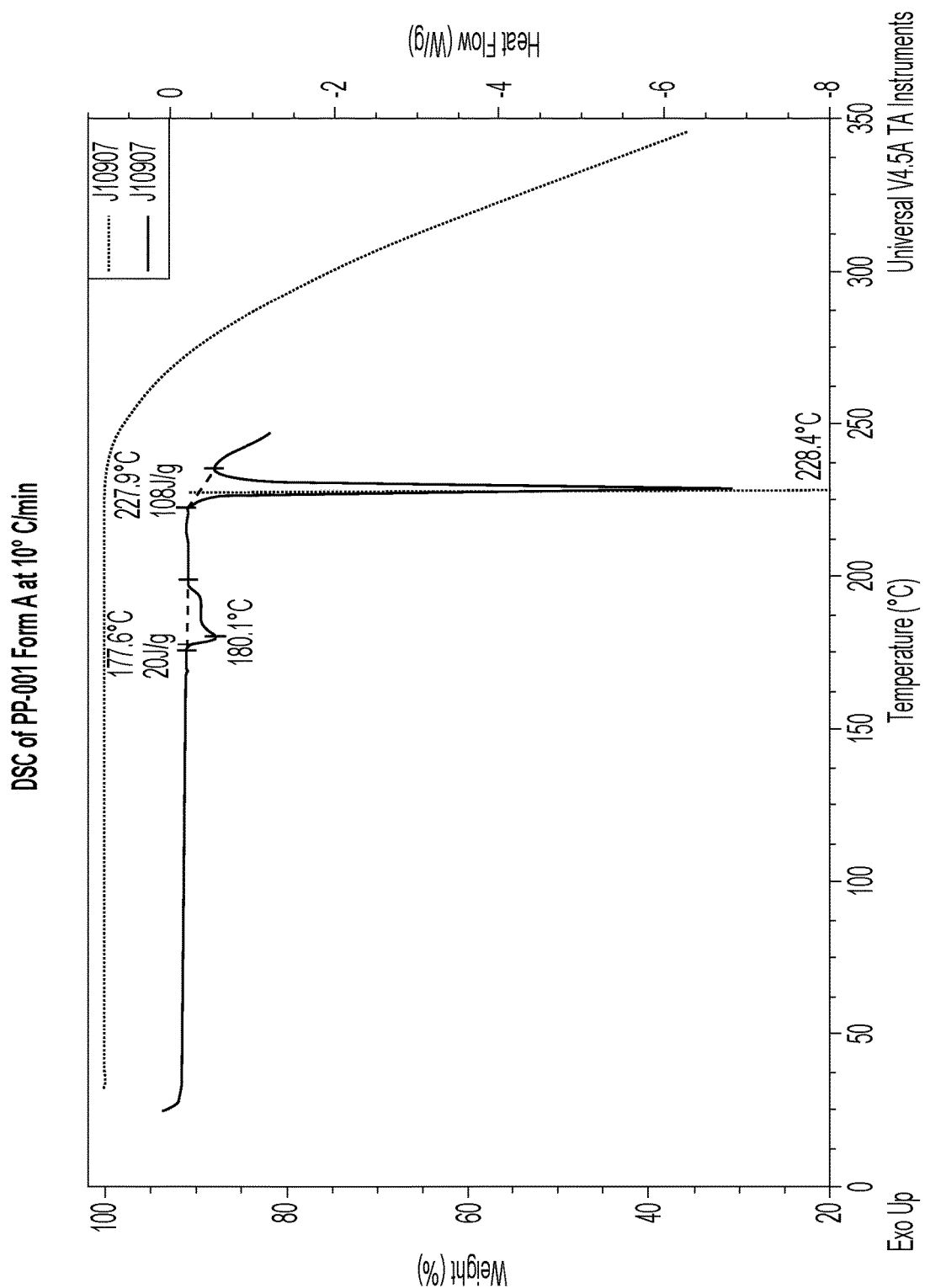

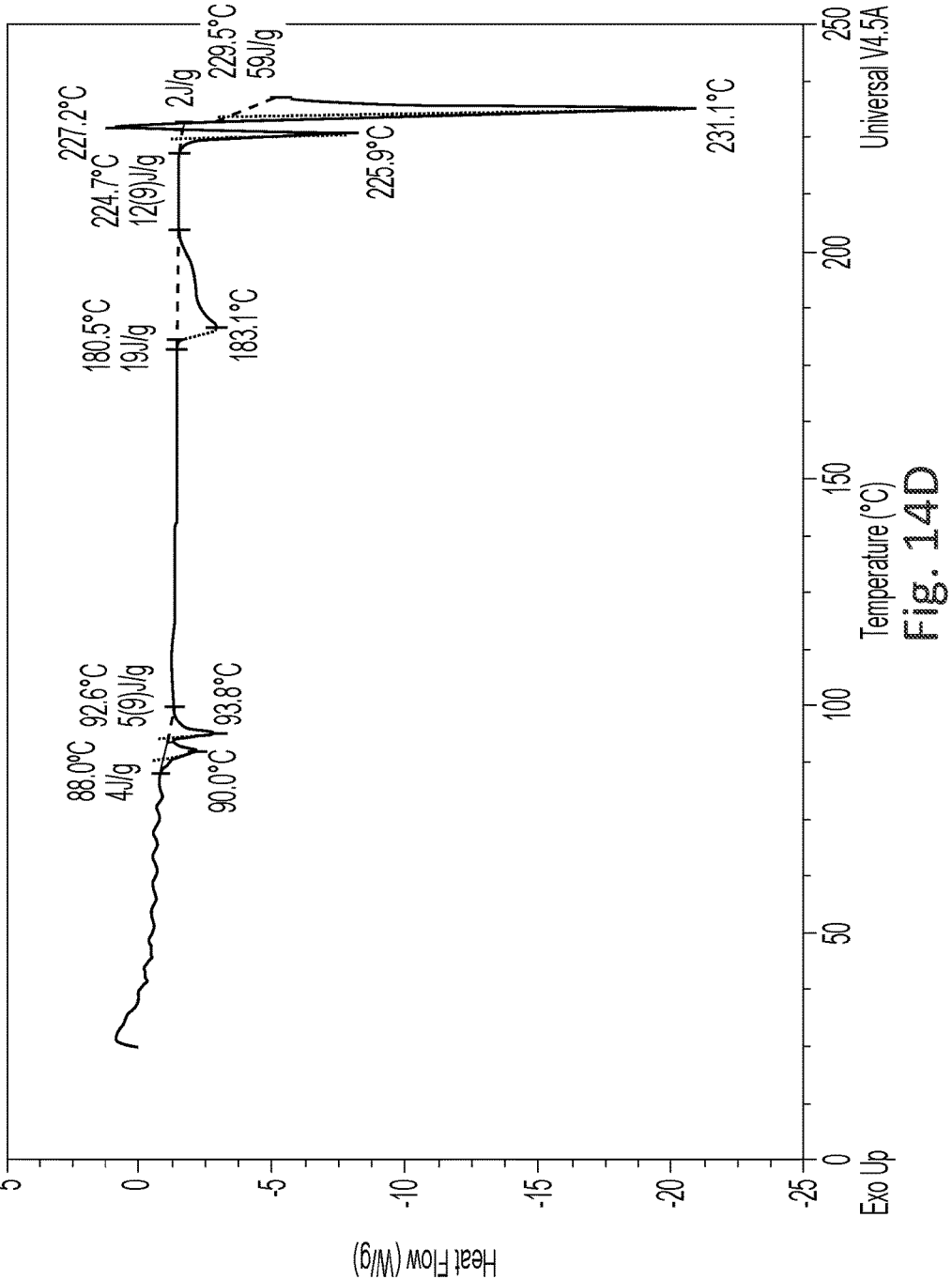

B. SEM of PP-001 Form B

A. PLM of PP-001 Form B

Summary of the result from competitive slurrying of Form A and Form B

| Sample ID | Solvent | Temp (°C) | Obs. After 4 Days | XRPD (4 Days) | XRPD (5 Days) |
|---|---|---|---|---|---|
| DS-2045-48-01 | IPA | 5 | Suspension | Form A | N/A |
| DS-2045-48-02 | Heptane | 5 | Suspension | Form A | N/A |
| DS-2045-48-03 | IPAC | 5 | Suspension | Form A | N/A |
| DS-2045-48-04 | IPA:Water (2%) | 5 | Suspension | Form A | N/A |
| DS-2045-48-05 | IPA:Water (5%) | 5 | Suspension | Form A | N/A |
| DS-2045-48-06 | IPA:Water (13:5) | 5 | Suspension | Form A | N/A |
| DS-2045-48-07 | IPA | 25 | Suspension | Form A | N/A |
| DS-2045-48-08 | Heptane | 25 | Suspension | Form A | N/A |
| DS-2045-48-09 | IPAC | 25 | Suspension | Form A | N/A |
| DS-2045-48-10 | IPA:Water (2%) | 25 | Suspension | Form A | N/A |
| DS-2045-48-11 | IPA:Water (5%) | 25 | Suspension | Form A | N/A |
| DS-2045-48-12 | IPA:Water (13:5) | 25 | Suspension | Form A | N/A |
| DS-2045-48-13 | IPA | 50 | Clear Solution with solid on vial walls | Form A* | Form A |
| DS-2045-48-14 | Heptane | 50 | Suspension | Form A | N/A |
| DS-2045-48-15 | IPAC | 50 | Clear Solution with solid on vial walls | Form A* | Form A |
| DS-2045-48-16 | IPA:Water (2%) | 50 | Clear Solution with solid on vial walls | Form A* | Form A |
| DS-2045-48-17 | IPA:Water (5%) | 50 | Clear Solution with solid on vial walls | Form A* | N/A |
| DS-2045-48-18 | IPA:Water (13:5) | 50 | Suspension | Form A | N/A |

* = additional solid mixture (Form A + B) added after 4 days to get a sustained suspension

Fig. 24

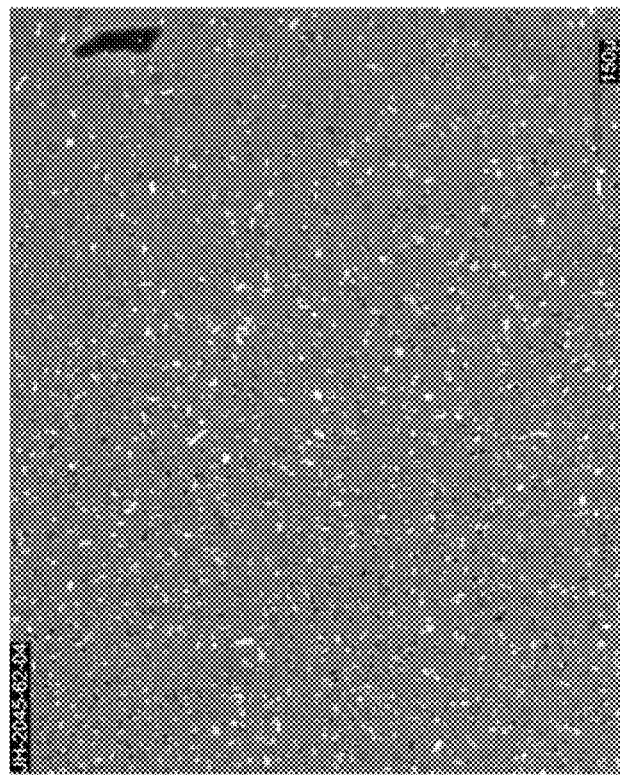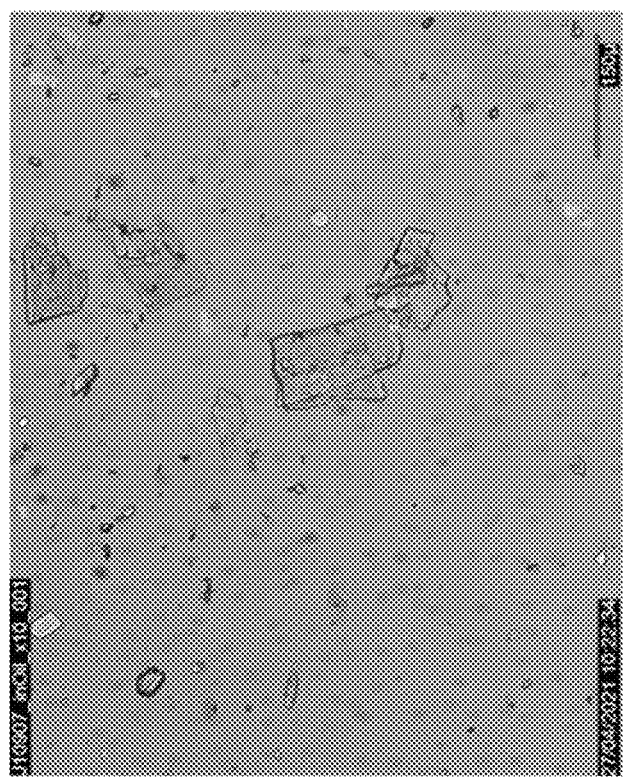
Fig. 28 PLM comparison of supplied PP-001 Form A (J10907) and 1 g scale-up Form A

POLYMORPHS OF A DIHYDROOROTATE DEHYDROGENASE (DHOD) INHIBITOR

FIELD OF THE INVENTION

The present disclosure provides polymorphs of 3-(2,3,5,6-tetrafluoro-3'-trifluoromethoxy-biphenyl-4-ylcarbamoyl)-thiophene-2-carboxylic acid, and methods of making such polymorphs. The present disclosure further provides pharmaceutical compositions and kits comprising polymorphs of the invention, and methods of treating, preventing, or ameliorating a disease or condition comprising administering a polymorph of the invention.

BACKGROUND

The small molecule compound 3-(2,3,5,6-tetrafluoro-3'-trifluoromethoxy-biphenyl-4-ylcarbamoyl)-thiophene-2-carboxylic acid (referred to herein as PP-001), shown below as Formula I, is a potent DHODH inhibitor.

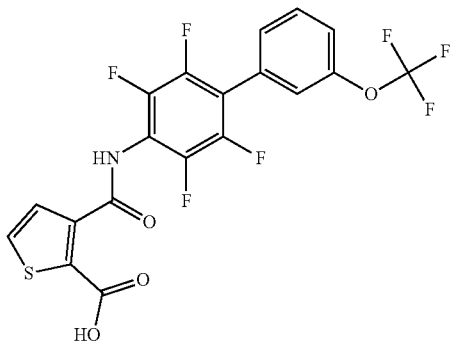

Formula I

See, e.g., U.S. Pat. Nos. 7,365,094, 8,354,433 and 9,795,590, incorporated herein by reference. PP-001 has found application in treating diseases and conditions associated with DHOD activity.

SUMMARY OF THE INVENTION

In some embodiments, the present disclosure relates to a polymorph of 3-(2,3,5,6-tetrafluoro-3'-trifluoromethoxy-biphenyl-4-ylcarbamoyl)-thiophene-2-carboxylic acid, shown below in Formula I:

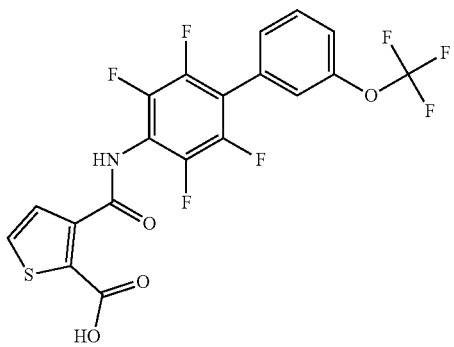

Formula I

In some embodiments the polymorph is Form A comprising an X-ray powder diffraction (XRPD) comprising three or more 2θ values selected from 14.8±0.2, 15.6±0.2, 16.5±0.2, 19.5±0.2, 20.8±0.2, 25.6±0.2, and 26.1±0.2, or Form B comprising an X-ray powder diffraction (XRPD) comprising three or more 2θ values selected from 14.9±0.2, 17.6±0.2, 19.3±0.2, 20.9±0.2, 24.0±0.2, 24.9±0.2, and 25.4±0.2.

In some embodiments, the polymorph is Form A. In some embodiments, the polymorph is Form A and comprises four or more 2θ values selected from 14.8±0.2, 15.6±0.2, 16.5±0.2, 19.5±0.2, 20.8±0.2, 25.6±0.2, and 26.1±0.2. In some embodiments, the polymorph is Form A and comprises give or more 2θ values selected from 14.8±0.2, 15.6±0.2, 16.5±0.2, 19.5±0.2, 20.8±0.2, 25.6±0.2, and 26.1±0.2. In some embodiments, the polymorph is Form A and comprises the XRPD pattern shown in FIG. 2A.

In some embodiments, the polymorph is Form A and comprises one or more characteristics selected from:
  a. a DSC spectrum (5° C./min) comprising an endotherm onset at 178.3±1.0° C., and a second endotherm onset at 227.3±1.0° C.;
  b. a DSC spectrum (10° C./min) comprising an endotherm onset at 177.6±1.0° C., and an endotherm onset at 227.9±1.0° C.;
  c. a DSC spectrum (20° C./min) comprising an endotherm onset at 178.5±1.0° C., and an endotherm onset at 222.5±1.0° C. and 224.3±1.0° C., followed by an endotherm onset at 227.8±1.0° C.;
  d. a DSC spectrum (50° C./min) comprising double endotherm onsets at 88.0±1.0° C. and 92.6±1.0° C., a second endotherm onset at 180.5±1.0° C., a sharp endo/exo onset at 224.7±1.0° C., and an endotherm onset at 229.5±1.0° C.;
  e. a melt-quench-cool (MDSC) comprising an endotherm onset at 177.7±1.0° C., an endotherm onset at 227.8±1.0° C.; or
  f. a VT-XRPD pattern with observable changes at 200±1.0° C.

In some embodiments, the polymorph is Form B. In some embodiments, the polymorph is Form B and comprises four or more 2θ values selected from 14.9±0.2, 17.6±0.2, 19.3±0.2, 20.9±0.2, 24.0±0.2, 24.9±0.2, and 25.4±0.2. In some embodiments, the polymorph is Form B and comprises five or more 2θ values selected from 14.9±0.2, 17.6±0.2, 19.3±0.2, 20.9±0.2, 24.0±0.2, 24.9±0.2, and 25.4±0.2. In some embodiments, the polymorph is Form B and comprises the XRPD pattern shown in FIG. 2B.

In some embodiments, the present disclosure relates to a pharmaceutical composition comprising polymorph Form A or Form B of 3-(2,3,5,6-tetrafluoro-3'-trifluoromethoxy-biphenyl-4-ylcarbamoyl)-thiophene-2-carboxylic acid and a pharmaceutically acceptable excipient, carrier, or diluent.

In some embodiments, the present disclosure relates to a kit comprising polymorph Form A or Form B of 3-(2,3,5,6-tetrafluoro-3'-trifluoromethoxy-biphenyl-4-ylcarbamoyl)-thiophene-2-carboxylic acid and a container.

In some embodiments, the present disclosure relates to a method of preparing polymorph Form A of 3-(2,3,5,6-tetrafluoro-3'-trifluoromethoxy-biphenyl-4-ylcarbamoyl)-thiophene-2-carboxylic acid, the method comprising:
  a) obtaining a sample comprising 3-(2,3,5,6-tetrafluoro-3'-trifluoromethoxy-biphenyl-4-ylcarbamoyl)-thiophene-2-carboxylic acid;
  b) dissolving the sample of (a) in a solvent comprising $C_1$-$C_5$ alcohol, $C_1$-$C_5$ ketone, or $C_1$-$C_5$ acetate solvent at 20° C. to 60° C. to form a solution; and c) removing the solvent from the solution to obtain the polymorph Form A.

In some embodiments, the $C_1$-$C_5$ alcohol is selected from methanol, ethanol, 1-propanol, isopropanol, 1-butanol, 2-butanol, 2-pentanol, or isopentanol. In some embodiments, the $C_1$-$C_5$ ketone is selected from methyl ethyl ketone (MEK), methylisobutyl ketone (MIBK), or acetone.

In some embodiments, the $C_1$-$C_5$ acetate is selected from methyl acetate, ethyl acetate, propyl acetate, butyl acetate, or pentyl acetate.

In some embodiments, the solution is greater than 80% $C_1$-$C_5$ alcohol, $C_1$-$C_5$ ketone, or $C_1$-$C_5$ acetate. In some embodiments, the solution comprises 0% to 20% water.

In some embodiments, after the dissolving in (b), the solution is cooled to an incubation temperature of 1° C. to 10° C. for a period of time. In some embodiments, the cooling to the incubation temperature is at a rate of about 0.02° C./min to about 1° C./min until the incubation temperature is reached. In some embodiments, the cooling to the incubation temperature is at a rate of about 0.05° C./min to about 0.5° C./min until the incubation temperature is reached.

In some embodiments, the period of time for the incubation temperature is about 1 hour to about 48 hours. In some embodiments, the period of time for the incubation temperature is about 6 hours to about 18 hours.

In some embodiments, the removing of the solvent is performed by evaporation. In some embodiments, the removing of the solvent is performed by filtration. In some embodiments, the evaporation occurs at about 20° C. to about 35° C.

In some embodiments, the present invention relates to a method of treating, preventing, or ameliorating a disease or condition in a subject in need thereof comprising administering to the subject a pharmaceutically effective amount of polymorph Form A of 3-(2,3,5,6-tetrafluoro-3'-trifluoromethoxy-biphenyl-4-ylcarbamoyl)-thiophene-2-carboxylic acid.

In some embodiments, the present invention relates to a method of preparing a pharmaceutical composition, the method comprising combining polymorph Form A of 3-(2,3,5,6-tetrafluoro-3'-trifluoromethoxy-biphenyl-4-ylcarbamoyl)-thiophene-2-carboxylic acid with one or more pharmaceutically acceptable excipients, diluents, or carriers.

BRIEF DESCRIPTION OF THE DRAWINGS

FIG. 2A-2D shows the X-Ray Powder Diffraction (XRPD) profiles of PP-001 Form A, Form B, an overlay of Forms A and B, and amorphous PP-001, respectively.

FIG. 3A-3B shows the results of a solubility assessment of PP-001 in various solvent systems and treatments.

FIG. 4A-4B presents the results of a crystal polymorph screen of PP-001 using the indicated solvent systems and treatment.

FIG. 5 shows the results of a solubility screen of amorphous PP-001 using the indicated solvents and treatments.

FIG. 6A-6B presents observations and results from the maturation of amorphous PP-001 at 5° C. using the indicated solvents.

FIG. 8A-8B presents observations and results from maturation by temperature cycling of amorphous PP-001 using the indicated solvents.

FIG. 9A-9B presents observations and results from the maturation of amorphous PP-001 at 50° C. using the indicated solvents.

FIG. 10 presents observations and results from an antisolvent polymorph screen using the indicated solvents and conditions.

FIG. 13A-13B shows an overlay of XPRD profiles of PP-001 starting material, and PP-001 Form A after storage at 40° C./75% relative humidity for 8 days, and (C) PP-001 Form A after storage at 25° C./97% relative humidity for 8 days.

FIG. 14A-14D show the results of Differential Scanning Calorimetry (DSC) analysis of PP-001 Form A at (A) 5° C./min, (B) 10° C./min, (C) 20° C./min, and (D) 50° C./min.

FIG. 24 presents a summary of results for the competitive slurrying of PP-001 Forms A and B.

FIG. 28 shows a comparison of PLM images of PP-001 Form A starting material and PP-001 Form A crystals after 1 g scale-up crystallization.

DETAILED DESCRIPTION OF THE INVENTION

Figure 1:
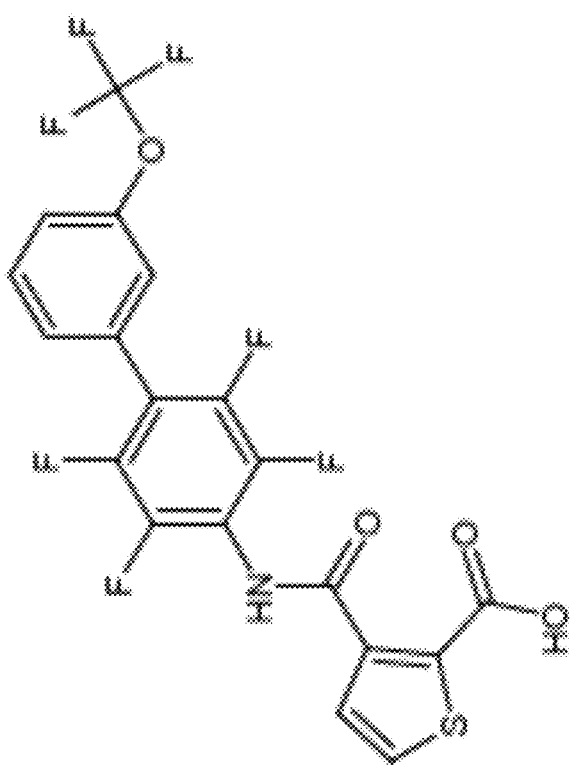
FIG. 1 shows the chemical structure of 3-(2,3,5,6-tetrafluoro-3'-trifluoromethoxy-biphenyl-4-ylcarbamoyl)-thiophene-2-carboxylic acid (PP-001).

The present disclosure relates to polymorphic forms of the dihydroorotate dehydrogenase (DHODH) inhibitor 3-(2,3,5, 6-tetrafluoro-3'-trifluoromethoxy-biphenyl-4-ylcarbamoyl)-thiophene-2-carboxylic acid, methods for their manufacture, pharmaceutical compositions containing them and to their use for the treatment and prevention of diseases, in particular their use in diseases where there is an advantage in inhibiting dihydroorotate dehydrogenase (DHODH).

Different polymorphic forms of a given compound, e.g., PP-001 may have different properties, such as solubility, dissolution rate, suspension stability, stability during milling, vapor pressure, optical and mechanical properties, hygroscopicity, crystal size, filtration performance, drying, density, melting point, degradation stability, stability to prevent phase change to other forms, color and even chemical reactivity. More importantly, in some embodiments, the different forms of a small molecule compound such as PP-001 can change its dissolution, dissolution performance, pharmacokinetics and bioavailability, which can, in some instances, affect the efficacy and safety performance of a drug.

In particular, in some embodiments, crystal forms of PP-001 can affect its dissolution, absorption in vivo, thereby affecting its clinical therapeutic effect and safety to a certain extent. In some embodiments, crystal forms of PP-01 can be critical for drug quality control. The present disclosure relates to polymorphic forms of PP-001 and compositions and kits thereof, methods of making polymorphic forms of PP-001, and methods of treating, preventing, or ameliorating a disease, disorder, or condition by administering a therapeutically effective amount of a polymorphic form of PP-001.

The present disclosure provides new polymorphic forms of PP-001. The present application describes the chemical and physical characteristics of these polymorphic forms, and discloses methods for making these polymorph forms.

A list of abbreviations used throughout the specification is shown in Table. 1.

TABLE 1

List of abbreviations

| Acronym | Meaning |
|---|---|
| $^1$H NMR | Proton Nuclear Magnetic Resonance |
| ACN | Acetonitrile |
| API | Active Pharmaceutical Ingredient |
| ASR | Analytical Service Report |
| ca. | Approximately |
| DCM | Dichloromethane |
| DMSO | Dimethyl sulfoxide |
| DSC | Differential Scanning Calorimetry |
| DVS | Dynamic Vapor Sorption |
| Equiv. | Equivalents |
| EtOAc | Ethyl acetate |
| EtOH | Ethanol |
| GVS | Gravimetric Vapor Sorption |
| $H_2O$ | Water |
| HPLC | High Performance Liquid Chromatography |
| HSM | Hot Stage Microscopy |
| IC | Ion Chromatography |
| ID | Identification |
| IDR | Intrinsic Dissolution Rate |
| IPA | 2-Propanol |
| KF | Karl Fischer |
| MDSC | Modulated Differential Scanning Calorimetry |
| MEK | Methyl ethyl ketone |
| MeOH | Methanol |
| MIBK | Methyl isobutyl ketone |
| MSZW | Metastable Zone Width |
| N/A | Not Applicable |
| NMR | Nuclear Magnetic Resonance |
| No. | Number |
| PLM | Polarized Light Microscopy |

TABLE 1-continued

List of abbreviations

| Acronym | Meaning |
|---|---|
| PTFE | Polytetrafluoroethylene |
| RH | Relative Humidity |
| RT | Room Temperature |
| SCXRD | Single Crystal X-Ray Diffraction |
| SEM | Scanning Electron Microscope |
| Ssat | Supersaturation |
| TBME | tert-Butyl methyl ether |
| t-BuOH | tert-Butanol |
| TFA | Trifluoroacetic acid |
| $T_g$ | Glass transition temperature |
| TGA | Thermal Gravimetric Analysis |
| THF | Tetrahydrofuran |
| TRIS | Tris(hydroxymethyl)aminomethane |
| UV | Ultraviolet |
| Vol | Volumes |
| VT-XRPD | Variable Temperature X-Ray Powder Diffraction |
| XRPD | X-Ray Powder Diffraction |

Unless otherwise defined herein, scientific and technical terms used in the present disclosure shall have the meanings that are commonly understood by one of ordinary skill in the art. Further, unless otherwise required by context, singular terms shall include pluralities and plural terms shall include the singular. As used herein, "a" or "an" may mean one or more. As used herein, when used in conjunction with the word "comprising," the words "a" or "an" may mean one or more than one. As used herein, "another" or "a further" may mean at least a second or more.

Throughout this application, the term "about" is used to indicate that a value includes the inherent variation of error for the method/device being employed to determine the value, or the variation that exists among the study subjects. Typically, the term "about" is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability, depending on the situation.

The use of the term "or" in the claims is used to mean "and/or", unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited, elements or method steps. It is contemplated that any embodiment discussed in this specification can be implemented with respect to salt, methods, and/or kits of the present disclosure. Furthermore, salts and/or kits of the present disclosure can be used to achieve the methods of the present disclosure.

The use of the term "for example" and its corresponding abbreviation "e.g." (whether italicized or not) means that the specific terms recited are representative examples and embodiments of the disclosure that are not intended to be limited to the specific examples referenced or cited unless explicitly stated otherwise.

As used herein, "between" is a range inclusive of the ends of the range. For example, a number between x and y explicitly includes the numbers x and y, and any numbers that fall within x and y.

For a characteristic diffraction peak represented by a 2 theta (2θ) angle, the term "about" means that the listed value varies by no more than 0.2°, for example, about X°, it means X±0.2°, preferably X±0.1°. Thus, in some embodiments, any of the 2θ angle recited herein can be ±0.1.

As used herein, the term "room temperature" generally refers to 4° C. to 30° C., 18° C. to 22° C., 19° C. to 21° C. or 20±5° C.

The disclosure herein provides polymorphs of 3-(2,3,5,6-tetrafluoro-3'-trifluoromethoxy-biphenyl-4-ylcarbamoyl)-thiophene-2-carboxylic acid (PP-001) in various crystal forms, e.g., Form A, Form B as well as in amorphous form.

In some embodiments, the PP-001 is in polymorph Form A. In some embodiments, the term "Form A" refers to a polymorph pf PP-001 having comprising an X-ray powder diffraction (XRPD) comprising three or more 2θ values selected from 14.8±0.2, 15.6±0.2, 16.5±0.2, 19.6±0.2, 20.8±0.2, 25.6±0.2 and 26.1±0.2.

In some embodiments, the Form A polymorph of PP-001 comprises an X-ray powder diffraction (XRPD) comprising a 2θ values at 14.8±0.2, and two other 2θ values selected from 15.6±0.2, 16.5±0.2, 19.6±0.2, 20.8±0.2, 25.6±0.2 and 26.1±0.2. In some embodiments, the Form A polymorph of PP-001 comprises an X-ray powder diffraction (XRPD) comprising a 2θ values at 15.6±0.2, and two other 2θ values selected from 14.8±0.2, 16.5±0.2, 19.6±0.2, 20.8±0.2, 25.6±0.2 and 26.1±0.2. In some embodiments, the Form A polymorph of PP-001 comprises an X-ray powder diffraction (XRPD) comprising a 2θ values at 16.5±0.2, and two other 2θ values selected from 14.8±0.2, 15.6±0.2, 19.6±0.2, 20.8±0.2, 25.6±0.2 and 26.1±0.2. In some embodiments, the Form A polymorph of PP-001 comprises an X-ray powder diffraction (XRPD) comprising a 2θ values at 19.6±0.2, and two other 2θ values selected from 14.8±0.2, 15.6±0.2, 16.5±0.2, 20.8±0.2, 25.6±0.2 and 26.1±0.2. In some embodiments, the Form A polymorph of PP-001 comprises an X-ray powder diffraction (XRPD) comprising a 2θ values at 20.8±0.2, and two other 2θ values selected from 14.8±0.2, 15.6±0.2, 16.5±0.2, 19.6±0.2, 25.6±0.2 and 26.1±0.2. In some embodiments, the Form A polymorph of PP-001 comprises an X-ray powder diffraction (XRPD) comprising a 2θ values at 25.6±0.2, and two other 2θ values selected from 14.8±0.2, 15.6±0.2, 16.5±0.2, 19.6±0.2, 20.8±0.2 and 26.1±0.2. In some embodiments, the Form A polymorph of PP-001 comprises an X-ray powder diffraction (XRPD) comprising a 2θ values at 26.1±0.2, and two other 2θ values selected from 14.8±0.2, 15.6±0.2, 16.5±0.2, 19.6±0.2, 20.8±0.2 and 25.6±0.2.

In some embodiments, the Form A polymorph of PP-001 comprises an X-ray powder diffraction (XRPD) comprising a 2θ values at 14.8±0.2, and three other 2θ values selected from 15.6±0.2, 16.5±0.2, 19.6±0.2, 20.8±0.2, 25.6±0.2 and 26.1±0.2. In some embodiments, the Form A polymorph of PP-001 comprises an X-ray powder diffraction (XRPD) comprising a 2θ values at 15.6±0.2, and three other 2θ values selected from 14.8±0.2, 16.5±0.2, 19.6±0.2, 20.8±0.2, 25.6±0.2 and 26.1±0.2. In some embodiments, the Form A polymorph of PP-001 comprises an X-ray powder diffraction (XRPD) comprising a 2θ values at 16.5±0.2, and three other 2θ values selected from 14.8±0.2, 15.6±0.2, 19.6±0.2, 20.8±0.2, 25.6±0.2 and 26.1±0.2. In some embodiments, the Form A polymorph of PP-001 comprises an X-ray powder diffraction (XRPD) comprising a 2θ values at 19.6±0.2, and three other 2θ values selected from 14.8±0.2, 15.6±0.2, 16.5±0.2, 20.8±0.2, 25.6±0.2 and 26.1±0.2. In some embodiments, the Form A polymorph of PP-001 comprises an X-ray powder diffraction (XRPD) comprising a 2θ values at 20.8±0.2, and three other 2θ values selected from 14.8±0.2, 15.6±0.2, 16.5±0.2, 19.6±0.2, 25.6±0.2 and 26.1±0.2. In some embodiments, the Form A polymorph of PP-001 comprises an X-ray powder diffraction (XRPD) comprising a 2θ values at 25.6±0.2, and three other 2θ values selected from 14.8±0.2, 15.6±0.2, 16.5±0.2, 19.6±0.2, 20.8±0.2 and 26.1±0.2. In some embodiments, the Form A polymorph of PP-001 comprises an X-ray powder diffraction (XRPD) comprising a 2θ values at 26.1±0.2, and three other 2θ values selected from 14.8±0.2, 15.6±0.2, 16.5±0.2, 19.6±0.2, 20.8±0.2 and 25.6±0.2.

In some embodiments, the polymorph Form A comprises four or more 2θ values selected from 14.8±0.2, 15.6±0.2, 16.5±0.2, 19.6±0.2, 20.8±0.2, 25.6±0.2 and 26.1±0.2. In some embodiments, the polymorph Form A comprises five or more 2θ values selected from 14.8±0.2, 15.6±0.2, 16.5±0.2, 19.6±0.2, 20.8±0.2, 25.6±0.2 and 26.1±0.2.

Figure 2A:
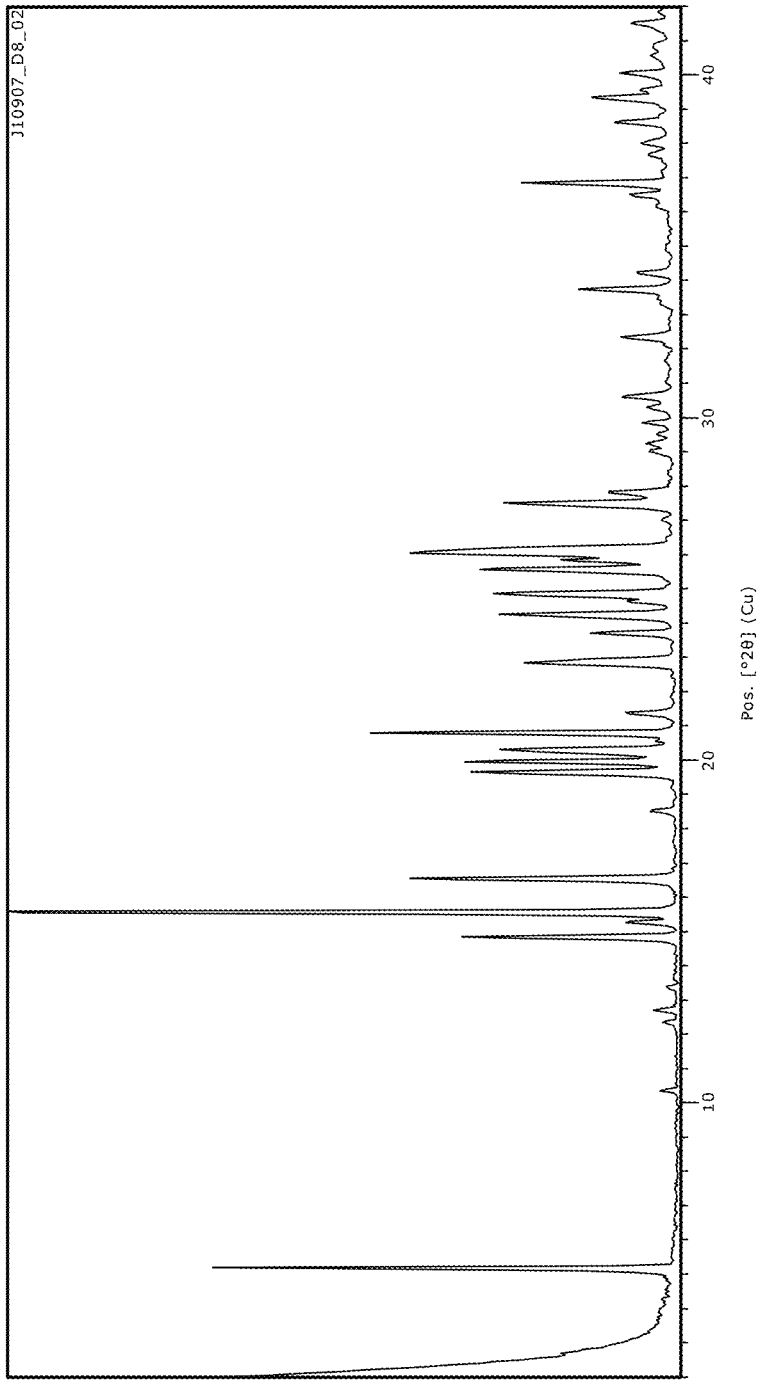

In some embodiments, the polymorph Form A comprises 6 or more 2θ values selected from 14.8±0.2, 15.6±0.2, 16.5±0.2, 19.6±0.2, 20.8±0.2, 25.6±0.2 and 26.1±0.2. In some embodiments, the polymorph Form A comprises 2θ values of 14.8±0.2, 15.6±0.2, 16.5±0.2, 19.6±0.2, 20.8±0.2, 25.6±0.2 and 26.1±0.2. In some embodiments, the term Form A refers to at least 7, 8, 9, 10 or more 2θ peaks is shown in Table 10. In some embodiments, the XRPD pattern of PP-001 Form A is shown in FIG. 2A One of skill in the art will recognize how to determine predominant 2θ values from an XRPD pattern.

In some embodiments, polymorph Form A can be determined by Differential Scanning Calorimetry (DSC) by determining the endotherm onset of the polymorph. In some embodiments, the DSC spectrum can be determined at various rates, e.g., 2° C./min to 10° C./min, 4° C./min to 6° C./min, or 5° C./min. In some embodiments, the DSC spectrum can be determined at various rates, e.g., 10° C./min to 30° C./min, 15° C./min to 25° C./min, or 20° C./min. In some embodiments, the DSC spectrum can be determined at various rates, e.g., 30° C./min to 70° C./min, 40° C./min to 60° C./min, or 50° C./min.

In some embodiments, any of the DSC endotherm onset temperatures described herein can be ±1.0° C. In some embodiments, any of the recited DSC endotherm onset temperatures can be ±0.5° C., ±0.2° C. or 0.1° C. Thus, e.g., if Form A is described as having a DSC spectrum comprising an endotherm onset at about 178.3° C. at 5° C./min, this would include 178.3±1.0° C., 178.3±0.5° C., 178.3±0.2° C., 178.3±0.1° C. or 178.3° C.

In some embodiments, Form A comprises a DSC spectrum (5° C./min) comprising an endotherm onset at about 175° C. to about 180° C., e.g., about 178° C. to about 179° C., e.g., 178.3° C., or e.g., 178.3° C.±0.1. In some embodiments, the Form A comprises a DSC spectrum (5° C./min) comprising a second endotherm onset at about 225° C. to about 230° C., e.g., about 227° C. to about 228° C., e.g., 227.3° C., or e.g., 227.3° C.±0.1.

In some embodiments, Form A comprises a DSC spectrum (10° C./min) comprising an endotherm onset at about 175° C. to about 180° C., e.g., about 177° C. to about 178° C., e.g., 177.6° C., or e.g., 177.6° C.±0.1. In some embodiments, Form A comprises a DSC spectrum (10° C./min) comprising a second an endotherm onset at about 225° C. to about 230° C., e.g., about 227° C. to about 228° C., e.g., 227.9° C. or e.g., 227.9° C.±0.1.

In some embodiments, Form A comprises a DSC spectrum (20° C./min) comprising an endotherm onset at about 175° C. to about 180° C., e.g., about 178° C. to about 179°

C., e.g., 178.5° C., or e.g., 178.5° C.±0.1. In some embodiments, Form A comprises additional endotherm onsets at about 220° C. to about 225° C., e.g., 222.5° C. and about 221° C. to about 226° C., e.g., 224.3° C., or e.g., 224.3° C.±0.1. In some embodiments, Form A comprises an additional endotherm onset at about 225° C. to about 230° C., e.g., 227.8° C., or e.g., 227.8° C.±0.1.

In some embodiments, Form A comprises a DSC spectrum (50° C./min) comprising double endotherm onsets at about 85° C. to about 90° C., e.g., 88.0° C. and about 90° C. to about 95° C., e.g., 92.6° C., or e.g., 92.6° C.±0.1. In some embodiments, as endotherm onset is at about 178° C. to about 182° C., e.g., 180.5° C. or e.g., 180.5° C.±0.1, as endotherm/exotherm onset at about 221° C. to about 226° C., e.g., 224.7° C. or e.g., 224.7° C.±0.1, and an endotherm onset at about 227° C. to about 231° C., e.g., 229.5° C. or e.g., 229.5° C.±0.1.

In some embodiments, Form A exhibits an DSC spectrum at one or more of the rates, e.g., 5° C./min, 10° C./min, 20° C./min, and/or 50° C./min described above.

In some embodiments, any of the polymorphs having a melt-quench-cool (MDSC) endotherm onset temperatures described herein can be ±1.0° C. In some embodiments, any of the recited MDSC endotherm onset temperatures can be ±0.5° C., ±0.2° C. or 0.1° C. Thus, e.g., if Form A is described as having a MDSC spectrum comprising an endotherm onset at about 178.3° C., this would include 178.3±1.0° C., 178.3±0.5° C., 178.3±0.2° C., 178.3±0.1° C. or 178.3° C.

In some embodiments, the Form A polymorph comprises a melt-quench-cool (MDSC) comprising an endotherm onset at about 175° C. to about 180° C., e.g., 177.7° C., or e.g., 177.7° C.±0.1, an endotherm onset at about 225° C. to about 230° C., e.g., 227.8° C. or e.g., 227.8° C.±0.1.

In some embodiments, Form A polymorphs comprise a variable temperature XRPD (VT-XRPD) pattern with observable changes at about 190° C. to about 210° C., e.g., 200° C.

In some embodiments, the disclosure provides a crystalline polymorph Form A of PP-001 that is characterized by one or more of the crystal structure parameters as set forth in Table 2.

TABLE 2

Crystal structure parameters PP-001 polymorph Form A

| | |
|---|---|
| Empirical_formula | $C_{19}H_8F_7NO_4S$ |
| Molecular_weight | 479.32 |
| Unit Cell Dimensions | |
| cell_length_a | 6.9879(5) |
| cell_length_b | 7.7059(6) |
| cell_length_c | 17.1399(18) |
| cell_angle_alpha | 83.690(7) |
| cell_angle_beta | 83.765(7) |
| cell_angle_gamma | 75.804(6) |
| Volume | 886.15(13) |
| cell_formula_units_Z | 2 |
| cell_measurement_temperature | 100(2) |
| cell_measurement_reflns_used | 2229 |
| cell_measurement_theta_min | 3.8145 |
| cell_measurement_theta_max | 71.3432 |
| space_group_id | 1 |
| symmetry_cell_setting | Triclinic |
| space_group_name_H-M_alt | 'P-1' |
| space_group_name_Hall | '-P 1' |
| space_group_IT_number | 2 |
| exptl_crystal_description | Plate |
| exptl_crystal_colour | Colourless |
| exptl_crystal_size_max | 0.15 |

TABLE 2-continued

Crystal structure parameters PP-001 polymorph Form A

| | |
|---|---|
| exptl_crystal_size_mid | 0.10 |
| exptl_crystal_size_min | 0.02 |
| exptl_crystal_density_diffrn | 1.796 |
| exptl_crystal_F_000 | 480 |
| exptl_absorpt_coefficient_mu | 2.609 |
| exptl_absorpt_correction_T_min | 0.79635 |
| exptl_absorpt_correction_T_max | 1.00000 |
| exptl_absorpt_correction_type | 'multi-scan' |
| diffrn_ambient_temperature | 100(2) |
| diffrn_radiation_wavelength | 1.54178 |
| diffrn_radiation_type | CuK\a |
| diffrn_radiation_source | 'SuperNova (Cu) X-ray Source' |
| diffrn_radiation_monochromator | 'mirror' |
| diffrn_measurement_device_type | 'SuperNova, Dual, Cu at zero, Atlas' |
| diffrn_measurement_method | 'omega scans' |
| diffrn_detector_area_resol_mean | 10.5585 |
| diffrn_reflns_number | 6304 |
| diffrn_reflns_av_R_equivalents | 0.0418 |
| diffrn_reflns_av_sigmaI/netI | 0.0549 |
| diffrn_reflns_limit_h_min | −8 |
| diffrn_reflns_limit_h_max | 7 |
| diffrn_reflns_limit_k_min | −9 |
| diffrn_reflns_limit_k_max | 7 |
| diffrn_reflns_limit_l_min | −21 |
| diffrn_reflns_limit_l_max | 21 |
| diffrn_reflns_theta_min | 9.43 |
| diffrn_reflns_theta_max | 71.50 |
| reflns_number_total | 3332 |
| reflns_number_gt | 2555 |
| reflns_threshold_expression | >2sigma(I) |
| refine_ls_structure_factor_coef | Fsqd |
| refine_ls_matrix_type | full |
| refine_ls_weighting_scheme | calc |
| atom_sites_solution_primary | direct |
| atom_sites_solution_secondary | difmap |
| atom_sites_solution_hydrogens | geom |
| refine_ls_hydrogen_treatment | mixed |
| refine_ls_extinction_method | none |
| refine_ls_number_reflns | 3332 |
| refine_ls_number_parameters | 301 |
| refine_ls_number_restraints | 0 |
| refine_ls_R_factor_all | 0.0629 |
| refine_ls_R_factor_gt | 0.0442 |
| refine_ls_wR_factor_ref | 0.1199 |
| refine_ls_wR_factor_gt | 0.1082 |
| refine_ls_goodness_of_fit_ref | 1.028 |
| refine_ls_restrained_S_all | 1.028 |
| refine_ls_shift/su_max | 0.001 |
| refine_ls_shift/su_mean | 0.000 |

The unit cell dimensions are defined by three parameters: length of the sides of the cell; relative angles of the sides to each other and the volume of the cell. The lengths of the sides of the unit cell are defined by a, b and c. The relative angles of the cell sides are defined by $\alpha$, $\beta$ and $\gamma$. Embodiments of the invention further include PP-001 polymorph Form A having atomic positions of all the atoms relative to the origin of the unit cell as recited in Table 3 and Table 4. Table 3 and Table 4 list the parameters of atomic coordinates and, bond lengths and angles of PP-001 Form A as described herein. These parameters define the atomic arrangement in the crystal structure of PP-001 Form A as described herein.

TABLE 3

Atomic Coordinates (×10⁴) and equivalent isotropic displacement parameters (Å² × 10³) of PP-001 polymorph Form A

| Atom | X | Y | Z | U(eq). |
|---|---|---|---|---|
| S1 | 0.74621 (10) | −0.07778 (8) | 1.10240 (4) | 0.02203 (18) |
| F1 | 1.0913 (2) | 0.5380 (2) | 0.84200 (9) | 0.0252 (4) |
| F2 | 1.1583 (2) | 0.6994 (2) | 0.70099 (10) | 0.0272 (4) |
| F3 | 0.5760 (2) | 0.5783 (2) | 0.62299 (9) | 0.0262 (4) |
| F4 | 0.5004 (2) | 0.4403 (2) | 0.76789 (10) | 0.0269 (4) |
| F5 | 0.8061 (3) | 0.8882 (3) | 0.28148 (11) | 0.0449 (5) |
| F6 | 0.4973 (3) | 1.0047 (3) | 0.30920 (12) | 0.0483 (5) |
| F7 | 0.6290 (3) | 0.7354 (3) | 0.35427 (12) | 0.0420 (5) |
| O1 | 0.7614 (3) | −0.3381 (2) | 0.99566 (12) | 0.0273 (5) |
| O2 | 0.7458 (3) | −0.1708 (3) | 0.88286 (12) | 0.0245 (4) |
| O3 | 0.7554 (3) | 0.1421 (2) | 0.83971 (11) | 0.0241 (4) |
| O4 | 0.6917 (3) | 0.9701 (3) | 0.40204 (12) | 0.0302 (5) |
| N1 | 0.7644 (4) | 0.4011 (3) | 0.88544 (14) | 0.0214 (5) |
| C1 | 0.7525 (4) | −0.1917 (3) | 0.95869 (17) | 0.0219 (6) |
| C2 | 0.7470 (4) | −0.0327 (4) | 1.00220 (16) | 0.0205 (5) |
| C3 | 0.7441 (4) | 0.1469 (4) | 0.97995 (16) | 0.0207 (6) |
| C4 | 0.7411 (4) | 0.2440 (4) | 1.04624 (17) | 0.0225 (6) |
| H4A | 0.7385 | 0.3685 | 1.0424 | 0.027 |
| C5 | 0.7424 (4) | 0.1397 (4) | 1.11552 (18) | 0.0251 (6) |
| C6 | 0.7532 (4) | 0.2278 (3) | 0.89756 (17) | 0.0213 (6) |
| C7 | 0.7978 (4) | 0.4789 (3) | 0.80807 (16) | 0.0207 (6) |
| C8 | 0.9640 (4) | 0.5466 (3) | 0.78799 (16) | 0.0212 (6) |
| C9 | 0.9989 (4) | 0.6268 (4) | 0.71359 (17) | 0.0223 (6) |
| C10 | 0.8769 (4) | 0.6332 (3) | 0.65333 (16) | 0.0210 (6) |
| C11 | 0.7092 (4) | 0.5707 (3) | 0.67566 (16) | 0.0212 (6) |
| C12 | 0.6681 (4) | 0.4954 (3) | 0.75073 (17) | 0.0222 (6) |
| C13 | 0.9300 (4) | 0.7055 (3) | 0.57124 (16) | 0.0216 (6) |
| C14 | 0.7848 (4) | 0.8037 (4) | 0.52258 (17) | 0.0234 (6) |
| H14A | 0.6486 | 0.8274 | 0.5411 | 0.028 |
| C15 | 0.8431 (5) | 0.8652 (4) | 0.44754 (17) | 0.0255 (6) |
| C16 | 1.0399 (5) | 0.8370 (4) | 0.41797 (18) | 0.0286 (6) |
| H16A | 1.0762 | 0.8843 | 0.3665 | 0.034 |
| C17 | 1.1816 (5) | 0.7372 (4) | 0.46609 (17) | 0.0276 (6) |
| H17A | 1.3176 | 0.7140 | 0.4471 | 0.033 |
| C18 | 1.1277 (4) | 0.6708 (4) | 0.54154 (17) | 0.0251 (6) |
| H18A | 1.2269 | 0.6008 | 0.5734 | 0.030 |
| C19 | 0.6579 (5) | 0.9004 (4) | 0.33809 (18) | 0.0301 (7) |
| H5A | 0.739 (5) | 0.174 (4) | 1.165 (2) | 0.023 (8) |
| H1A | 0.775 (6) | 0.461 (5) | 0.922 (2) | 0.041 (11) |
| H2A | 0.734 (7) | −0.047 (6) | 0.864 (3) | 0.067 (14) |

TABLE 4

Bond lengths [Å] and angles [°] for PP-001 polymorph Form A

| S1—C5 | 1.709 (3) |
| S1—C2 | 1.714 (3) |
| F1—C8 | 1.338 (3) |
| F2—C9 | 1.352 (3) |
| F3—C11 | 1.352 (3) |
| F4—C12 | 1.335 (3) |
| F5—C19 | 1.333 (4) |
| F6—C19 | 1.320 (4) |
| F7—C19 | 1.331 (4) |
| O1—C1 | 1.223 (3) |
| O2—C1 | 1.297 (3) |
| O2—H2A | 0.96 (5) |
| O3—C6 | 1.247 (3) |
| O4—C19 | 1.339 (4) |
| O4—C15 | 1.415 (4) |
| N1—C6 | 1.349 (3) |
| N1—C7 | 1.414 (3) |
| N1—H1A | 0.84 (4) |
| C1—C2 | 1.493 (4) |
| C2—C3 | 1.390 (4) |
| C3—C4 | 1.423 (4) |
| C3—C6 | 1.481 (4) |
| C4—C5 | 1.358 (4) |
| C4—H4A | 0.9500 |
| C5—H5A | 0.91 (3) |
| C7—C8 | 1.382 (4) |
| C7—C12 | 1.383 (4) |
| C8—C9 | 1.379 (4) |
| C9—C10 | 1.394 (4) |
| C10—C11 | 1.388 (4) |
| C10—C13 | 1.490 (4) |
| C11—C12 | 1.383 (4) |
| C13—C18 | 1.391 (4) |
| C13—C14 | 1.402 (4) |
| C14—C15 | 1.375 (4) |
| C14—H14A | 0.9500 |
| C15—C16 | 1.386 (4) |
| C16—C17 | 1.385 (4) |
| C16—H16A | 0.9500 |
| C17—C18 | 1.385 (4) |
| C17—H17A | 0.9500 |
| C18—H18A | 0.9500 |
| C5—S1—C2 | 92.10 (14) |
| C1—O2—H2A | 110 (3) |
| C19—O4—C15 | 116.9 (2) |
| C6—N1—C7 | 120.1 (2) |
| C6—N1—H1A | 122 (3) |
| C7—N1—H1A | 117 (3) |
| O1—C1—O2 | 121.7 (2) |
| O1—C1—C2 | 119.1 (3) |
| O2—C1—C2 | 119.3 (2) |
| C3—C2—C1 | 134.5 (3) |
| C3—C2—S1 | 111.2 (2) |
| C1—C2—S1 | 114.29 (19) |

TABLE 4-continued

Bond lengths [Å] and angles [°] for PP-001 polymorph Form A

| | |
|---|---|
| C2—C3—C4 | 111.7 (2) |
| C2—C3—C6 | 124.9 (3) |
| C4—C3—C6 | 123.3 (2) |
| C5—C4—C3 | 112.8 (2) |
| C5—C4—H4A | 123.6 |
| C3—C4—H4A | 123.6 |
| C4—C5—S1 | 112.2 (2) |
| C4—C5—H5A | 128 (2) |
| S1—C5—H5A | 120 (2) |
| O3—C6—N1 | 119.2 (3) |
| O3—C6—C3 | 123.0 (2) |
| N1—C6—C3 | 117.7 (2) |
| C8—C7—C12 | 117.4 (3) |
| C8—C7—N1 | 119.6 (2) |
| C12—C7—N1 | 123.0 (2) |
| F1—C8—C9 | 119.2 (2) |
| F1—C8—C7 | 119.6 (2) |
| C9—C8—C7 | 121.1 (2) |
| F2—C9—C8 | 116.9 (2) |
| F2—C9—C10 | 120.4 (2) |
| C8—C9—C10 | 122.7 (2) |
| C11—C10—C9 | 114.7 (2) |
| C11—C10—C13 | 123.7 (2) |
| C9—C10—C13 | 121.6 (2) |
| F3—C11—C12 | 116.6 (2) |
| F3—C11—C10 | 120.2 (2) |
| C12—C11—C10 | 123.3 (2) |
| F4—C12—C11 | 119.4 (2) |
| F4—C12—C7 | 120.0 (2) |
| C11—C12—C7 | 120.6 (3) |
| C18—C13—C14 | 118.9 (3) |
| C18—C13—C10 | 119.5 (2) |
| C14—C13—C10 | 121.5 (3) |
| C15—C14—C13 | 118.8 (3) |
| C15—C14—H14A | 120.6 |
| C13—C14—H14A | 120.6 |
| C14—C15—C16 | 123.0 (3) |
| C14—C15—O4 | 116.6 (3) |
| C16—C15—O4 | 120.4 (3) |
| C17—C16—C15 | 117.7 (3) |
| C17—C16—H16A | 121.2 |
| C15—C16—H16A | 121.2 |
| C16—C17—C18 | 120.8 (3) |
| C16—C17—H17A | 119.6 |
| C18—C17—H17A | 119.6 |
| C17—C18—C13 | 120.7 (3) |
| C17—C18—H18A | 119.6 |
| C13—C18—H18A | 119.6 |
| F6—C19—F7 | 108.3 (3) |
| F6—C19—F5 | 108.1 (2) |
| F7—C19—F5 | 106.1 (3) |
| F6—C19—O4 | 108.3 (3) |
| F7—C19—O4 | 112.5 (2) |
| F5—C19—O4 | 113.4 (3) |

The DSC, GVS, PLM, SEM, and HPLC characteristics of PP-001 Form A are discussed and exemplified in more detail below in Example 3, and thermal studies on Form A are discussed in more detail in Example 4.

In some embodiments, the polymorph of PP-001 is in Form B. In some embodiments, Form B comprises an X-ray powder diffraction (XRPD) comprising three or more 2θ values selected from 14.9±0.2, 17.6±0.2, 19.3±0.2, 20.9±0.2, 24.0±0.2, 24.9±0.2 and 25.4±0.2.

In some embodiments, the Form B polymorph of PP-001 comprises an X-ray powder diffraction (XRPD) comprising a 2θ values at 14.9±0.2, and two other 2θ values selected from 17.6±0.2, 19.3±0.2, 20.9±0.2, 24.0±0.2, 24.9±0.2 and 25.4±0.2. In some embodiments, the Form B polymorph of PP-001 comprises an X-ray powder diffraction (XRPD) comprising a 2θ values at 17.6±0.2, and two other 2θ values selected from 14.9±0.2, 19.3±0.2, 20.9±0.2, 24.0±0.2, 24.9±0.2 and 25.4±0.2. In some embodiments, the Form B polymorph of PP-001 comprises an X-ray powder diffraction (XRPD) comprising a 2θ values at 19.3±0.2, and two other 2θ values selected from 14.9±0.2, 17.6±0.2, 20.9±0.2, 24.0±0.2, 24.9±0.2 and 25.4±0.2. In some embodiments, the Form B polymorph of PP-001 comprises an X-ray powder diffraction (XRPD) comprising a 2θ values at 20.9±0.2, and two other 2θ values selected from 14.9±0.2, 17.6±0.2, 19.3±0.2, 24.0±0.2, 24.9±0.2 and 25.4±0.2. In some embodiments, the Form B polymorph of PP-001 comprises an X-ray powder diffraction (XRPD) comprising a 2θ values at 24.0±0.2, and two other 2θ values selected from 14.9±0.2, 17.6±0.2, 19.3±0.2, 20.9±0.2, 24.9±0.2 and 25.4±0.2. In some embodiments, the Form B polymorph of PP-001 comprises an X-ray powder diffraction (XRPD) comprising a 2θ values at 24.9±0.2, and two other 2θ values selected from 14.9±0.2, 17.6±0.2, 19.3±0.2, 20.9±0.2, 24.0±0.2, and 25.4±0.2. In some embodiments, the Form B polymorph of PP-001 comprises an X-ray powder diffraction (XRPD) comprising a 2θ values at 25.4±0.2, and two other 2θ values selected from 14.9±0.2, 17.6±0.2, 19.3±0.2, 20.9±0.2, 24.0±0.2, and 24.9±0.2.

In some embodiments, the Form B polymorph of PP-001 comprises an X-ray powder diffraction (XRPD) comprising a 2θ values at 14.9±0.2, and three other 2θ values selected from 17.6±0.2, 19.3±0.2, 20.9±0.2, 24.0±0.2, 24.9±0.2 and 25.4±0.2. In some embodiments, the Form B polymorph of PP-001 comprises an X-ray powder diffraction (XRPD) comprising a 2θ values at 17.6±0.2, and three other 2θ values selected from 14.9±0.2, 19.3±0.2, 20.9±0.2, 24.0±0.2, 24.9±0.2 and 25.4±0.2. In some embodiments, the Form B polymorph of PP-001 comprises an X-ray powder diffraction (XRPD) comprising a 2θ values at 19.3±0.2, and three other 2θ values selected from 14.9±0.2, 17.6±0.2, 20.9±0.2, 24.0±0.2, 24.9±0.2 and 25.4±0.2. In some embodiments, the Form B polymorph of PP-001 comprises an X-ray powder diffraction (XRPD) comprising a 2θ values at 20.9±0.2, and three other 2θ values selected from 14.9±0.2, 17.6±0.2, 19.3±0.2, 24.0±0.2, 24.9±0.2 and 25.4±0.2. In some embodiments, the Form B polymorph of PP-001 comprises an X-ray powder diffraction (XRPD) comprising a 2θ values at 24.0±0.2, and three other 2θ values selected from 14.9±0.2, 17.6±0.2, 19.3±0.2, 20.9±0.2, 24.9±0.2 and 25.4±0.2. In some embodiments, the Form B polymorph of PP-001 comprises an X-ray powder diffraction (XRPD) comprising a 2θ values at 24.9±0.2, and three other 2θ values selected from 14.9±0.2, 17.6±0.2, 19.3±0.2, 20.9±0.2, 24.0±0.2, and 25.4±0.2. In some embodiments, the Form B polymorph of PP-001 comprises an X-ray powder diffraction (XRPD) comprising a 2θ values at 25.4±0.2, and three other 2θ values selected from 14.9±0.2, 17.6±0.2, 19.3±0.2, 20.9±0.2, 24.0±0.2, and 24.9±0.2.

In some embodiments, the polymorph of Form B comprises four or more 2θ values selected from 14.8±0.2, 17.6±0.2, 19.3±0.2, 20.9±0.2, 24.0±0.2, 24.9±0.2 and 25.4±0.2. In some embodiments, the polymorph of Form B comprises five or more 2θ values selected from 14.8±0.2, 17.6±0.2, 19.3±0.2, 20.9±0.2, 24.0±0.2, 24.9±0.2 and 25.4±0.2. In some embodiments, the polymorph of Form B comprises 6 or more 2θ values selected from 14.8±0.2, 17.6±0.2, 19.3±0.2, 20.9±0.2, 24.0±0.2, 24.9±0.2 and 25.4±0.2. In some embodiments, the polymorph of Form B comprises 2θ values of 14.8±0.2, 17.6±0.2, 19.3±0.2, 20.9±0.2, 24.0±0.2, 24.9±0.2 and 25.4±0.2.

In some embodiments, the term Form B refers to at least 7, 8, 9, 10 or more 2θ peaks as shown in Table 17. In some embodiments, XRPD pattern of PP-001 Form B is shown in FIG. 2B.

In some embodiments, the disclosure provides a crystalline polymorph Form A of PP-001 that is characterized by one or more of the crystal structure parameters as set forth in Table 5.

TABLE 5

| Crystal structure parameters PP-001 polymorph Form B | |
|---|---|
| Empirical_formula | $C_{19}H_8F_7NO_4S$ |
| Molecular_weight | 479.32 |
| Unit Cell Dimensions | |
| cell_length_a | 7.2753(2) |
| cell_length_b | 33.7612(7) |
| cell_length_c | 7.7034(2) |
| cell_angle_alpha | 90 |
| cell_angle_beta | 106.672(2) |
| cell_angle_gamma | 90 |
| cell_volume | 1812.59(8) |
| cell_formula_units_Z | 4 |
| cell_measurement_temperature | 100(2) |
| cell_measurement_reflns_used | 29061 |
| cell_measurement_theta_min | 2.5450 |
| cell_measurement_theta_max | 77.5340 |
| space_group_crystal_system | monoclinic |
| space_group_IT_number | 14 |
| space_group_name_H-M_alt | 'P 21/n' |
| space_group_name_Hall | '-P 2yn' |
| exptl_crystal_description | plate |
| exptl_crystal_colour | colourless |
| exptl_crystal_density_diffrn | 1.756 |
| exptl_crystal_F_000 | 960 |
| exptl_crystal_size_max | 0.150 |
| exptl_crystal_size_mid | 0.100 |
| exptl_crystal_size_min | 0.020 |
| exptl_absorpt_coefficient_mu | 2.551 |
| shelx_estimated_absorpt_T_min | 0.701 |
| shelx_estimated_absorpt_T_max | 0.951 |
| exptl_absorpt_correction_T_min | 0.72856 |
| exptl_absorpt_correction_T_max | 1.00000 |
| exptl_absorpt_correction_type | multi-scan |
| diffrn_ambient_temperature | 100(2) |
| diffrn_radiation_wavelength | 1.54184 |
| diffrn_radiation_type | CuK\a |
| diffrn_radiation_source | 'PhotonJet (Cu) X-ray Source' |
| diffrn_radiation_monochromator | 'mirror' |
| diffrn_measurement_device_type | 'XtaLAB Synergy-S, Dualflex, HyPix-6000HE' |
| diffrn_measurement_method | 'omega scans' |
| diffrn_detector_area_resol_mean | 10.0000 |
| diffrn_reflns_number | 40641 |
| diffrn_reflns_av_unetI/netI | 0.0137 |
| diffrn_reflns_av_R_equivalents | 0.0386 |
| diffrn_reflns_limit_h_min | −9 |
| diffrn_reflns_limit_h_max | 9 |
| diffrn_reflns_limit_k_min | −41 |
| diffrn_reflns_limit_k_max | 42 |
| diffrn_reflns_limit_l_min | −9 |
| diffrn_reflns_limit_l_max | 9 |
| diffrn_reflns_theta_min | 2.618 |
| diffrn_reflns_theta_max | 77.412 |
| diffrn_reflns_theta_full | 67.684 |
| diffrn_measured_fraction_theta_max | 0.976 |
| diffrn_measured_fraction_theta_full | 1.000 |
| diffrn_reflns_Laue_measured_fraction_max | 0.976 |
| diffrn_reflns_Laue_measured_fraction_full | 1.000 |
| diffrn_reflns_point_group_measured_fraction_max | 0.976 |
| diffrn_reflns_point_group_measured_fraction_full | 1.000 |
| reflns_number_total | 3761 |
| reflns_number_gt | 3629 |
| reflns_threshold_expression | 'I > 2\s(I)' |
| reflns_Friedel_coverage | 0.000 |
| refine_ls_structure_factor_coef | Fsqd |
| refine_ls_matrix_type | full |
| refine_ls_weighting_scheme | calc |
| atom_sites_solution_hydrogens | mixed |
| refine_ls_hydrogen_treatment | mixed |
| refine_ls_extinction_method | none |
| refine_ls_number_reflns | 3761 |
| refine_ls_number_parameters | 297 |
| refine_ls_number_restraints | 0 |

TABLE 5-continued

Crystal structure parameters PP-001 polymorph Form B

| | |
|---|---|
| refine_ls_R_factor_all | 0.0344 |
| refine_ls_R_factor_gt | 0.0335 |
| refine_ls_wR_factor_ref | 0.0886 |
| refine_ls_wR_factor_gt | 0.0880 |
| refine_ls_goodness_of_fit_ref | 1.053 |
| refine_ls_restrained_S_all | 1.053 |
| refine_ls_shift/su_max | 0.001 |
| refine_ls_shift/su_mean | 0.000 |

Embodiments of the invention further include PP-001 polymorph Form B having atomic positions of all the atoms relative to the origin of the unit cell as recited in Table 6 and Table 7. Table 6 and Table 7 list the parameters of atomic coordinates and, bond lengths and angles of PP-001 Form B as described herein. These parameters define the atomic arrangement in the crystal structure of PP-001 Form B as described herein.

TABLE 6

Atomic Coordinates (×10$^4$) and equivalent isotropic displacement parameters (A$^2$ × 10$^3$) of PP-001 polymorph Form B

| Atom | X | Y | Z | U(eq). |
|---|---|---|---|---|
| S1 | 0.80542(5) | 0.44107(2) | 1.06868(5) | 0.01913(11) |
| F1 | 0.7173(2) | 0.83745(4) | 0.2769(2) | 0.0538(4) |
| F2 | 0.48412(17) | 0.85536(3) | 0.37976(16) | 0.0388(3) |
| F3 | 0.67188(18) | 0.80791(4) | 0.50680(17) | 0.0479(3) |
| F4 | 0.95272(13) | 0.64650(3) | 0.29659(12) | 0.0225(2) |
| F5 | 0.99009(12) | 0.57894(3) | 0.48078(12) | 0.0216(2) |
| F6 | 0.38461(13) | 0.59831(3) | 0.57606(12) | 0.0233(2) |
| F7 | 0.35008(13) | 0.66729(3) | 0.40441(13) | 0.0265(2) |
| O1 | 0.45868(17) | 0.79961(3) | 0.23812(17) | 0.0273(3) |
| O2 | 0.67821(16) | 0.57123(3) | 0.87609(14) | 0.0213(2) |
| O3 | 0.67606(16) | 0.54895(3) | 1.17821(14) | 0.0213(2) |
| H3 | 0.672(4) | 0.5598(8) | 1.053(4) | 0.055(7) |
| O4 | 0.74873(17) | 0.49381(3) | 1.33733(14) | 0.0256(3) |
| N1 | 0.70812(18) | 0.54855(3) | 0.61218(17) | 0.0181(3) |
| H1 | 0.729(3) | 0.5288(7) | 0.544(3) | 0.033(5) |
| C1 | 0.5828(3) | 0.82443(5) | 0.3477(3) | 0.0311(4) |
| C2 | 0.5361(2) | 0.76483(5) | 0.1832(2) | 0.0240(3) |
| C3 | 0.5717(2) | 0.76485(5) | 0.0164(2) | 0.0281(4) |
| H3A | 0.5550 | 0.7882 | −0.0552 | 0.034 |
| C4 | 0.6325(2) | 0.72984(5) | −0.0437(2) | 0.0295(4). |
| H4 | 0.6570 | 0.7291 | −0.1583 | 0.035 |
| C5 | 0.6579(2) | 0.69581(5) | 0.0622(2) | 0.0254(3) |
| H5 | 0.6989 | 0.6720 | 0.0192 | 0.031 |
| C6 | 0.6234(2) | 0.69646(5) | 0.2313(2) | 0.0213(3) |
| C7 | 0.5604(2) | 0.73154(5) | 0.2921(2) | 0.0219(3) |
| H7 | 0.5348 | 0.7325 | 0.4062 | 0.026 |
| C8 | 0.6493(2) | 0.65984(4) | 0.3425(2) | 0.0193(3) |
| C9 | 0.8107(2) | 0.63576(4) | 0.3676(2) | 0.0183(3) |
| C10 | 0.8322(2) | 0.60086(4) | 0.46335(19) | 0.0179(3) |
| C11 | 0.6904(2) | 0.58691(4) | 0.53580(19) | 0.0177(3) |
| C12 | 0.5294(2) | 0.61067(5) | 0.5154(2) | 0.0186(3) |
| C13 | 0.5122(2) | 0.64626(5) | 0.4233(2) | 0.0199(3) |
| C14 | 0.7058(2) | 0.54265(4) | 0.7843(2) | 0.0180(3) |
| C15 | 0.7425(2) | 0.50171(4) | 0.85697(19) | 0.0173(3) |
| C16 | 0.7801(2) | 0.46907(4) | 0.7544(2) | 0.0198(3). |
| H16 | 0.7798 | 0.4710 | 0.6312 | 0.024 |
| C17 | 0.8164(2) | 0.43499(5) | 0.8523(2) | 0.0212(3) |
| H17 | 0.8448 | 0.4105 | 0.8052 | 0.025 |
| C18 | 0.7520(2) | 0.49043(4) | 1.0337(2) | 0.0177(3) |
| C19 | 0.7256(2) | 0.51172(5) | 1.1940(2) | 0.0191(3) |

TABLE 7

Bond lengths [Å] and angles [°] for PP-001 polymorph Form B

| | |
|---|---|
| S1—C17 | 1.7040(16) |
| S1—C18 | 1.7149(15) |

TABLE 7-continued

Bond lengths [Å] and angles [°] for PP-001 polymorph Form B

| | |
|---|---|
| F1—C1 | 1.325(2) |
| F2—C1 | 1.330(2) |
| F3—C1 | 1.333(2) |
| F4—C9 | 1.3499(17) |
| F5—C10 | 1.3404(17) |
| F6—C12 | 1.3358(17) |
| F7—C13 | 1.3482(17) |
| O1—C1 | 1.339(2) |
| O1—C2 | 1.418(2) |
| O2—C14 | 1.2463(18) |
| O2—H3 | 1.43(3) |
| O3—C19 | 1.3036(19) |
| O3—H3 | 1.03(3) |
| O4—C19 | 1.2274(19) |
| N1—C14 | 1.3454(19) |
| N1—C11 | 1.4133(19) |
| N1—H1 | 0.89(2) |
| C2—C3 | 1.382(2) |
| C2—C7 | 1.383(2) |
| C3—C4 | 1.387(3) |
| C3—H3A | 0.9500 |
| C4—C5 | 1.390(2) |
| C4—H4 | 0.9500 |
| C5—C6 | 1.396(2) |
| C5—H5 | 0.9500 |
| C6—C7 | 1.398(2) |
| C6—C8 | 1.485(2) |
| C7—H7 | 0.9500 |
| C8—C9 | 1.395(2) |
| C8—C13 | 1.396(2) |
| C9—C10 | 1.375(2) |
| C10—C11 | 1.389(2) |
| C11—C12 | 1.391(2) |
| C12—C13 | 1.383(2) |
| C14—C15 | 1.486(2) |
| C15—C18 | 1.396(2) |
| C15—C16 | 1.428(2) |
| C16—C17 | 1.360(2) |
| C16—H16 | 0.9500 |
| C17—H17 | 0.9500 |
| C18—C19 | 1.488(2) |
| C17—S1—C18 | 92.04(7) |
| C1—O1—C2 | 116.91(13) |
| C14—O2—H3 | 112.6(10) |
| C19—O3—H3 | 111.3(15) |
| C14—N1—C11 | 121.36(13) |
| C14—N1—H1 | 121.7(14) |
| C11—N1—H1 | 116.8(14) |
| F1—C1—F2 | 108.52(15) |
| F1—C1—F3 | 107.18(16) |
| F2—C1—F3 | 107.70(15) |
| F1—C1—O1 | 113.08(16) |
| F2—C1—O1 | 107.85(15) |
| F3—C1—O1 | 112.33(15) |
| C3—C2—C7 | 122.63(15) |
| C3—C2—O1 | 118.25(14) |
| C7—C2—O1 | 118.96(15) |
| C2—C3—C4 | 118.18(15) |
| C2—C3—H3A | 120.9 |
| C4—C3—H3A | 120.9 |
| C3—C4—C5 | 120.66(16) |

TABLE 7-continued

Bond lengths [Å] and angles [°] for PP-001 polymorph Form B

| | |
|---|---|
| C3—C4—H4 | 119.7 |
| C5—C4—H4 | 119.7 |
| C4—C5—C6 | 120.37(16) |
| C4—C5—H5 | 119.8 |
| C6—C5—H5 | 119.8 |
| C5—C6—C7 | 119.32(14) |
| C5—C6—C8 | 119.89(14) |
| C7—C6—C8 | 120.77(14) |
| C2—C7—C6 | 118.83(15) |
| C2—C7—H7 | 120.6 |
| C6—C7—H7 | 120.6 |
| C9—C8—C13 | 115.31(14) |
| C9—C8—C6 | 121.85(14) |
| C13—C8—C6 | 122.79(14) |
| F4—C9—C10 | 117.73(13) |
| F4—C9—C8 | 119.91(13) |
| C10—C9—C8 | 122.36(14) |
| F5—C10—C9 | 119.28(13) |
| F5—C10—C11 | 119.13(13) |
| C9—C10—C11 | 121.53(14) |
| C10—C11—C12 | 117.25(14) |
| C10—C11—N1 | 119.25(13) |
| C12—C11—N1 | 123.30(13) |
| F6—C12—C13 | 119.10(13) |
| F6—C12—C11 | 120.23(13) |
| C13—C12—C11 | 120.56(14) |
| F7—C13—C12 | 117.43(13) |
| F7—C13—C8 | 119.59(13) |
| C12—C13—C8 | 122.88(14) |
| O2—C14—N1 | 119.62(14) |
| O2—C14—C15 | 123.16(13) |
| N1—C14—C15 | 117.20(13) |
| C18—C15—C16 | 111.44(13) |
| C18—C15—C14 | 125.05(13) |
| C16—C15—C14 | 123.47(13) |
| C17—C16—C15 | 112.56(14) |
| C17—C16—H16 | 123.7 |
| C15—C16—H16 | 123.7 |
| C16—C17—S1 | 112.62(12) |
| C16—C17—H17 | 123.7 |
| S1—C17—H17 | 123.7 |
| C15—C18—C19 | 134.05(14) |
| C15—C18—S1 | 111.33(11) |
| C19—C18—S1 | 114.62(11) |
| O4—C19—O3 | 121.44(14) |
| O4—C19—C18 | 119.45(14) |
| O3—C19—C18 | 119.11(13) |

In some embodiments, the DSC, GVS, PLM, SEM, and IPLC characteristics of PP-001 Form B are discussed in more detail below in Example 5.

Methods of Making Polymorphs

In some embodiments, the disclosure provides for a method of making polymorph Form A. In some embodiments, the disclosure provides method of preparing polymorph Form A of PP-001, the method comprising: (a) obtaining a sample comprising 3-(2,3,5,6-tetrafluoro-3'-trifluoromethoxy-biphenyl-4-ylcarbamoyl)-thiophene-2-carboxylic acid; (b) dissolving the sample of (a) in a solvent comprising $C_1$-$C_5$ alcohol, $C_1$-$C_5$ ketone, or $C_1$-$C_5$ acetate solvent at 20° C. to 60° C. to form a solution; and (c) removing the solvent from the solution to obtain the polymorph Form A.

The disclosure provides that dissolving the PP-001 in a lower alkyl solvents such as $C_1$-$C_5$ alcohol, $C_1$-$C_5$ ketone, and $C_1$-$C_5$ acetate before removal of the solvent and crystallization results in formation of polymorph Form A. As used herein the terms "$C_1$-$C_5$ alcohol", "$C_1$-$C_5$ ketone", and $C_1$-$C_5$ acetate refer to any alcohol, ketone, or acetate, respectively, comprised of 1 to 5 carbon atoms. In some embodiments, the $C_1$-$C_5$ alkyl is a linear or branched carbon chain. In some embodiments, the $C_1$-$C_5$ alcohol is methanol, ethanol, 1-propanol, isopropanol, 1-butanol, 2-butanol, 1-pentanol, 2-pentanol, isopentanol, or combinations thereof. In some embodiments, the $C_1$-$C_5$ ketone is selected from methyl ethyl ketone (MEK), methylisobutyl ketone (MIBK), or acetone. In some embodiments, the $C_1$-$C_5$ acetate is selected from methyl acetate, ethyl acetate, propyl acetate, butyl acetate, or pentyl acetate.

In some embodiments, the PP-001 is dissolved in a solvent to form a solution, wherein the solution is greater than 80% $C_1$-$C_5$ alcohol, $C_1$-$C_5$ ketone, or $C_1$-$C_5$ acetate, greater than 85% $C_1$-$C_5$ alcohol, $C_1$-$C_5$ ketone, or $C_1$-$C_5$ acetate, greater than 90% $C_1$-$C_5$ alcohol, $C_1$-$C_5$ ketone, or $C_1$-$C_5$ acetate, greater than 95% $C_1$-$C_5$ alcohol, $C_1$-$C_5$ ketone, or $C_1$-$C_5$ acetate, greater than 98% $C_1$-$C_5$ alcohol, $C_1$-$C_5$ ketone, or $C_1$-$C_5$ acetate or greater than 99% $C_1$-$C_5$ alcohol, $C_1$-$C_5$ ketone, or $C_1$-$C_5$ acetate.

In some embodiments, the PP-001 is dissolved in a solvent to form a solution, wherein the solution is greater than 80% $C_1$-$C_5$ alcohol, greater than 85% $C_1$-$C_5$ alcohol, greater than 90% $C_1$-$C_5$ alcohol, greater than 95% $C_1$-$C_5$ alcohol, than 98% $C_1$-$C_5$ alcohol, or greater than 99% $C_1$-$C_5$ alcohol.

In some embodiments, the PP-001 is dissolved in a solvent to form a solution, wherein the solution is greater than 80% $C_1$-$C_5$ ketone, greater than 85% $C_1$-$C_5$ ketone, greater than 90% $C_1$-$C_5$ ketone, greater than 95% $C_1$-$C_5$ ketone, than 98% $C_1$-$C_5$ ketone, or greater than 99% $C_1$-$C_5$ ketone.

In some embodiments, the PP-001 is dissolved in a solvent to form a solution, wherein the solution is greater than 80% $C_1$-$C_5$ acetate, greater than 85% $C_1$-$C_5$ acetate, greater than 90% $C_1$-$C_5$ acetate, greater than 95% $C_1$-$C_5$ acetate, than 98% $C_1$-$C_5$ acetate, or greater than 99% $C_1$-$C_5$ acetate.

In some embodiments, PP-001 forms crystals, e.g., polymorph Form A, using a solvent with little or no water. In some embodiments, the PP-001 is dissolved in a solvent to form a solution, wherein the solution comprises less than 20% water, less than 15% water, less than 10% water, less than 5% water, or less than 2% water (vol/vol). In some embodiments, the PP-001 is dissolved in a solvent to form a solution, wherein the solution comprises 0% to 20% water, 0% to 10% water, 0% to 5% water or 0% to 2% water. In some embodiments, the PP-001 is dissolved in a solvent to form a solution, wherein the solution comprises 0% to 1% water. In some embodiments, the PP-001 is dissolved in a solvent to form a solution, wherein the solvent is an anhydrous solvent.

In some embodiments, PP-001 forms crystals, e.g., polymorph Form A, comprising a solvent and a small amount of water, e.g., about 1% to about 15%, about 1% to about 10%, about 1% to about 5% water. In some embodiments, PP-001 forms crystals, e.g., polymorph Form A, comprising a solvent and a small amount of water, e.g., about 1% to about 15%, about 1% to about 10%, about 1% to about 5% water.

In some embodiments, PP-001 forms crystals, e.g., polymorph Form A, comprising a $C_1$-$C_5$ alcohol and a small amount of water, e.g., about 1% to about 15%, about 1% to about 10%, about 1% to about 5% water. In some embodiments, PP-001 forms crystals, e.g., polymorph Form A, comprising a $C_1$-$C_5$ ketone and a small amount of water, e.g., about 1% to about 15%, about 1% to about 10%, about 1% to about 5% water. In some embodiments, PP-001 forms crystals, e.g., polymorph Form A, comprising a $C_1$-$C_5$ acetate and a small amount of water, e.g., about 1% to about 15%, about 1% to about 10%, about 1% to about 5% water.

The temperature used to dissolve the PP-001 in the solvent can be determined by the skilled artisan and can be dependent on the concentration of the PP-001 in the solvent as well as the temperature in which the dissolving occurs and the duration of the dissolving.

In some embodiments, the PP-001 is dissolved in a solvent at 20° C. to 60° C. to form a solution. In some embodiments, this can be referred to as a "dissolving temperature." In some embodiments, the PP-001 is dissolved in a solvent at 25° C., 30° C., 35° C., 40° C., 45° C., or 50° C. to 60° C. to form a solution. In some embodiments, the PP-001 is dissolved in a solvent at 25° C. to 30° C., 30° C. to 35° C., 35° C. to 40° C., 40° C. to 45° C., or 45° C. to 5° C., or 50° C. 60° C. to form a solution.

In some embodiments, the PP-001 dissolved in the solution is less than 10% (wt/vol), less than 5% (wt/vol), less than 2% (wt/vol), less than 1% (wt/vol), less than 0.5% (wt/vol) or less than 0.1% (wt/vol) of the solvent. In some embodiments, the concentration of PP-001 is less than the saturation point for a given solvent and temperature, e.g., if the saturation point of PP-001 for a given solvent and temperature is "X mg/mL", then the concentration of PP-001 is less than "X mg/mL", e.g., 20% less, 50% less, or 80% less.

In some embodiments, the PP-001 dissolved in the solvent forms a solution, wherein the solution is cooled to an incubation temperature. In some embodiments, the incubation temperature is held for a "period of time." In some embodiments, the period of time is greater than 1 hour, greater than 2 hours, greater than 3 hours, greater than 4 hours, greater than 5 hours, greater than 6 hours, greater than 8 hours, greater than 10 hours, greater than 12 hours, greater than 15 hours, greater than 20 hours, greater than 24 hours, greater than 2 days, or greater than 3 days. In some embodiments, the period of time for the incubation temperature is about 1 hours to about 48 hours, about 2 hours to about 36 hours, about 3 hours to about 24 hours, about 4 hours to about 20 hours, or about 6 hours to about 18 hours.

In some embodiments, the incubation temperature is about 1° C. to about 10° C. for a period of time. In some embodiments, the incubation temperature is about 2° C. to about 8° C., about 3° C. to about 7° C., or about 4° C. to about 6° C. for a period of time.

In some embodiments, the change of temperature from the dissolving temperature to the incubation temperature can be done over a defined time period, i.e., a rate of change or temperature over the given time. In some embodiments, the cooling from the dissolving temperature to the incubation temperature is at a rate of about 0.02° C./min to about 1° C./min until the incubation temperature is reached. In some embodiments, the cooling to the incubation temperature is at a rate of about 0.05° C./min to about 0.5° C./min until the incubation temperature is reached. In some embodiments, the cooling to the incubation temperature is at a rate of about 0.1° C./min to about 0.3° C./min until the incubation temperature is reached.

In some embodiments, after the incubation temperature is held for a period of time, the solvent is then removed and the PP-001 crystalizes. In some embodiments, the crystallization process can be initiated using seed crystals or other initiating composition. In some embodiments, the solvent is removed and the polymorphs form over a specified time, i.e., the removal time. One of skill in the art will appreciate that as the concentration of solvent is decreased, the concentration of PP-001 will increase until the crystallization process initiates. The skilled artisan will also appreciate that a number of factors may affect the removal time, e.g., the amount of solvent to be removed, the type of solvent being removed, the temperature, the pressure, etc., will affect the removal time of the solvent.

In some embodiments, the removal time is greater than 10 minutes, greater than 20 minutes, greater than 30 minutes, greater than 45 minutes, greater than 1 hour, greater than 2 hours, greater than 3 hours, greater than 4 hours, greater than 6 hours, greater than 9 hours, greater than 12 hours, greater than 15 hours, greater than 18 hours, greater than 21 hours or greater than 24 hours. In some embodiments, the removal time is greater than 1 day, 2 days, 3 days, 4 days, 5 days or 6 days.

In some embodiments, the solvent is removed by evaporation. The skilled artisan will appreciate that the rate of evaporation will be determined by a number of factors, including, but not limited to the identity of the solvent, the temperature, the pressure, etc. In some embodiments, the evaporation is performed at the incubation temperature. In some embodiments, the evaporation temperature can vary, e.g., can vary over time. In some embodiments, the evaporation temperature is constant. In some embodiments, the evaporation is performed at a temperature greater than the incubation temperature. In some embodiments, the evaporation is performed at greater than 5° C., greater than 10° C., greater than 15° C., greater than 20° C., greater than 25° C., or greater than 30° C. In some embodiments, the evaporation is performed at 5° C. to 40° C., 10° C. to 35° C., 15° C. to 30° C. In some embodiments, the evaporation is performed at about 20° C. to about 35° C. In some embodiments, if more than one solvent is present, the evaporation temperature can be maintained at a first temperature until the first solvent is evaporated, and then changed to a second temperature.

In some embodiments, the evaporation can be performed at various temperatures. In some embodiments, the evaporation is performed at 1 atmosphere pressure. In some embodiments, the evaporation is performed at less than 1 atmosphere pressure.

In some embodiments, the removing of the solvent is performed by filtration. For example, in some embodiments, the solvent is removed using a membrane or semi-permeable membrane. In some embodiments, when using the semi-permeable membrane, the solvent is replaced by a different solvent, wherein the PP-001 forms crystals in the different solvent.

In some embodiments, the solvent is removed by lyophilization.

Pharmaceutical Compositions

The present disclosure provides for pharmaceutical compositions comprising the polymorphs of PP-001 described herein, e.g., Form A or Form B. In some embodiments, the disclosure provides for a pharmaceutical composition comprising the polymorphs Form A of PP-001 and a pharmaceutically acceptable excipient, carrier, or diluent.

In some embodiments, the term "pharmaceutically acceptable" excipient, carrier, diluent, or ingredient refers to a substance that is suitable for use in humans and/or animals without excessive adverse side effects (such as toxicity, irritation, and allergies), that is, with a reasonable benefit/risk ratio.

In some embodiments, the pharmaceutical compositions as described herein can comprise other therapeutically active substances.

In some embodiments, the pharmaceutical composition of the present invention is formulated for parenteral administration, including formulated for intravenous, intra-arterial, intramuscular subcutaneous, intraperitoneal, intravitreal, and transdermal administration. In some embodiments, the pharmaceutical composition of the present invention is formulated for topical, oral, sublingual, enteral, nasal, buccal, or inhalation administration.

In some embodiments, the pharmaceutical composition comprising a polymorph of the invention is formulated in the form of a pill, tablet, capsule, suppository, syrup, lozenge, eyedrop, or liquid formulation. Formulations for pills, tablets, and hard gelatin capsules can comprise excipients known to the skilled artisan.

In some embodiments, the disclosure provides a method of preparing a pharmaceutical composition, the method comprising combining polymorph Form A of PP-001 with one or more pharmaceutically acceptable excipients, diluents, or carriers.

In some embodiments, the disclosure provides a kit comprising polymorph Form A (or Form B) of PP-001 and a container. In some embodiments, the container is a vial, packet, sachet, pre-filled syringe, ampule, or capsule.

Methods of Treatment

In some embodiments, the pharmaceutical composition is As used herein, the term "effective amount" refers to an amount of a therapeutic agent to treat, alleviate or prevent a target disease or condition, or an amount that exhibits a detectable therapeutic or preventive effect. The exact effective amount for a subject depends on the subject's size and health, the nature and extent of the condition, and the chosen therapeutic agent and/or combination of therapeutic agents. Therefore, it is not useful to specify an accurate effective amount in advance. However, for a given condition, a routine experiment can be used to determine the effective amount, which can be judged by the clinician.

The present disclosure provides a method of treating, preventing, or ameliorating a disease or condition in a subject in need thereof comprising administering to the subject a pharmaceutically effective amount of polymorph Form A of PP-001.

In some embodiments, the disease, disorder, or condition is one which benefits from inhibition or reduction of activity of DHODH.

In some embodiments, the disease, disorder, or condition is an inflammatory disease or disorder or condition, an acute immunological disease, disorder, or condition, an autoimmune disease, disorder, or condition, a disease, disorder, or condition caused by abnormal or malignant cell proliferation, or an infectious disease, disorder, or condition.

In some embodiments, the disease, disorder, or condition includes, but it not limited to, fibrosis, uveitis, rhinitis, asthma or arthropathy, in particular, arthrosis, all forms of rheumatism acute immunological events and disorders such as sepsis, septic shock, endotoxic shock, Gram-negative sepsis, toxic shock syndrome, acute respiratory distress syndrome, stroke, reperfusion injury, CNS injury, allergic conditions, graft versus host and host versus graft disorders, Alzheimer's disease, pyresis, restenosis, chronic pulmonary inflammatory disease, silicosis, pulmonary sarcosis, bone resorption disease. These immunological events also include a desired modulation and suppression of the immune system; all types of autoimmune diseases, in particular rheumatoid arthritis, rheumatoid spondylitis, osteoarthritis, gouty arthritis, multiple sclerosis, insulin dependent diabetes mellitus and non-insulin dependent diabetes, and systemic lupus erythematosus, lupus nephritis, ulcerative colitis, Crohn's disease, inflammatory bowel disease, as well as other chronic inflammations, chronic diarrhea; dermatological disorders such as psoriasis, progressive retinal atrophy, and all kinds of infections, including opportunistic infections.

In some embodiments, the disease, disorder, or condition is a malignant cell proliferation, such as all forms of hematological and solid cancers. Therefore the polymorphs according to the invention and compositions prepared therewith are generally useful for regulating cell activation, cell proliferation, cell survival, cell differentiation, cell cycle, cell maturation and cell death or to induce systemic changes in metabolism such as changes in sugar, lipid or protein metabolism. They can also be used to support cell generation poiesis, including blood cell growth and generation (prohematopoietic effects) after depletion or destruction of cells, as caused by, for example, toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis.

In some embodiments, the polymorphs of PP-001 used in the treatments as described herein can be prophylactic or curative. In the described treatments, the polymorphs and compositions of the present invention can be administered in combination with other therapeutic agents.

In some embodiments, the dose used in treatment dose can vary within wide limits and is to be suited to the individual conditions in each individual case. For the above uses the appropriate dosage will vary depending on the mode of administration, the particular condition to be treated and the effect desired.

EXAMPLES

Example 1—Properties of PP-001

The general tested characteristics of 3-(2,3,5,6-tetrafluoro-3'-trifluoromethoxy-biphenyl-4-ylcarbamoyl)-thiophene-2-carboxylic acid (PP-001) are shown below in Table 8.

TABLE 8

Characteristics of PP-001.

| | |
|---|---|
| Molecular Weight | 479.32 |
| pKa | 2.23 |
| LogP (measured) | 4.19 |
| Solubility in 50 mM phosphate Buffer | 1.4 µg/ml (pH 4)<br>854 µg/ml (pH 7.4)<br>833 µg/ml (pH 9) |
| Stability | Stable for >16 h at pH 2 (HCl), pH 7.4 (trisbuffer), pH 8.5 (tris buffer).<br>Stable for >6 h in artificial gastric juice, simulated intestinal fluid, human plasma and PBS pH 7.4. |
| Purity | 99.4% (HPLC-UV)<br>99.7% ($^1$H-NMR) |
| Melting Point | 216° C. |
| Solvent Content/hygroscopicity | Not tested |
| Oral bioavailability | 15%-30% (depending on formulation used) |

Example 2—Crystallization of PP-001 from Amorphous PP-001

Preparation and solubility of amorphous PP-001. PP-001 was treated with increasing aliquots of solvent until a maximum of 60 vol (1800 µl) was added in a HPLC vial.

Figure 2C:
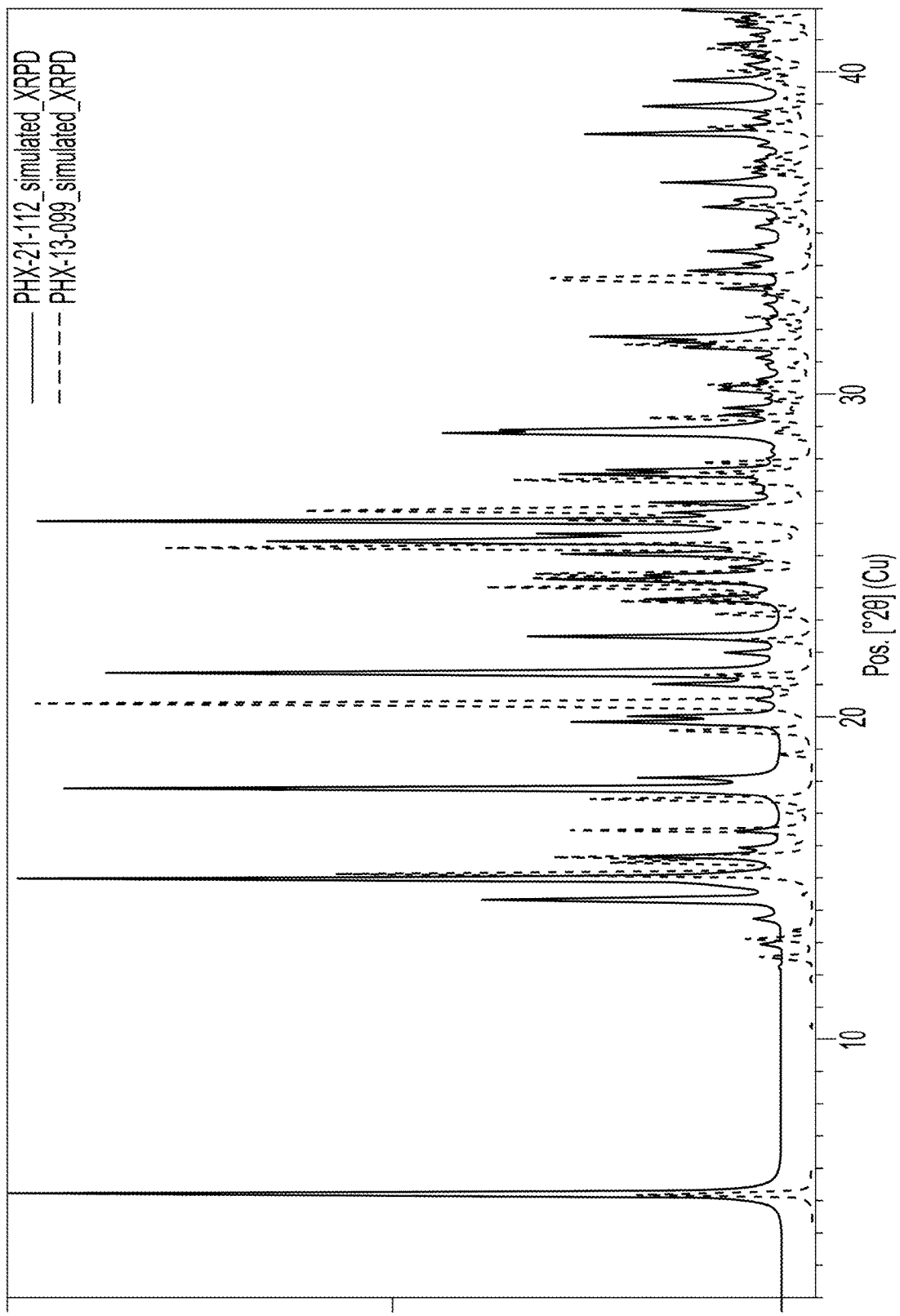
Figure 2D:
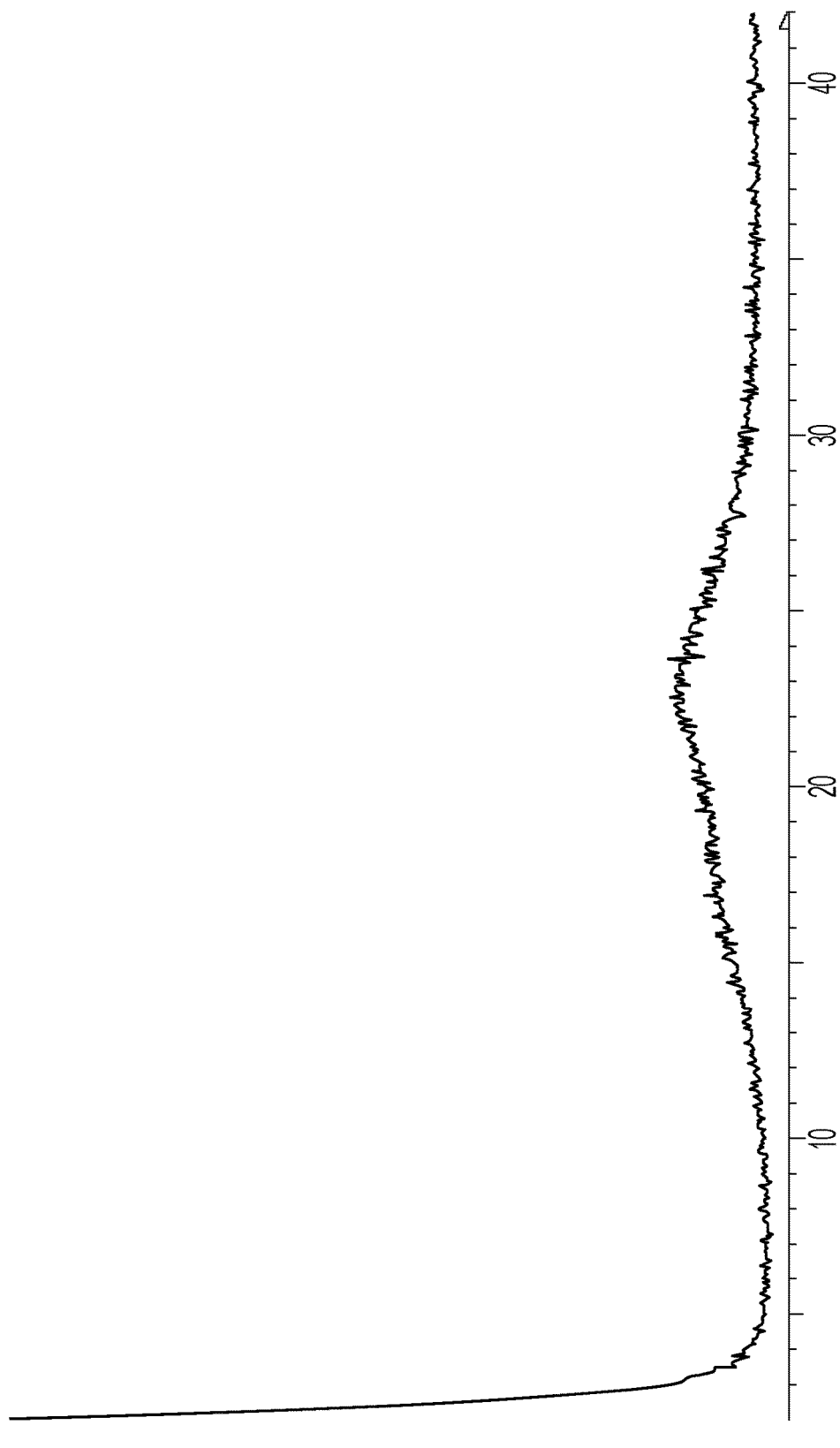

Samples that formed solutions were positive pressure filtered using a PTFE syringe filter to remove any remaining solid particulates. The solutions were then flash frozen in a dry ice/acetone bath and lyophilized overnight to remove the solvent. Solids isolated post-lyophilization were analyzed by XRPD and characterized. The XRPD profile on amorphous PP-001 is shown in FIG. 2C.

The remaining suspensions were subjected to maturation cycling between 25° C. and 50° C. (4 hours per cycle) or held isothermally at RT overnight. Samples were isolated under positive pressure and analyzed by XRPD.

The results from the solvent assessment for lyophilization are shown in FIG. 5.

As can be seen in FIG. 5, PP-001 was shown to be soluble in THF:water (70:30) and 1,4-dioxane. All other solvents and solvent mixtures tested formed opaque solutions or suspensions unsuitable for lyophilization. These suspensions were subjected to maturation cycling from 25° C. to 50° C. (4 hours per cycle) or maturation at RT overnight. The suspended solids were subsequently isolated, and the wet cakes were analyzed by XRPD. For ACN/water (1:1), DCM and t-BuOH/water Form A was obtained. For pure t-BuOH, a solution was achieved after maturation cycling. This was subjected to slow evaporation, which resulted in Form B.

For the crystallization of amorphous PP-001, P-001 (3.0 g) was treated with 20 vol (60 ml) of THF:water (70:30) and stirred at RT until a clear solution was obtained. The solution was positive pressure filtered using a PTFE syringe filter to remove any remaining solid particulates. The solution was then aliquoted (600 μl/vial) into individual HPLC vials. The HPLC vials were then flash frozen in a dry ice/acetone bath and lyophilized overnight to remove the solvent leaving a white powdery solid (ca. 30 mg/vial). A vial representing the batch was then analyzed by XRPD to confirm the material to be amorphous post-lyophilization. Samples were stored at −20° C. when not in use. Samples were used in subsequent polymorphism studies as needed.

Crystallization methods. The following isothermal maturation techniques as well as maturation cycling between RT and 50° C. were used to generate crystalline material which was analyzed by XRPD. A further, antisolvent addition screen was also conducted.

Preparation of Amorphous Material

PP-001 (3.0 g) was treated with 20 vol (60 ml) of THF:water (70:30) and stirred at RT until a clear solution was obtained. The solution was positive pressure filtered using a PTFE syringe filter to remove any remaining solid particulates. The solution was then aliquoted (600 μl/vial) into individual HPLC vials. The HPLC vials were then flash frozen in a dry ice/acetone bath and lyophilized overnight to remove the solvent leaving a white powdery solid (ca. 30 mg/vial). A vial representing the batch was then analyzed by XRPD to confirm the material to be amorphous post-lyophilization. Samples were stored at −20° C. when not in use. Samples were used in subsequent polymorphism studies as needed.

Polymorph Screening Procedure 2 (5° C. Isothermal Maturation)

Amorphous PP-001 (ca. 30 mg, batch #2) was treated with aliquots of solvent to a maximum of 15 vol (450 μl) at 5° C., 300 rpm, while maintaining a suspension. Observations were then recorded. Samples were matured at 5° C. for 24 hours. Further observations were taken, and samples were treated as follows:

For suspensions, an aliquot was taken (ca. 30 μl) and subjected to XRPD analysis while still wet. For any new patterns the samples were reanalyzed after drying at RT.

Samples that formed a solution were subjected to up to 10 volumes (1500 μl) of antisolvent at RT.

Solids showing any new patterns were subsequently extracted using an SPE cartridge and frit under positive pressure filtration. The samples were allowed to dry under ambient conditions at least overnight before further characterization was performed.

The results from the maturation of amorphous material at 5 C are shown in FIGS. 6A and 6B.

For maturation at 5° C., most solvents maintained a suspension. DMSO froze at 5° C. as expected. This sample was heated back to 25° C. and excess ACN was added as an antisolvent to try to encourage precipitation. However, the sample remained a solution and was not investigated further. 1,4-Dioxane partially froze, but a moving slurry was maintained. For THF:water (50%), a gummy solid formed on addition of the solvent. All samples were analyzed wet, to try to capture any possible metastable solvate forms. However, on analysis the vast majority of material obtained was either Form A or Form B. (See FIGS. 6A and 6B).

Figure 7:
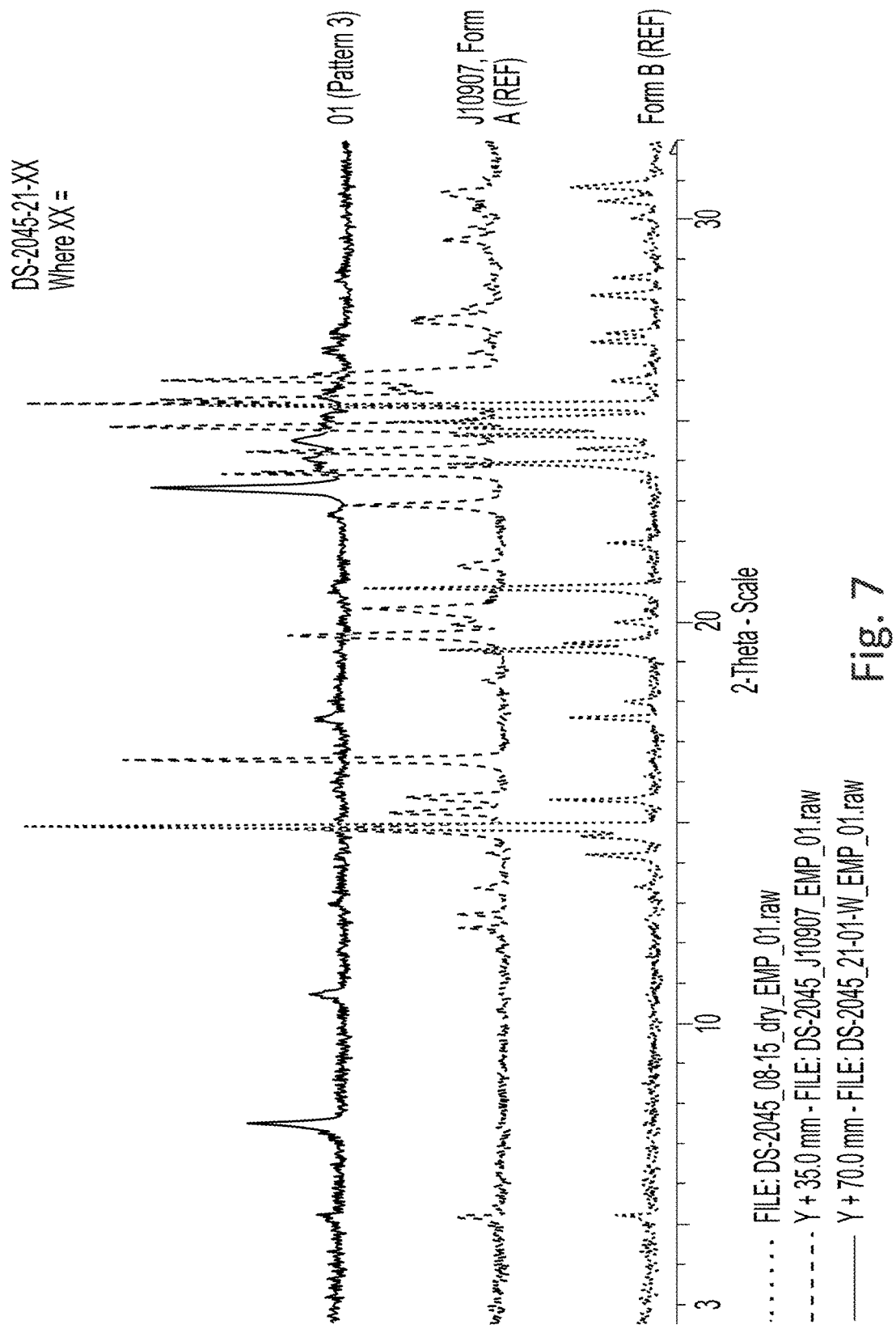
FIG. 7 shows an overlay of XPRD profiles for PP-001 Form A and Form B, and "Pattern 3", which was obtained by maturation of amorphous PP-001 at 5° C. using heptane.

Form A was obtained from ethyl acetate, MIBK, IPA, MEK, 1-propanol, acetone, EtOH, ACN, MeOH, water, MeOH:water (3%) and (5%), EtOH:water (5%), acetone:water (5%) and (10%) as well as THF:water (50%). Form B was obtained from diethyl ether, propyl acetate, isopropyl acetate, TBME, 1,4-dioxane, toluene, chloroform, THF:heptane (1:1) as well as the current process solvent, IPA:water (at 5% and 25% water). One additional novel pattern was obtained from heptane, denoted Pattern 3 (FIG. 7).

Polymorph Screening Procedure 3 (Temperature Cycling)

Amorphous PP-001 (ca. 30 mg, Batch #2) was treated with aliquots of solvent to a maximum of 20 vol (600 μl) at 25° C., 300 rpm, while maintaining a suspension. Observations were then recorded. Samples were then subjected to maturation cycling between RT and 50° C. (4 hours per cycle) for 24 hours. Further observations were taken and samples were treated as follows:

For suspensions, an aliquot was taken (ca. 30 μl) and subjected to XRPD analysis while still wet. For any new patterns, the samples were reanalyzed after drying at RT.

Samples that formed a solution were subjected to up to 1 volume equiv. (150 μl) of antisolvent at RT.

Solids showing any new patterns were subsequently extracted using an SPE cartridge and frit under positive pressure filtration. The samples were allowed to dry under ambient conditions at least overnight before further characterization was performed.

The results of the maturation cycling of amorphous material is shown in FIGS. 8A and 8B.

As was the case for the maturation at 5° C., most solvents maintained a suspension. Diethyl ether was not run due to the experiment temperature exceeding the solvent boiling point. A solution was obtained from acetone:water (5%) after maturation, but additional water (150 ul) was added to achieve a suspension. Volatile solvents (acetone and ethyl acetate) resulted in clear solutions with solid material building up above the solvent line. This material was resuspended periodically using a spatula until the screen was complete. Form B was obtained from n-heptane, TBME, toluene chloroform. Form B was also obtained from acetone:water (5%) after antisolvent addition.

The remaining suspensions all gave Form A. Interestingly, while Form B was obtained from acetone:water (5%) after antisolvent addition (final ratio ca. acetone:water 1:1), acetone:water (10%) gave Form A. This was also in contrast to the previous screen, where both acetone:water 5% and 10% gave Form A. The result is potentially driven by kinetics, where rapid nucleation (i.e. by fast antisolvent addition) favors Form B. This was investigated further in subsequent screens. No other patterns were obtained from this screen. The current process solvent (IPA:water) was shown to give Form A after maturation.

Polymorph Screening Procedure 4 (50° C. Isothermal Maturation)

Amorphous PP-001 (ca. 30 mg, Batch #2) was treated with aliquots of solvent to a maximum of 15 vol (450 l) at 50° C., 300 rpm, while maintaining a suspension. Observations were then recorded. Samples were matured at 50° C. for 24 hours. Further observations were taken, and samples were treated as follows:

For suspensions, an aliquot was taken (ca. 30 µl) and subjected to XRPD analysis while still wet. For any new patterns the samples was reanalyzed after drying at RT.

Samples that formed a solution were subjected to up to 3 volumes (450 µl) of antisolvent at 50° C.

Solids showing any new patterns were subsequently extracted using an SPE cartridge and frit under positive pressure filtration. The samples were allowed to dry under ambient conditions at least overnight before further characterization was performed.

The results from the maturation of amorphous material at 50 C are shown in FIGS. 9A and 9B.

As with the maturation cycling screen, diethyl ether was not run due to the experiment temperature exceeding the solvent boiling point. A suspension was maintained in the majority of the solvents tested. From suspensions, Form B was obtained from n-heptane, TBME, toluene and isopropyl acetate. On extraction of isopropyl acetate however, this transitioned to Form A. All other suspensions gave Form A. A solution was obtained from only acetone:water (5%). Ca. 150 µl of water was added at 50° C. to achieve a suspension. A sample was immediately taken and analyzed by XRPD, matching the XRPD pattern for Form B. The sample was then left for isothermal maturation with the other samples. After maturation, the sample was analyzed again and was shown to have transitioned to Form A. This result was in agreement with the previous screen, where nucleation of Form B can be transitioned to Form A with maturation.

Acetone:water (10%) was initially opaque, however after several days maturation, a solution was obtained. This sample was removed from the heat source and subjected to ACN as an antisolvent to precipitate at RT, resulting in the isolation of Form A. The current process solvent (IPA:water 13:5) was shown to give Form A after maturation.

Polymorph Screening Procedure 5 (Antisolvent Addition)

PP-001 (ca. 30 mg, Batch #1) was treated with aliquots of solvent at RT, with stirring, until a solution was obtained, or a maximum of 80 vol (2.4 ml) was reached. Observations were then recorded. If samples did not dissolve at RT, suspensions were heated up to 50° C. to facilitate dissolution. All solutions were subjected to antisolvent addition (up to 5 v/v equivalents) to facilitate precipitation at temperature.

For suspensions, an aliquot was taken for XRPD analysis on precipitation of the material. The suspension was then left to mature at temperature overnight. A second aliquot was then for XRPD analysis.

Solutions were cooled from 25 to 5° C. at 0.1° C./min and held at 5° C. overnight. Any remaining solution were subjected to evaporation at RT.

Suspensions were subsequently extracted using an SPE cartridge and frit under positive pressure filtration. A sample of the wet cake was taken for analysis. The samples were then allowed to dry under ambient conditions at least overnight before re-analysis by XRPD The results from the antisolvent addition polymorph screen are shown in FIG. 10.

Water, heptane and toluene were targeted as antisolvents and a selection of solvents were used to dissolve PP-001. In some cases, dissolution was only achieved at heightened temperatures. Once dissolution was achieved, the antisolvent was added in up to 5 volume equivalents. Suspensions were achieved in all water samples and most heptane samples, suggesting these two to be the most effective antisolvents. Aliquots were taken from all suspensions within 1 hour of antisolvent addition, followed by a 2nd aliquot taken after maturation for 24 hours. It was difficult to observe diffraction from the aliquots (due to a dilution effect, as high solvent volumes were used).

For those samples where diffraction was sufficiently visible, it was observed that Form B was present in all samples. After maturation, a transition to Form A was observed in all samples, with the exception of THF/heptane. This result again supports the thought that the formation of Form B may be driven kinetically. Careful control of supersaturation during any crystallization process is therefore recommended. On isolation of the materials, Form B was obtained from IPA/water, ethyl acetate/heptane and THF/heptane. The remaining suspensions gave Form A. Samples subjected to toluene as an antisolvent did not precipitate. IPA/heptane also did not precipitate. These samples were cooled to 5° C. overnight to try to encourage nucleation but remained solutions. As such, the samples were instead subjected to slow evaporation. In all cases, Form B was obtained.

Summary of the Crystal Polymorph Screens

In most cases, the polymorphism screen using amorphous PP-001 resulted in isolation of crystalline material. In particular, the formation of Form A and Pattern B were most prevalent. An additional unique XRPD pattern was obtained from heptane at 5° C. The conditions across all polymorphism screen (with the exception of antisolvent addition) experiments used to produce each pattern are summarized in Table 9.

TABLE 9

Overview of materials from polymorph screening using amorphous input material.

| | Conditions | | | |
|---|---|---|---|---|
| Solvent | 5° C. | 25/50° C. | 50° C. | Evaporation |
| n-Heptane | Pattern 3 | Form B | Form B | N/A |
| Diethyl ether | Form B | N/A | N/A | N/A |
| Propyl acetate | Form B | Form A | Form A | Form A |
| Ethyl acetate | Form A | Form A | Form A | Form A |
| Isopropyl acetate | Form B | Form A | Form B to Form A | Form B |
| MIBK | Form A | Form A | Form A | Form A |
| 2-Propanol | Form A | Form A | Form A | Form A |
| MEK | Form A | Form A | Form A | Form A |
| 1-Propanol | Form A | Form A | Form A | Form A |
| Acetone | Form A | Form A | Form A | N/A |
| Ethanol | Form A | Form A | Form A | Form A |
| Dimethyl sulfoxide | N/A | N/A | N/A | N/A |
| Acetonitrile | Form A | Form A | Form A | N/A |

TABLE 9-continued

Overview of materials from polymorph screening using amorphous input material.

| Solvent | Conditions | | | |
|---|---|---|---|---|
| | 5° C. | 25/50° C. | 50° C. | Evaporation |
| TBME | Form B | Form B | Form B | Form B |
| 1,4-Dioxane | Form B | N/A | N/A | Form B |
| Toluene | Form B | Form B | Form B | N/A |
| Chloroform | Form B | Form B | Form A | N/A |
| Tetrahydrofuran | N/A | N/A | N/A | Form B |
| Methanol | Form A | Form A | Form A | Form A |
| Water | Form A (WD) | Form A | Form A | N/A |
| Methanol:water (3%) | Form A | Form A | Form A | N/A |
| Methanol:water (5%) | Form A | Form A | Form A | N/A |
| Ethanol:water (5%) | Form A | Form A | Form A | Form A |
| IPA:Water (5%) | Form B | Form A | Form A | Form A |
| Acetone:Water (5%) | Form A | N/A | Form B to Form A* | Form A |
| Acetone:Water (10%) | Form A | Form A | N/A | Form A + Form B |
| IPA:Water (25%) | Form B | Form A | N/A | N/A |
| THF:Water (10%) | N/A | N/A | Form A | Form B |
| DMSO/Water (1:1) | N/A | Form A | Form A | N/A |
| 1,4-Dioxane/Heptane (1:1) | N/A | Form A | Form A | N/A |
| THF/Heptane (1:1) | Form B | Form A | Form A | N/A |
| IPA:Water (13:5) | N/A | N/A | Form A | N/A |
| THF:Water (50%) | Form A | Form A | Form A | N/A |

Key: WD = Weak Diffraction
*= initial formation of Form B observed after antisolvent addition, subsequently transition to Form A on maturation As can be seen from Table 9, Form A was the most prevalent pattern overall, with Form B increasing in prevalence at lower temperatures. Solvents: heptane, TBME, toluene & chloroform show a preference for Form B at higher temperatures as well. At 5° C. heptane gives the novel Pattern 3. Note that the current process solvent, IPA/water, has also shown a preference for Form B at low temperatures but Form A at high temperatures. In addition, some samples were initially characterized as Form B, but subsequently transitioned to Form A on additional maturation. This was particularly noted to be the base for antisolvent crystallization.

For antisolvent addition, a transition from Form B to Form A was observed in several solvent/antisolvent mixtures. This result supports the thought that the formation of Form B may be driven kinetically.

Example 3—X-Ray Powder Diffraction

The following methods were used for XRPD.

X-Ray Powder Diffraction. The identification of Form A and Form B in a given sample was determined by analysis of samples using X-Ray Powder Diffraction (XRPD). The XRPD diffraction profiles for PP-001 Form A and Form B are shown in FIGS. 2A and 2B, respectively, and are discussed in more detail below. The studies utilized the following XRPD protocols:

1. Bruker AXS C2 GADDS

XRPD diffractograms were collected on a Bruker AXS C2 GADDS diffractometer using Cu Kα radiation (40 kV, 40 mA), an automated XYZ stage, a laser video microscope for auto-sample positioning and a Vántec-500 2-dimensional area detector. X-ray optics consists of a single Gobel multilayer mirror coupled with a pinhole collimator of 0.3 mm.

The beam divergence, i.e. the effective size of the X-ray beam on the sample, was approximately 4 mm. A θ-θ continuous scan mode was employed with a sample-detector distance of 20 cm which gives an effective 2θ range of 1.5°-32.5°. Typically, the sample was exposed to the X-ray beam for 120 seconds. The software used for data collection and analysis was GADDS for Win7/XP and Diffrac Plus EVA respectively.

Non-ambient conditions. For variable temperature (VT-XRPD) experiments samples were mounted on an Anton Paar DHS 900 hot stage at ambient conditions. The sample was then heated to the appropriate temperature at 20° C./min and subsequently held isothermally for 1 minute before data collection. Samples were prepared and analyzed on a silicon wafer mounted to the hot stage using a heat-conducting paste.

2. Bruker AXS D8 Advance

XRPD diffractograms were collected on a Bruker D8 diffractometer using Cu Kα radiation (40 kV, 40 mA) and a θ-2θ goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively.

Samples were run under ambient conditions as flat plate specimens using powder as received. The sample was prepared on a polished, zero-background (510) silicon wafer by gently pressing onto the flat surface or packed into a cut cavity. The sample was rotated in its own plane.

The details of the standard Pharmorphix data collection method are:

Angular range: 2 to 42° 2θ
Step size: 0.05° 2θ
Collection time: 0.5 s/step (total collection time: 6:40 min.

3. PANalytic Empyrean

XRPD diffractograms were collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel3D detector, placed on the diffracted beam, was fitted with a receiving slit and 0.04 rad Soller slits. The software used for data collection was X'Pert Data Collector using X'Pert Operator Interface. The data were analyzed and presented using Diffrac Plus EVA or HighScore Plus.

Samples were prepared and analyzed in either a metal or Millipore 96 well-plate in transmission mode. X-ray transparent film was used between the metal sheets on the metal well-plate and powders (approximately 1-2 mg) were used as received. The Millipore plate was used to isolate and analyze solids from suspensions by adding a small amount of suspension directly to the plate before filtration under a light vacuum.

The scan mode for the metal plate used the gonio scan axis, whereas a 2θ scan was utilized for the Millipore plate.

The details of the standard screening data collection method are:

Angular range: 2° to 32° 2θ
Step size: 0.0130° 2θ
Collection time: 12.75 s/step (total collection time of 2.07 min)

Non-ambient conditions. For variable temperature (VT-XRPD) experiments the samples were prepared and analyzed in an Anton Paar chromed sample holder with silicon wafer insert. A heating/cooling rate of 10° C./min was used with a 2 min isothermal hold before the measurement started. The measurement parameters are as per the standard screening data collection method (detailed above). Measurements were taken at the following temperatures: 25, 170, 180, 190, 200 on heating and 170, 140 and 25° C. on cooling. This cycle was repeated once.

Example 4. Solubility of PP-001 and XRPD

PP-001 (ca. 20 mg, Batch #1) was treated with increasing aliquots of solvent until either a clear solution or maximum of 80 vol (1600 l) of solvent was added. Samples were left for ~3 minutes at 25° C., 300 rpm, after each solvent addition before observations were recorded. Where possible, samples were heated to 50° C. and further observations were taken. Solutions at 25 or 50° C. were cooled to 5° C. at 0.1° C./min, 300 rpm and held overnight. Any suspensions at 50° C. were subjected to maturation cycling between RT/50° C. (4 hours per cycle). Solvents unsuitable for heating to 50° C. or cooling to 5° C. were subjected to evaporation, antisolvent addition at RT or maturation at RT, depending on the solvent.

After 24 h, any solutions at 5° C. were subjected to evaporation at RT with the lid removed. Samples subjected to evaporation were analyzed once dry. The remaining suspensions were left for 3 days at conditions before being extracted using an SPE cartridge and frit under positive pressure filtration.

A sample from the wet cake was analyzed by XRPD while the remaining sample was allowed to dry overnight (DS-2045-08-XX-W) at RT. After drying overnight, any novel patterns were analyzed by XRPD to determine if any changes in form occurred.

The results of the solubility and solvent selection assessment are shown in FIGS. 3A and 3B.

As can be seen from the FIGS. 3A and 3B, good solubility (dissolution in volumes <80 vol) at 25° C. was seen in 15 of the solvents tested. Generally, higher solubility was observed in aprotic, polar solvents such as THF, DMSO and acetone. Samples which were a mobile suspension or displayed partial dissolution were subsequently heated to 50° C. (for solvents with a sufficiently high boiling point). Clear solutions were obtained at 50° C. in IPA, 1-propanol, ACN, MeOH:water (3%), MeOH:water (5%), EtOH:water (5%), IPA:water (5%) and IPA:water (25%). The results would suggest that PP-001 shows a significant solubility curve with respect to temperature in a number of solvent systems. The remaining solvents, heptane toluene, chloroform and water remained suspensions. These solvents could therefore be suitable antisolvents.

Crystal polymorph screening. After the initial solubility assessment, the samples were used as the input material for the crystal polymorphism screen. As shown in FIGS. 3A, and 3B, the samples were subjected to various experimental conditions. Samples that maintained a suspension at 50° C. were subjected to maturation cycling between 25 and 50° C. (4 hours per cycle) overnight. Samples that formed a solution at 25 or 50° C. were cooled to 5° C. at 0.1° C./min and held at 5° C. overnight. 1,4-Dioxane (freezing point 11° C.) was evaporated at RT, while DMSO (freezing point 19° C.) was subjected to antisolvent addition (water) respectively. Diethyl ether (boiling point 35° C.) was subjected to maturation at RT.

After maturation overnight, any samples that remained a solution at 5° C. were then subjected to slow evaporation at room temperature until dry. The remaining suspensions were left for 3 days under the desired conditions before extracting the solid. Any solids obtained were isolated and initially analyzed by XRPD. The results of this analysis are summarized in FIGS. 4A and 4B.

The XRPD patterns of the samples isolated from most solvents were consistent with Form A. For samples that formed a solution, slow evaporation resulted in the formation of a new pattern, which matched the supplied reference for Form B (characterized in a previous study). Form B was isolated from isopropyl acetate, TBME, 1,4-dioxane, THF and THF:water (10%). A mixture of Form A and Form B was obtained from acetone/water evaporation. Antisolvent addition to DMSO resulted in the isolation of only amorphous material. Insufficient material was recovered from acetone and MeOH/water (30%) for analysis. The remaining samples comprising $C_1$-$C_5$ alcohols (ethanol, 1-propanol, isopropanol, 1-butanol, 2-butanol, 1-pentanol, 2-pentanol, or isopentanol), $C_1$-$C_5$ ketones (methyl ethyl ketone, methyisobutyl ketone, acetone), or $C_1$-$C_5$ acetates (methyl acetate, ethyl acetate, propyl acetate, butyl acetate, or pentyl acetate), resulted in Form A. No other new patterns were obtained during this screen. Further characterization of Form B can be found in Example 5.

Example 4—Characterization of Form A

PP-001 Form A was further characterized as described below, and its characteristics are summarized below in Table 10.

X-Ray Powder Diffraction. XRPD studies were conducted as previously described in Example 1. The XRPD pattern of PP-001 Form A is shown in FIG. 2A, and the 2θ values for Form A (with relative intensity) are shown in Table 10 below.

TABLE 10

| PP-001 Form A XRPD data. | |
|---|---|
| Pos. [°2θ] | Rel. Int. [%] |
| 5.2 | 49.3 |
| 10.3 | 2.3 |
| 12.3 | 2.1 |
| 12.7 | 3.3 |
| 14.8 | 30.6 |
| 15.2 | 6.7 |
| 15.6 | 100.0 |
| 16.5 | 38.4 |
| 18.5 | 3.9 |
| 19.6 | 28.6 |
| 20.0 | 30.0 |
| 20.3 | 24.4 |
| 20.8 | 43.2 |
| 21.4 | 7.7 |
| 22.9 | 21.4 |
| 23.7 | 12.1 |
| 24.2 | 25.0 |
| 24.9 | 26.0 |
| 25.6 | 27.8 |
| 25.8 | 14.9 |
| 26.1 | 35.7 |
| 27.5 | 24.4 |
| 27.8 | 10.0 |
| 29.0 | 3.6 |
| 29.3 | 4.4 |
| 29.5 | 2.5 |
| 29.8 | 4.9 |

Differential Scanning Calorimetry (DSC). DSC data were collected on a TA Instruments Q2000 equipped with a 50 position auto-sampler. Typically, 0.5-3 mg of each sample, in a pin-holed aluminum pan, was heated at 10° C./min from 25° C. to 250° C. A purge of dry nitrogen at 50 ml/min was maintained over the sample.

Modulated temperature DSC was carried out using an underlying heating rate of 2° C./min and temperature modulation parameters of ±0.636° C. (amplitude) every 60 seconds (period).

The instrument control software was Advantage for Q Series and Thermal Advantage and the data were analyzed using Universal Analysis or TRIOS.

The DSC showed a small endotherm onset at 177.6° C. (20 J/g) with some tailing and a 2nd sharp endotherm onset at 227.9° C. (108 J/g) likely corresponding to a melt. The 1st endotherm event was investigated further by VT-XRPD and thermal analysis and discussed further below (Example 4). The TGA data showed no weight loss before degradation (above 230° C.), consistent with the material being non-solvated which is in agreement with the proton NMR analysis.

Polarized Light Microscopy (PLM) and Scanning Electron Microscopy (SEAM). For PLM analysis, samples were analyzed on a Leica LM/DM polarized light microscope with a digital video camera for image capture. A small amount of each sample was placed on a glass slide, with or without immersion oil, and covered with a glass slip. The sample was viewed with appropriate magnification and partially polarized light, coupled to a λ false-color filter. Images were captured using StudioCapture or Image ProPlus software.

For SEM analysis, data were collected on a Phenom Pro Scanning Electron Microscope. A small quantity of sample was mounted onto an aluminum stub using conducting double-sided adhesive tape. A thin layer of gold was applied using a sputter coater (20 mA, 120 s).

Figure 11A:
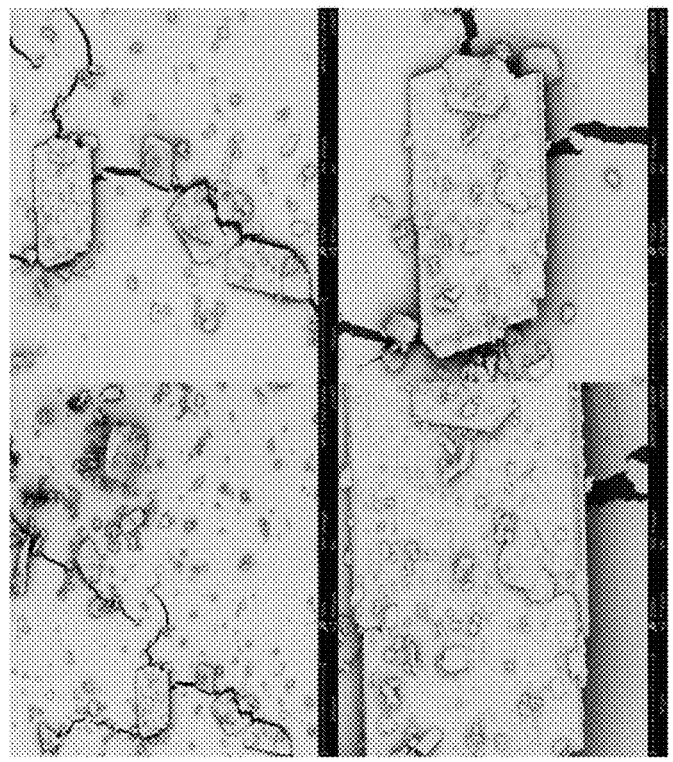
FIG. 11A-11B shows PP-001 Form A polymorph crystals using (A) Polarized Light Microscopy (PLM), and (B) Scanning Electron Microscopy (SEM).
Figure 11B:
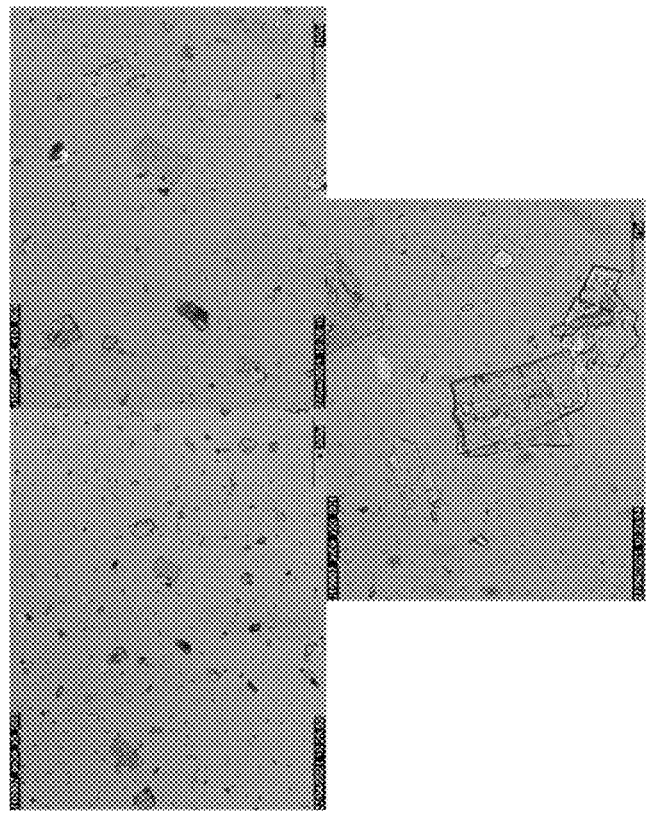

PLM and SEM images (FIGS. 11A and 111B, respectively) showed the sample to consist of a mixture of large plate-like crystals with a similar breath and width (up to ca. 200 μm) and smaller flake-like crystals. The surfaces of larger crystals are littered with the smaller flake-like crystals. Ion chromatography was used to confirm no anions or cations were present.

Gravimetric Vapor Sorption (GVS). Sorption isotherms were obtained using a SMS DVS Intrinsic moisture sorption analyzer, controlled by DVS Intrinsic Control software. The sample temperature was maintained at 25° C. by the instrument controls. The humidity was controlled by mixing streams of dry and wet nitrogen, with a total flow rate of 200 ml/min.

The relative humidity was measured by a calibrated Rotronic probe (dynamic range of 1.0-100% RH), located near the sample. The weight change, (mass relaxation) of the sample as a function of % RH was constantly monitored by a microbalance (accuracy ±0.005 mg).

Typically, 5-30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite. Data presented below in Table 11.

TABLE 11

| Method for SMS DVS Intrinsic experiments | |
| --- | --- |
| Parameter | Value |
| Adsorption - Scan 1 | 40-90 |
| Desorption, Adsorption - Scan 2 | 90-0, 0-40 |

TABLE 11-continued

| Method for SMS DVS Intrinsic experiments | |
| --- | --- |
| Parameter | Value |
| Intervals (% RH) | 10 |
| Number of Scans | 4 |
| Flow rate (ml/min) | 200 |
| Temperature (° C.) | 25 |
| Stability (° C./min) | 0.2 |
| Sorption Time (hours) | 6 hour time out |
| Number of cycles | 2 |

The sample was recovered after completion of the isotherm and re-analyzed by XRPD.

Figure 12:
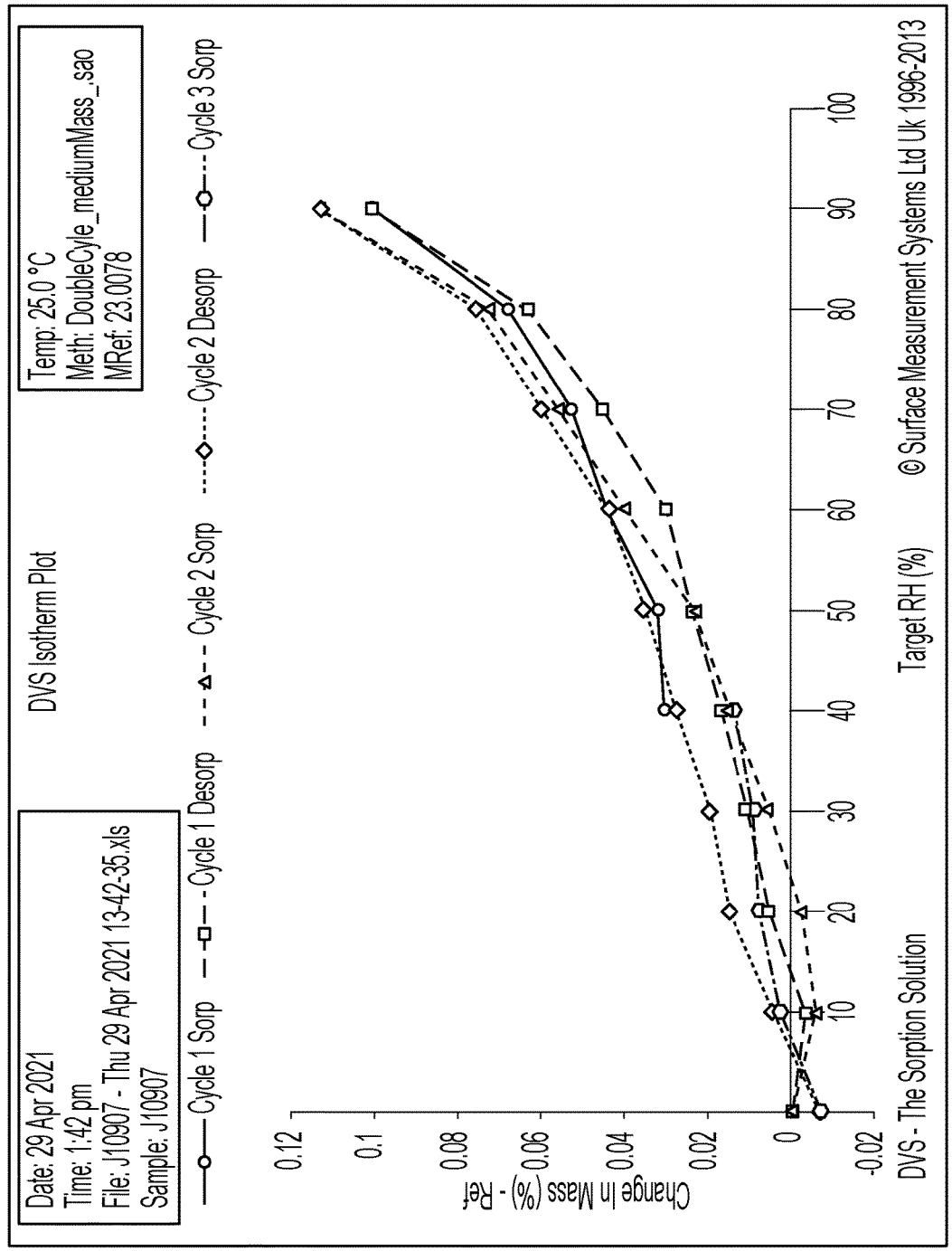
FIG. 12 shows the Gravimetric Vapor Sorption (GVS) isotherm of PP-001 Form A.

GVS analysis showed a gradual mass uptake of 0.12 wt % equivalent to 0.03 mol of water between 0 and 90% RH, with no significant hysteresis (FIG. 12). The kinetic plot shows some oscillation throughout the run, but this is believed to be due to the very low mass changes on humidity cycling. The sample is considered non-hygroscopic and was unchanged by XRPD post-GVS.

Chemical Purity Determination by HPLC. Purity analysis was performed on an Agilent HP1100/Infinity II 1260 series system equipped with a diode array detector and using OpenLAB software. The full method details are provided below in Table 12:

TABLE 12

| HPLC method for chemical purity determination | | |
| --- | --- | --- |
| Parameter | Value | |
| Type of method | Reverse phase with gradient elution | |
| Sample Preparation | 0.2-0.5 mg/ml in acetonitrile:water 1:1 | |
| Column | Supelco Ascentis Express C18 2.7 μm 100 × 4.6 mm | |
| Column Temperature (° C.) | 25 | |
| Injection (μl) | 5 | |
| Detection: Wavelength, Bandwidth (nm) | 255, 90 | |
| Flow Rate (ml/min) | 2 | |
| Phase A | 0.1% TFA in water | |
| Phase B | 0.085% TFA in acetonitrile | |
| Timetable | Time (min) | % Phase A | % Phase B |
| | 0 | 95 | 5 |
| | 6 | 5 | 95 |
| | 6.2 | 95 | 5 |
| | 8 | 95 | 5 |

Figure 12A:
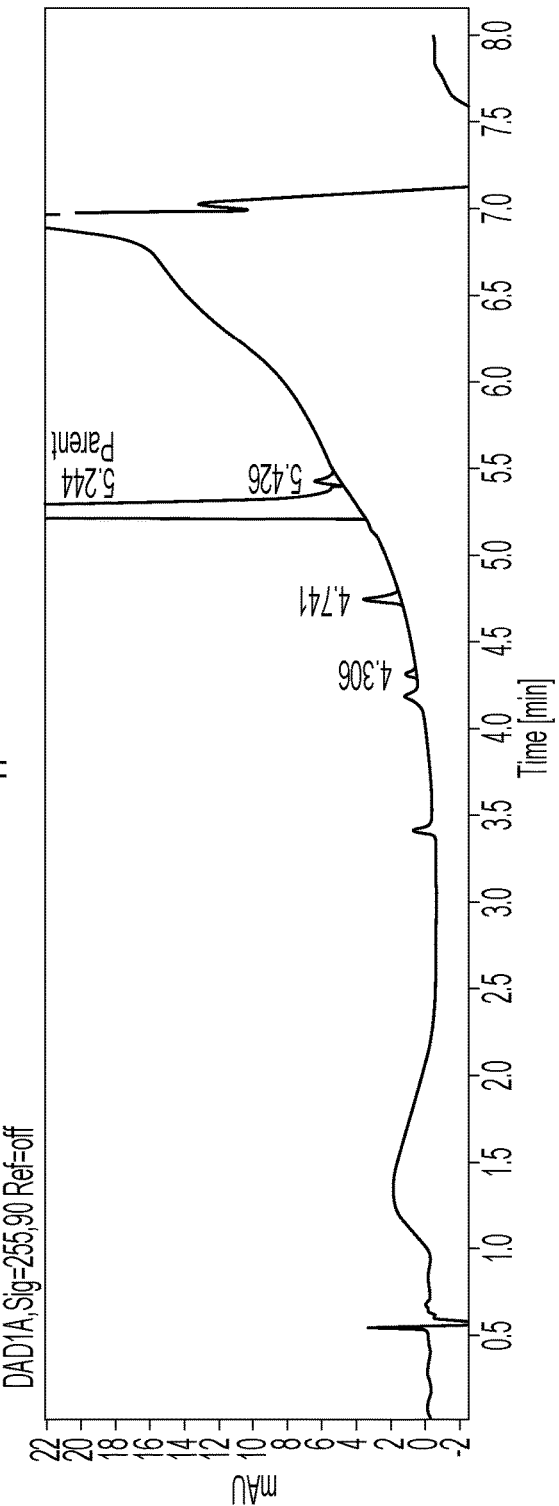
FIG. 12A-12C shows HPLC profiles of (A) PP-001 Form A starting material, (B) PP-001 Form A after storage at 40° C./75% relative humidity for 8 days, and (C) PP-001 Form A after storage at 25° C./97% relative humidity for 8 days.
Figure 12B:
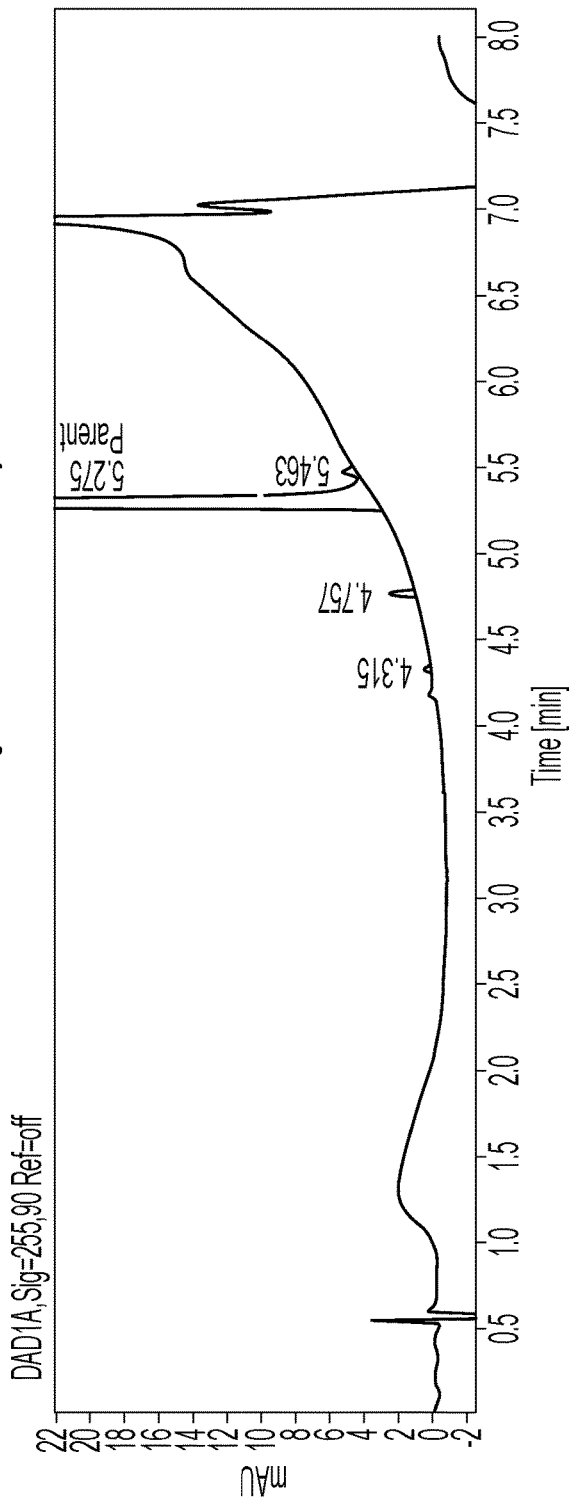
Figure 12C:
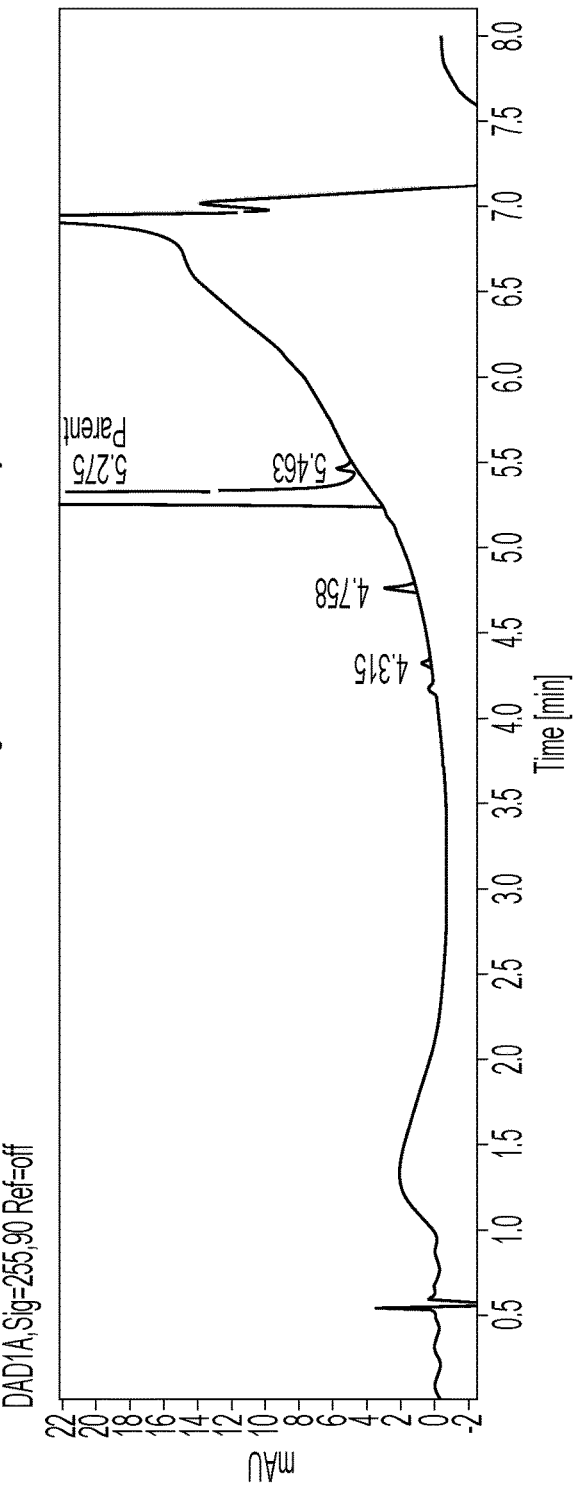
Figure 13B:
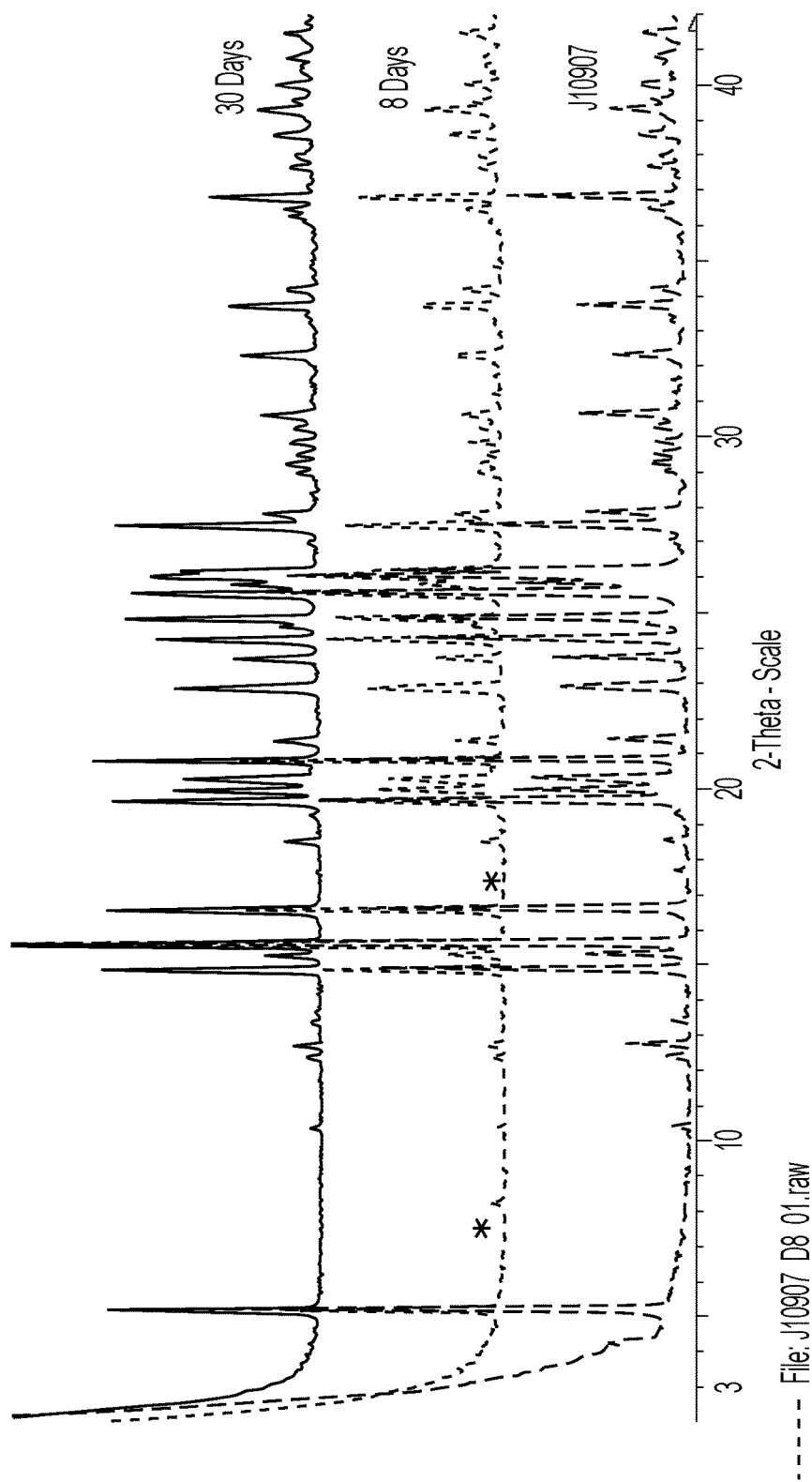
Figure 14C:
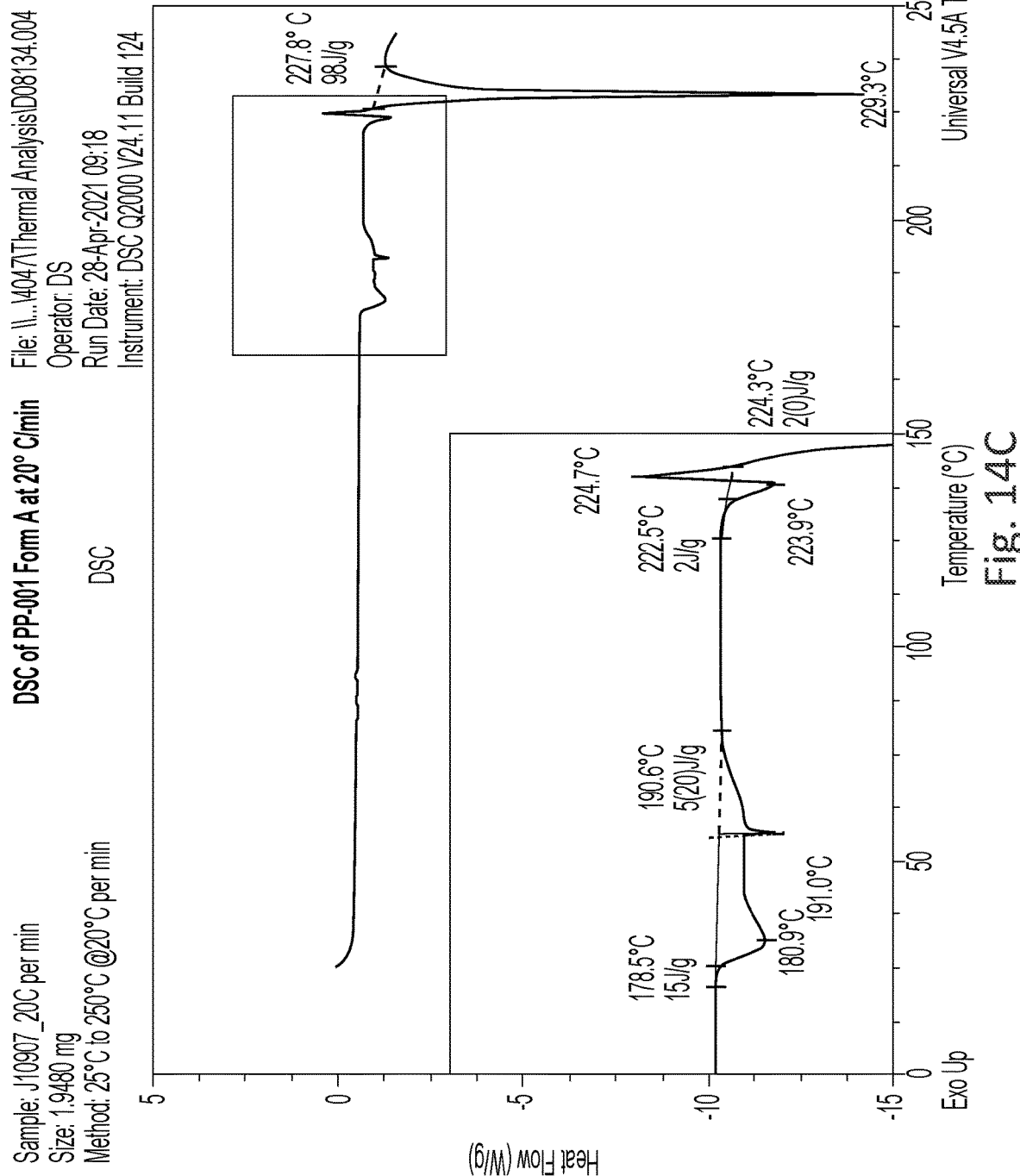

HPLC indicated the material to have a purity of 99.6% (FIG. 12A). Eight days under accelerated storage conditions 40° C./75% RH showed the sample to be unchanged by XRPD and HPLC (FIG. 12B). Eight days under accelerated storage conditions 25° C./97% RH showed the sample to be unchanged by HPLC (FIG. 12C), but a small peak was gained at 8.1 2θ angle and a loss of a small peak at 17.6 2θ angle was observed (FIG. 13A). The sample was left for an additional 22 days (total 30 days storage) and re-analyzed by XRPD, appearing as Form A, lacking the additional peaks previously observed (FIG. 13B). It was therefore possible that contamination of sample on the instrument in the previous 8-day timepoint was the likely cause of the additional peaks, rather than a form chance or degradation.

Thermodynamic Aqueous Solubility. Aqueous solubility was determined by suspending sufficient compound in relevant media to give a maximum final concentration of ≥10 mg/ml of the parent free-form of the compound. The suspension was equilibrated at 25° C., on a Heidolph plate shaker set to 750 rpm for 24 hours. The pH of the saturated solution was then measured, and the suspension filtered through a glass fiber C filter (particle retention 1.2 μm) and diluted appropriately. Quantitation was by HPLC with reference to a standard solution of approximately 0.15 mg/ml in DMSO. Different volumes of the standard, diluted and undiluted sample solutions were injected. The solubility was calculated using the peak areas determined by integration of the peak found at the same retention time as the principal peak in the standard injection. Data presented below in Table 13.

TABLE 13

| HPLC method for solubility measurements | |
| --- | --- |
| Parameter | Value |
| Type of method | Reverse phase with gradient elution |
| Column | Phenomenex Luna, C18 (2) 5 μm 50 × 4.6 mm |
| Column Temperature (° C.) | 25 |

TABLE 13-continued

| HPLC method for solubility measurements | | |
| --- | --- | --- |
| Standard Injections (μl) | 1, 2, 3, 4, 5, 7 | |
| Test Injections (μl) | 1, 2, 3, 10, 15, 20 | |
| Detection: Wavelength, Bandwidth (nm) | 260, 90 | |
| Flow Rate (ml/min) | 2 | |
| Phase A | 0.1% TFA in water | |
| Phase B | 0.085% TFA in acetonitrile | |

| Timetable | Time (min) | % Phase A | % Phase B |
| --- | --- | --- | --- |
| | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

The thermodynamic solubility was determined in Fasted State Stimulated Intestinal Fluid (FaSSIF) to be 0.76 mg/ml. The XRPD of the residual solid was largely unchanged, although some extra peaks corresponding to NaCl can be seen.

TABLE 14

| Characterization data for PP-001 Form A. | |
| --- | --- |
| XRPD | Crystalline, Form |
| $^1$H NMR | 7 non-exchangeable protons detected by $^1$H-NMR, consistent with structure. Residual IPA (<0.1 mol equiv.). |
| DSC | Small endotherm onset at 177.6° C. (20 J/g) with some tailing, $2^{nd}$ sharp endotherm onset at 227.9° C. (108 J/g) likely corresponding to a melt. |
| TGA | No mass loss before decomposition above ca. 230° C. |
| PLM | Mixture of large plate-like crystals with a similar breath andwidth (up to ca. 200 μm) and smaller flake-like crystals. |
| SEM | Mixture of large plate-like crystals with a similar breath andwidth (up to ca. 200 μm) and smaller flake-like crystals. Surfaces of larger crystals are littered with the smaller flake-like crystals. |
| IC | No anions or cations observed |
| HPLC | 99.6% purity |
| 40° C./75% RH XRPD & HPLC | 8 days. Unchanged/99.6% |
| 25° C./97% RH XRPD & HPLC | 8 Days Small peak gain at 8.1 2Θ and a loss of small peaket 17.6 2Θ. Otherwise unchanged/99.6%. 30 Days Form A* |
| Thermodynamic Solubility in FaSSIF | 0.76 mg/ml (pH 6.4). XRPD unchanged in form plus NaCl reference peaks. |
| GVS | Gradual mass uptake of 0.12 wt % equiv. to 0.03 mol of water between 0 and 90% RH. No significant hysteresis. Kinetic plot shows some oscillation throughout the run, believed to be due to low mass uptake. Sample is non- hygroscopic. |
| XRPD Post-GVS | Unchanged |

*additional peaks no longer present, possible contamination of sample oninstrument in previous 8-day timepoint.

Example 5—Thermal Studies on Form A

Form A is characterized as a stable, anhydrous form. However, the additional thermal event at 177.6° C. required further analysis to determine whether a form change occurred. Form A was subjected to DSC analysis at different ramp rate (5, 10, 20 & 50° C./min), DSC cycling (25 to 205, 205 to 25 and 25 to 250° C. at 10° C./min) and MDSC. In addition, the sample was subjected to VT-XRPD up to 200° C. The results are summarized in Table 15.

TABLE 15

Results of thermal analysis of PP-001 Form A.

| Technique | Results |
| --- | --- |
| DSC (5° C./min) | Small endotherm onset at 178.3° C. (18 J/g) with sometailing, 2$^{nd}$ sharp endotherm onset at 227.3° C. (87 J/g)likely corresponding to a melt. |
| DSC (10° C./min) | Small endotherm onset at 177.6° C. (20 J/g) with some tailing, 2$^{nd}$ sharp endotherm onset at 227.9° C. (108 J/g)likely corresponding to a melt. |
| DSC (20° C./min) | Small endotherm onset at 178.5° C. (15 J/g) with sometailing, 2$^{nd}$ sharp endotherm onset at 190.6° C. (5 J/g) likely artefact, sharp endo/exo event onset at 222.5 (2 J/g) and 224.3° C. (<1 J/g) respectively, followed by alarge sharp endotherm onset at 227.8° C. (98 J/g) likely corresponding to a melt. |
| DSC (50° C./min) | Baseline poor up to 100° C. Small double endotherms withonsets at 88.0° C. (4 J/g) and 92.6° C. (5 J/g), possible artefacts. Small endotherm with some tailing with an onset of 180.5° C. (19 J/g). Sharp endo/exo event onset at224.7° C. (12 J/g), followed by a large sharp endotherm onset at 229.5° C. (59 J/g) likely corresponding to a melt. |
| DSC Cycling | 1$^{st}$ Cycle (25 to 205° C.): Small endotherm onset at 178.2° C. (19 J/g) with tailing. 2$^{nd}$ Cycle (205 to 25° C.) Small exotherm onset at 159.4° C. (10 J/g) with reduced tailing. 3$^{rd}$ Cycle (25 to 250° C.): Small endotherm onset at 177.1° C. (12 J/g), sharp endotherm at 228.2° C. (103 J/g) |
| Melt-Quench-Cool (MDSC) | Small endotherm onset at 177.7° C. (20 J/g) with some tailing, 2$^{nd}$ sharp endotherm onset at 227.8° C. (99 J/g) likely corresponding to a melt. After cooling, MDSC shows baseline change with a midpoint of 36.4° C., corresponding to a Tg. A double exotherm is noted with anonset at 86.9° C. (29 J/g), 2$^{nd}$endotherm observed at 196.7° C. (15 J/g) |
| VT-XRPD | Observable changes in XRPD pattern at 200° C. Changesare generally lost on cooling back to RT. Possible high temperature form observed. |

The aim of the varying heating rate experiments was to be able to separate the endothermic events at approximately 180° C., in order to demonstrate the form change by variable temperature (VT)-XRPD. From the results in Table 15, when varying ramp rate from 5 to 50° C./min, with the exception of some artifacts noted in the 20 and 50° C./min runs, little change was observed before the onset of this endotherm (FIGS. 14A-14D). In all cases, the event remained present, with the same tailing effect visible. The most interesting revelation was the resolution of an additional sharp endo/exo event prior the melt, only visible on faster heating at 20 and 50° C./min (onset at 222.5 and 224.7° C. respectively), suggesting there may be an additional form change prior to the main melt. However, the closeness of the sample melt (ca. 227-228° C.) makes it difficult to probe this further without specialized equipment.

With respect to the 1st endotherm at ca. 177° C., DSC cycling was conducted to the probe this event further. In this case, the small endotherm showed an onset at 178.2° C. (19 J/g) on the first heating cycle, consistent with the previous DSC runs. On cooling (205 to 25° C.) a small exotherm with an onset at 159.4° C. (10 J/g) was observed. On the 2nd heating cycle (25 to 250° C.) the small endotherm was observed again with an onset at 177.1° C. (12 J/g) before a sharp endotherm at 228.2° C. (103 J/g) consistent with the melt. This analysis would indicate that the endothermic event at 177° C. is a reversible transition.

Figure 15A:
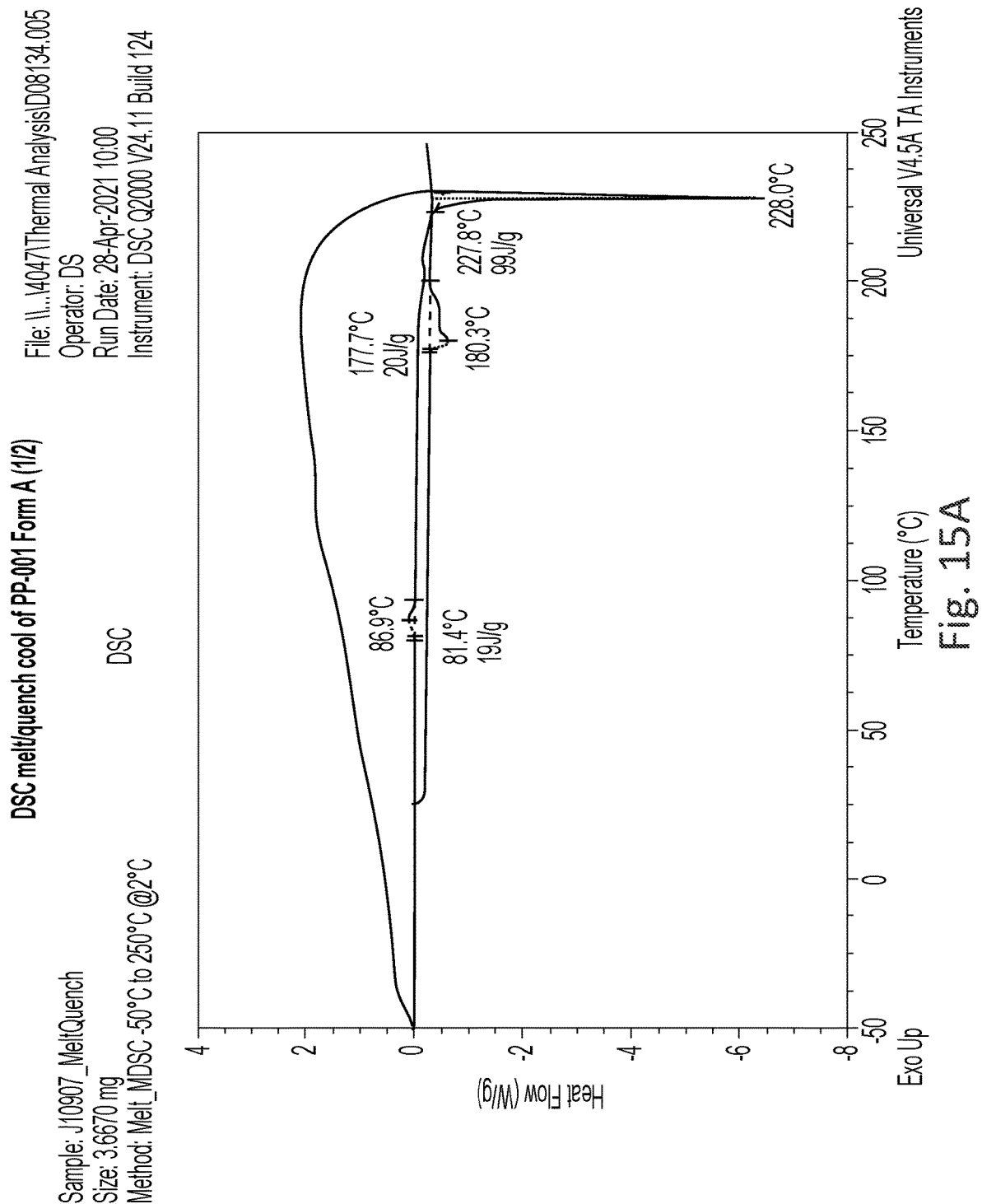
FIG. 15A-15B show the results of a DSC melt/quench cool analysis of PP-001 Form A.
Figure 15B:
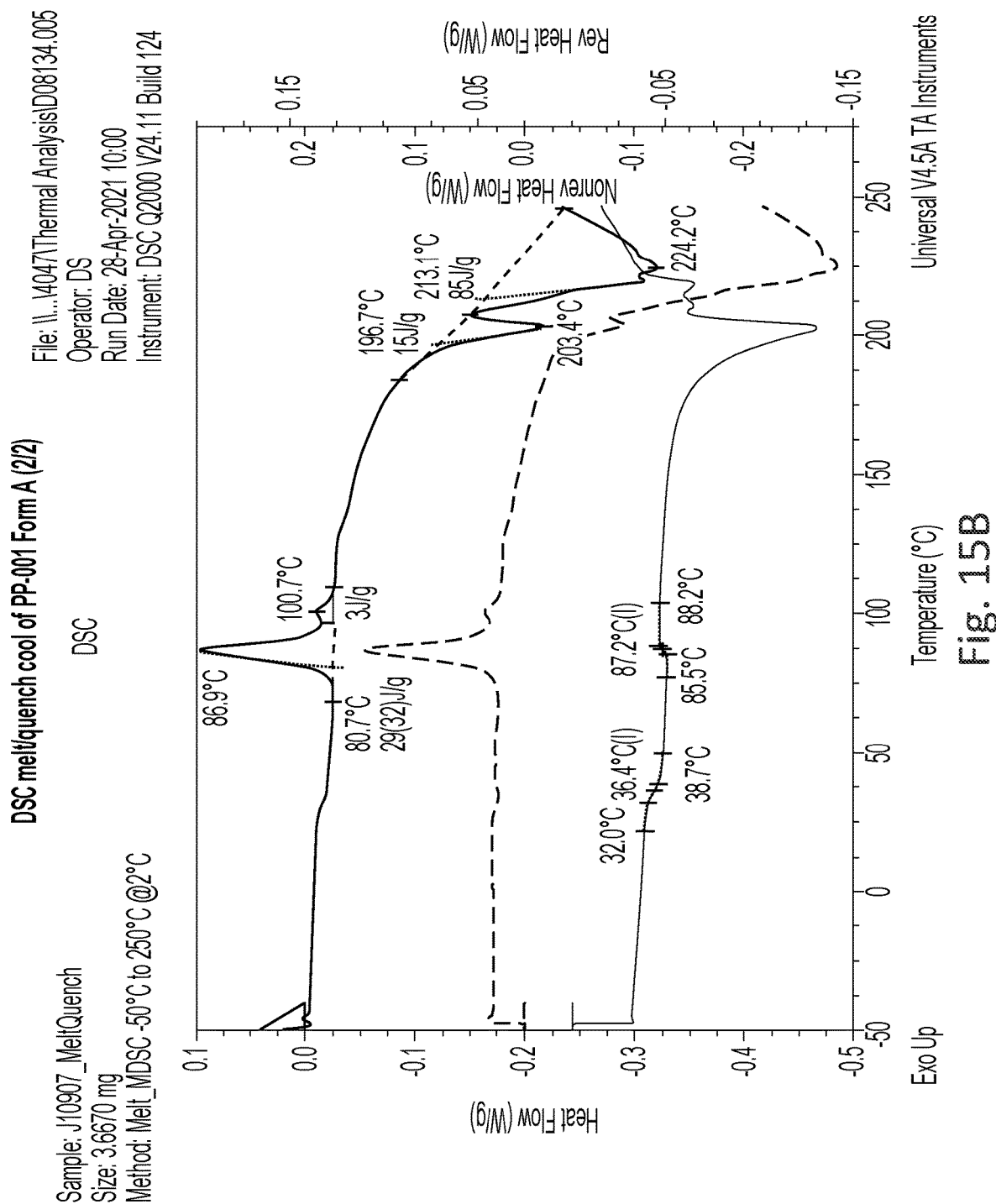

In the melt-quench-cooling measurement, the sample was rapidly cooled after melting and a Tg at 36.4° C. was determined upon re-heating. This is followed by a double exotherm with an onset at 86.9° C. (29 J/g) and a 2nd endotherm observed at 196.7° C. (15 J/g) (FIGS. 15A-15B)

Example 6—Characterization of PP-001 Form B

Preparation of PP-001 Form B. Amorphous PP-001 (1 g) was subjected to 10 vol (10 ml) of toluene. The suspension was maturated at 5° C., 300 rpm overnight. Solid form turnover was monitored by taking ca. 20 µl aliquots and subjecting them to XRPD. The solid was extracted using a Buchner filtration. The residual material was extracted using x2 1 mL cold (5° C.) toluene washes. The combined solid was dried under vacuum for over 1 hour. Yield=697.41 mg, 69.7%.

Characterization of Form B. PP-001 Form B was characterized by XRPD, DSC, PLM, SEM, HPLC, and GVS analysis using the same procedures described above in Example 3.

Figure 16:
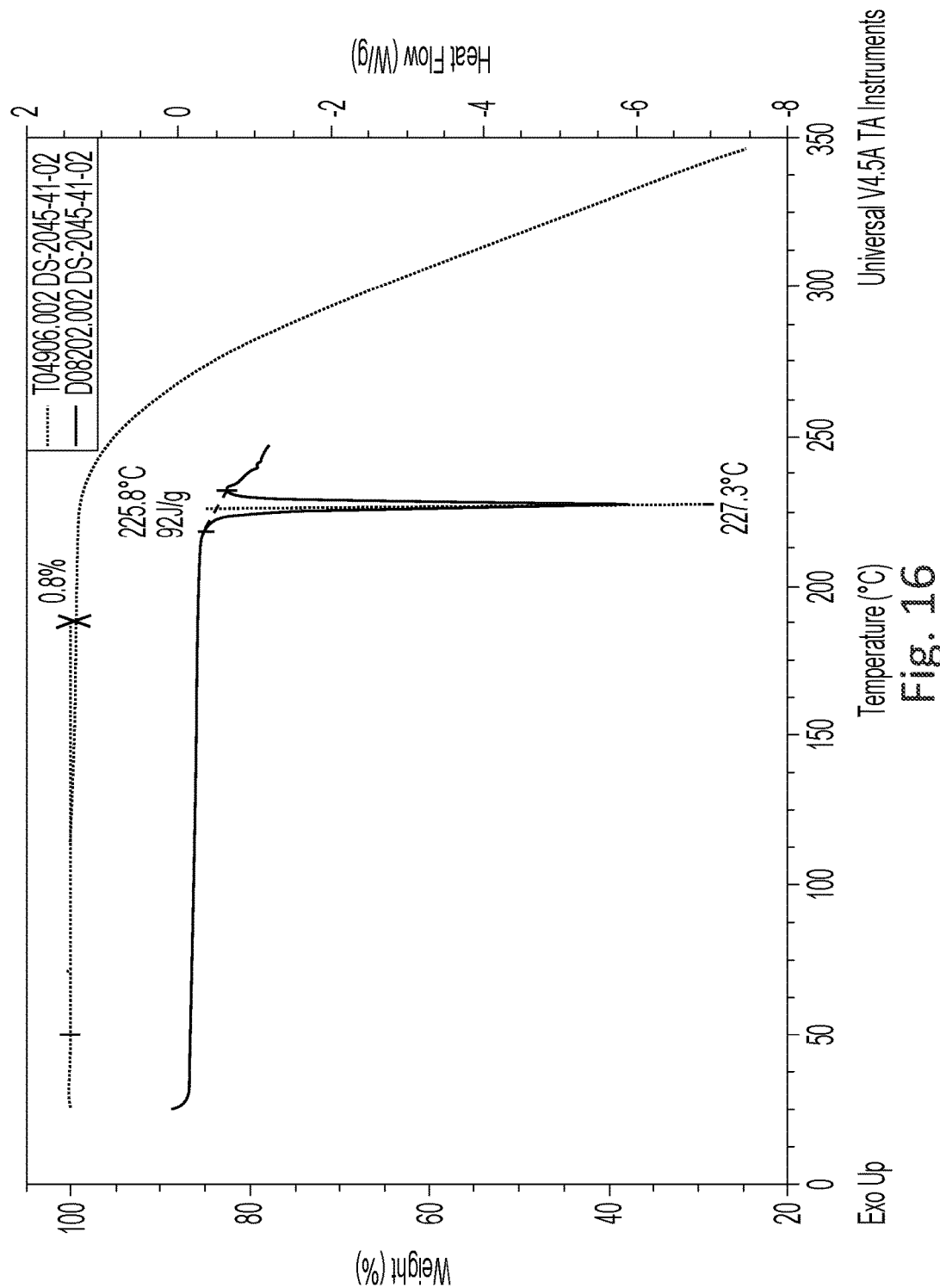
FIG. 16 shows TGA and DSC analysis of PP-001 Form B.
Figure 17A:
FIG. 17A-17B shows PP-001 Form B polymorph crystals using (A) Polarized Light Microscopy (PLM), and (B) Scanning Electron Microscopy (SEM).
Figure 17B:
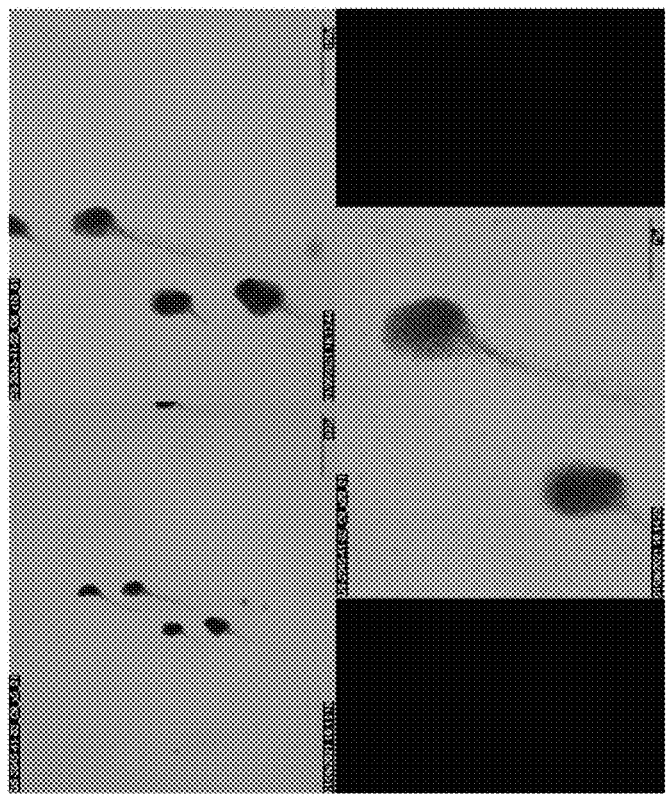
Figure 18A:
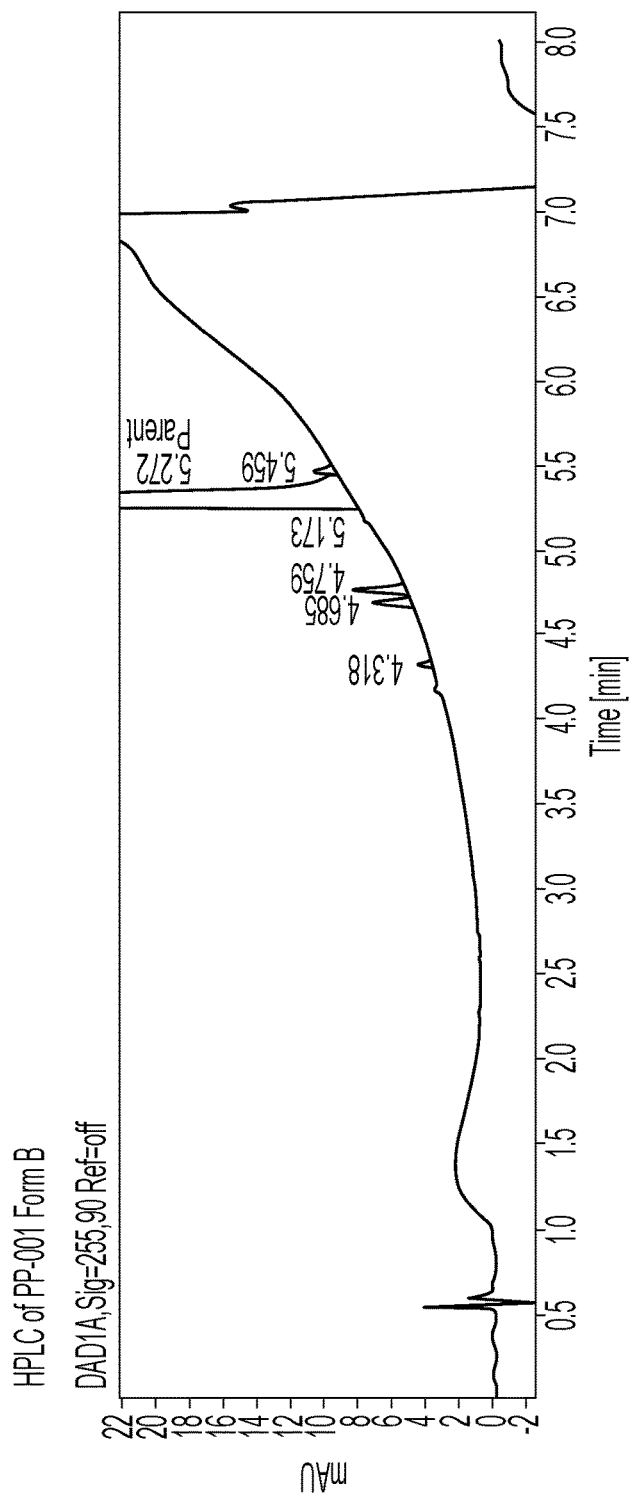
FIG. 18A-18C shows HPLC profiles of (A) PP-001 Form B starting material, (B) PP-001 Form B after storage at 40° C./75% relative humidity for 8 days, and (C) PP-001 Form B after storage at 25° C./97% relative humidity for 8 days.
Figure 18B:
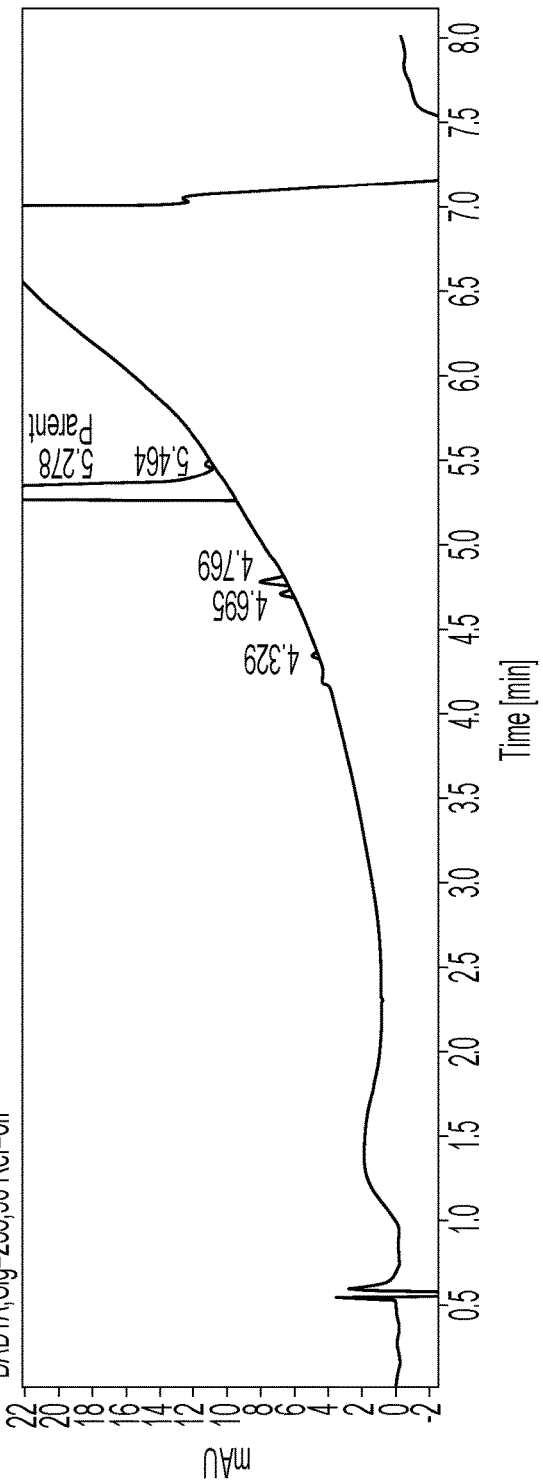
Figure 18C:
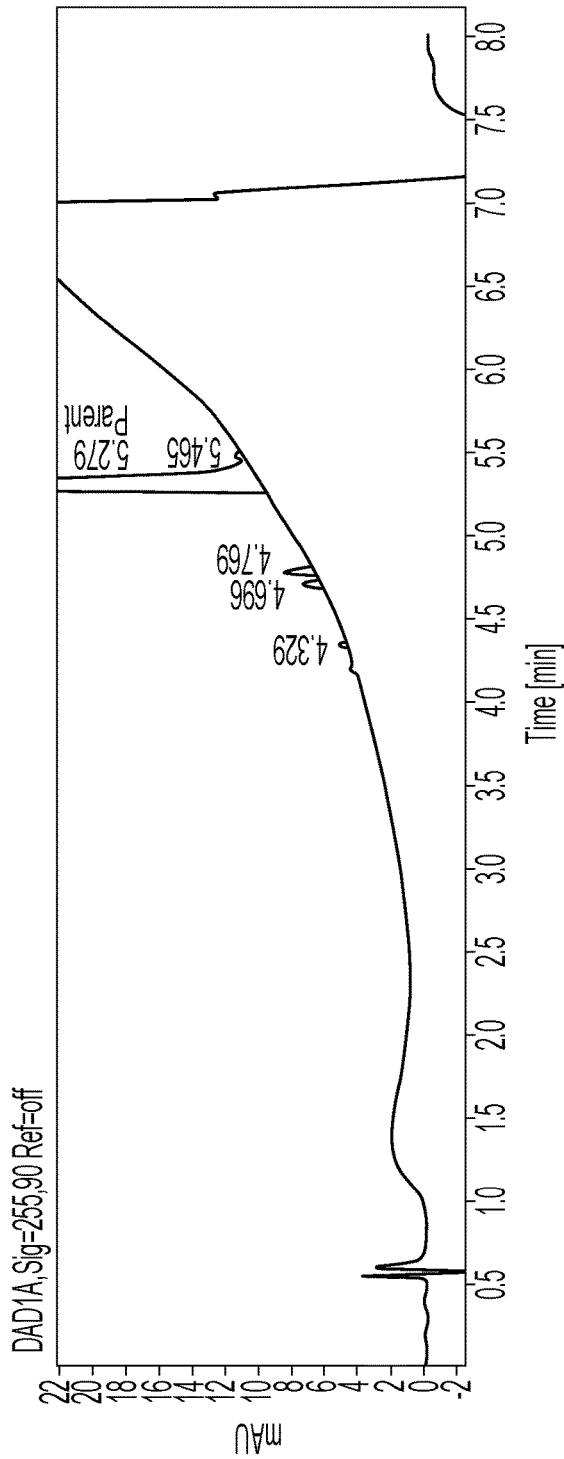
Figure 19:
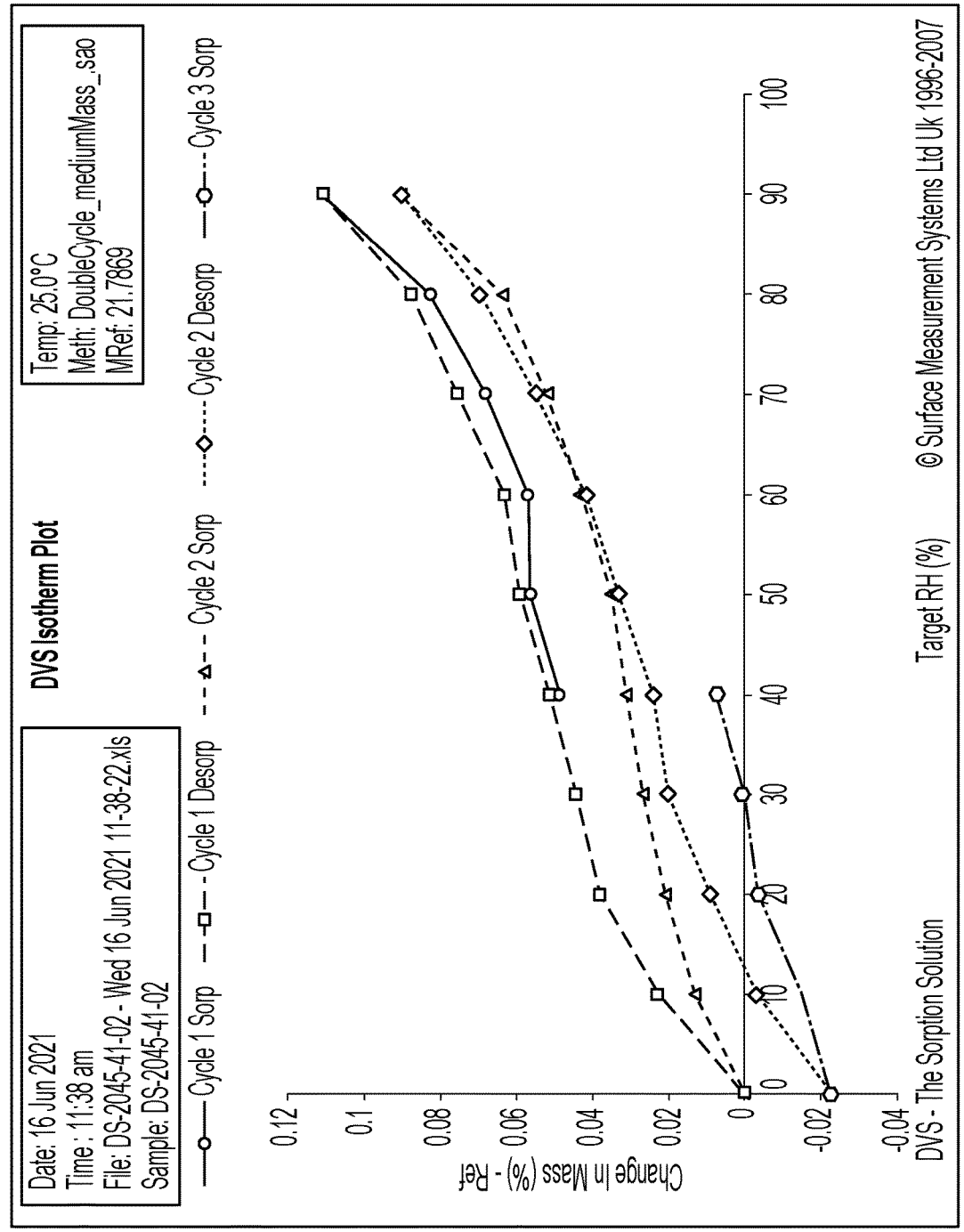
FIG. 19 shows the GVS isotherm of PP-001 Form B.

The DSC trace shows a single sharp exotherm at 225.8° C. (92 J/g) (FIG. 16). PLM and SEM images indicate the particles to be a series of spherical agglomerates (ca. 50 to 100 µm in diameter), which consist of small (<10 µm) plate-like crystals (FIGS. 17A-17B). HPLC analysis indicated the sample maintained a high purity of 99.5% (FIG. 18A). Accelerated storage under 40° C./75% RH and 25° C./97% RH for 7 days showed no observable changes by XRPD in either case. HPLC purity was found to be 99.6% and 99.4% respectively after storage (FIGS. 18B-18C). The isotherm plot from GVS analysis shows a gradual mass uptake of 0.10 wt % equiv. to 0.03 mol of water between 0 and 90% RH on adsorption (FIG. 19). There is a small hysteresis between adsorption and desorption. The sample was unchanged by XRPD post-GVS analysis. GVS results show Form B to be non-hygroscopic and stable to variable humidity. The results of these studies are summarized below in Table 16.

TABLE 16

Characterization of PP-001 Form B.

| | |
|---|---|
| XRPD | Crystalline, Form B |
| $^1$H NMR | NMR consistent with structure. Residual toluene (0.05 mol equiv.) detected. |
| DSC | Sharp endotherm onset at 225.8° C. (92 J/g) likely corresponding to a melt. |
| TGA | 0.8% mass loss between 50 and 200° C. (equiv. to 0.04 mol of toluene). Decomposition above ca. 225° C. |
| PLM | Agglomerated particulates consisting of very small crystals (<<75 μm). |
| SEM | Some spherical agglomerates (up to ca. 50 to 100 μm in diameter), which consist of small elongated (<10 μm) plate-like crystals. |
| HPLC | 99.5% |
| 40° C./75% RH XRPD & HPLC | Unchanged/99.6% |
| 25° C./97% RH XRPD & HPLC | Unchanged/99.4% |
| GVS | Gradual mass uptake of 0.10 wt % equiv. to 0.03 mol of water between 0 and 90% RH. Small hysteresis looks more pronounced due to low mass uptake. Sample is non-hygroscopic. |
| XRPD Post-GVS | Unchanged |
| Identity | Form B, Anhydrous, Stable. |

XRPD studies on Form B were conducted as previously described in Example 1. The XRPD profile of PP-001 Form B is shown in FIG. 2B, and the 2θ values for Form B are shown in Table 17 below.

TABLE 17

PP-001 Form B XRPD data.

| Pos. [°2θ] | Rel. Int. [%] |
|---|---|
| 5.2 | 90.4 |
| 13.4 | 3.8 |
| 14.2 | 36.7 |
| 14.9 | 71 |
| 15.6 | 25.5 |
| 16.2 | 7.5 |
| 17.6 | 100 |
| 18.0 | 16.2 |
| 19.3 | 23.9 |
| 20.0 | 9 |
| 20.9 | 90.8 |
| 22.0 | 17.3 |
| 23.5 | 17.1 |
| 24.0 | 22.6 |
| 24.3 | 15.9 |
| 24.9 | 69.3 |
| 25.4 | 79.5 |
| 26.1 | 15.3 |
| 26.4 | 22.2 |
| 27.0 | 25.3 |
| 27.3 | 24.3 |
| 28.2 | 29.7 |
| 28.6 | 23.5 |
| 29.1 | 8.6 |

Figure 20A:
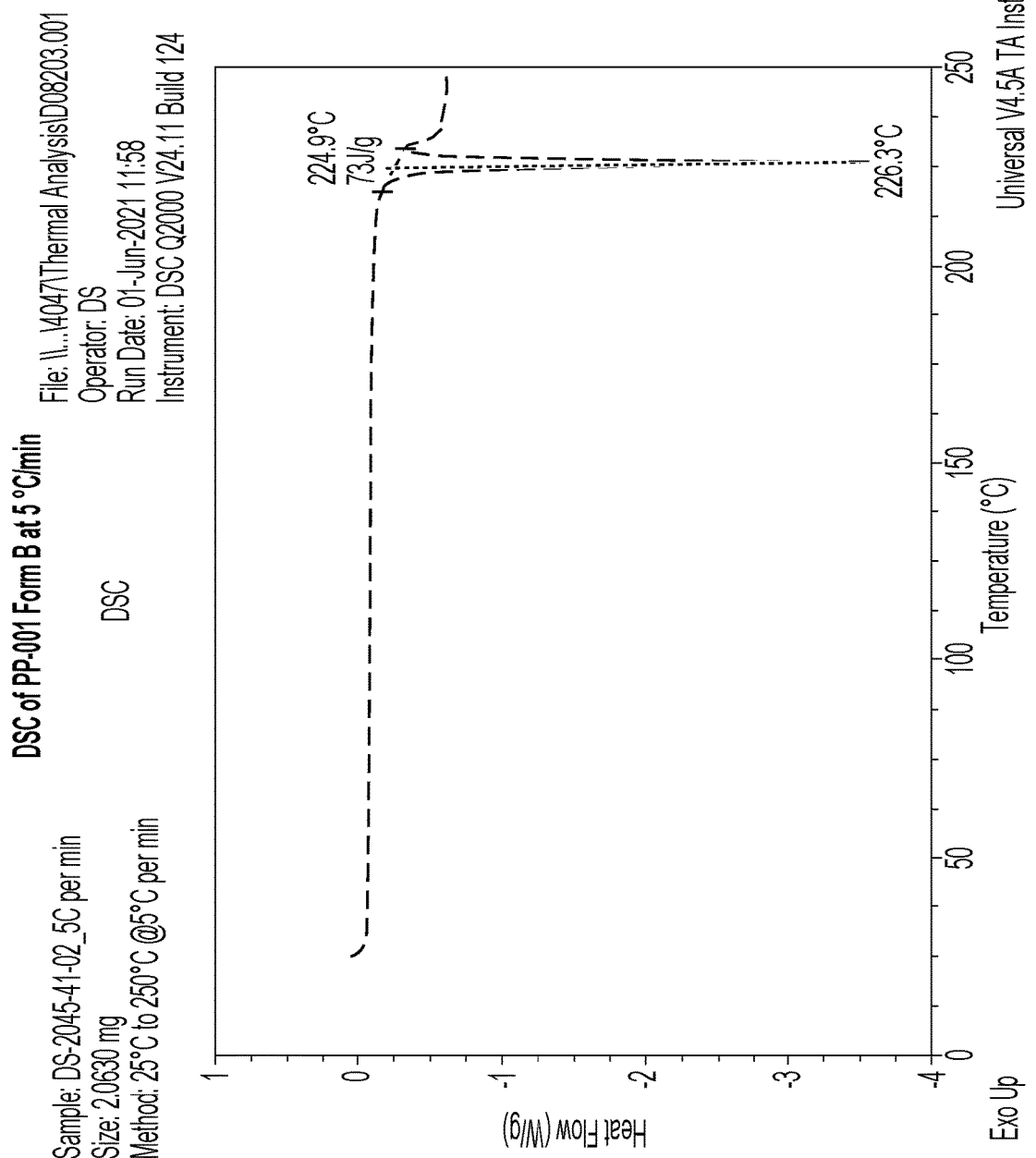
FIG. 20A-20C shows the results of Differential Scanning Calorimetry (DSC) analysis of PP-001 Form B at (A) 5° C./min, (B) 20° C./min, and (C) 50° C./min.
Figure 20B:
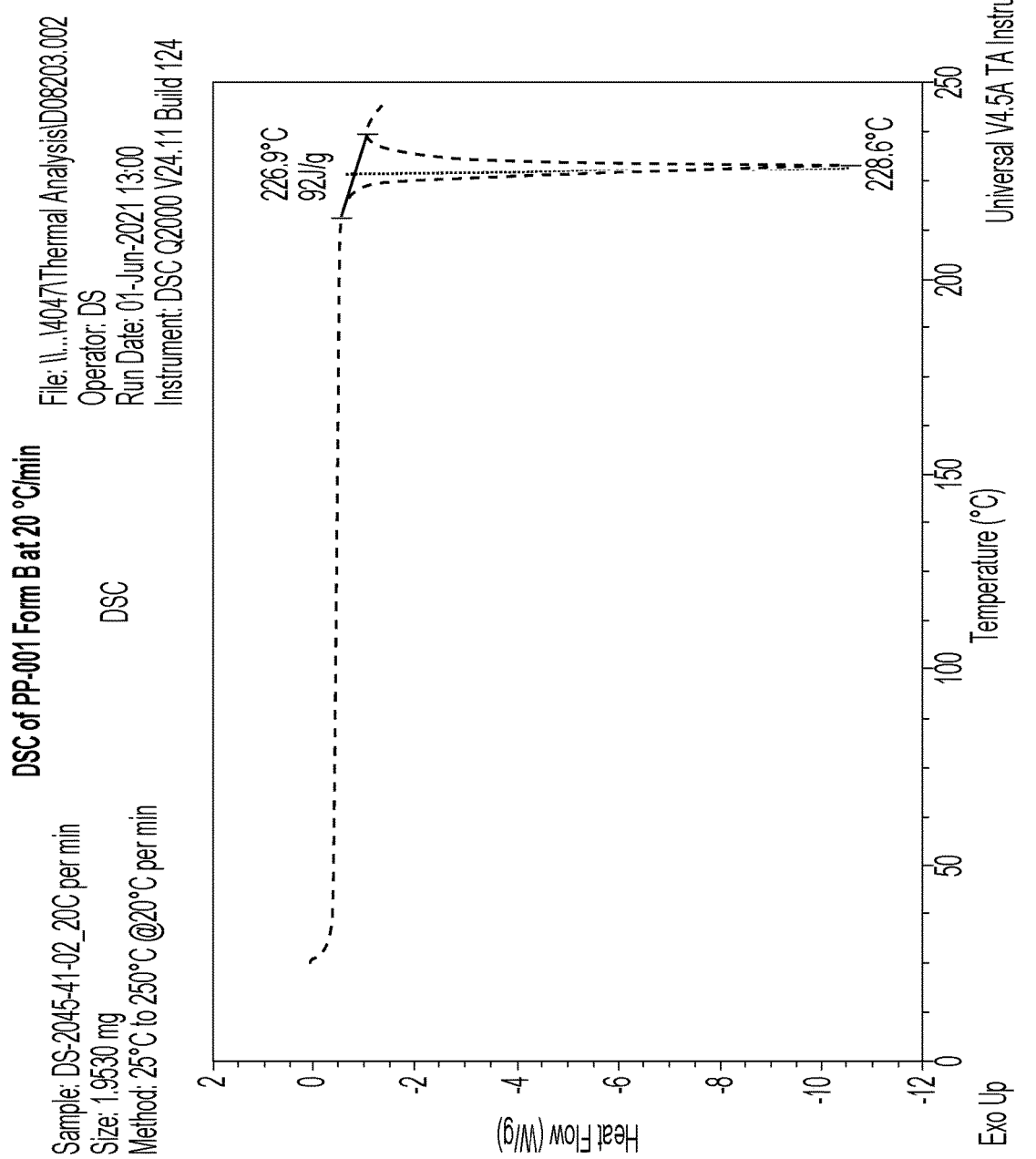
Figure 20C:
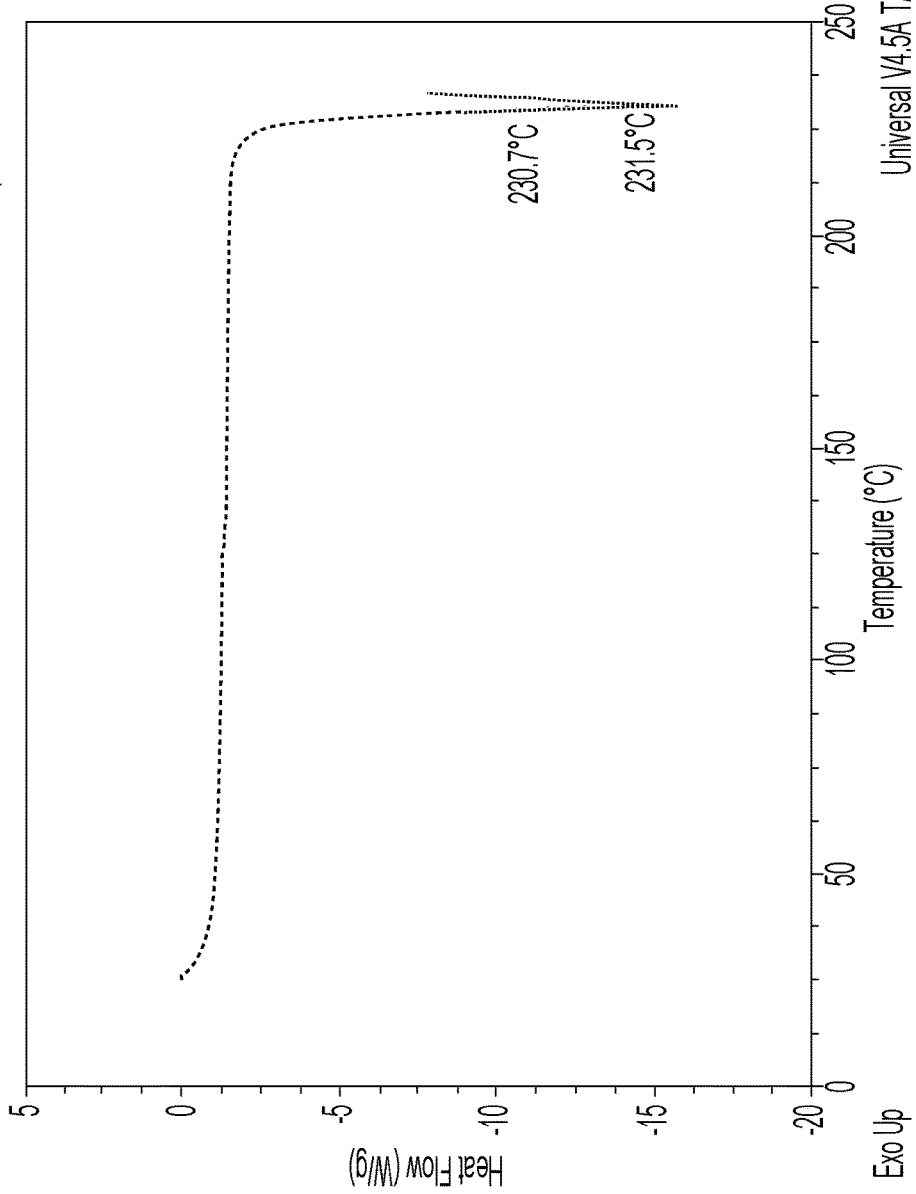

Additional thermal studies were conducted using the scale-up of Form B, where the ramp rate of the DSC was varied from 5 to 50° C./min, as was conducted on Form A in Example 4. The results are outlined in Table 18 below and FIGS. 20A-20C.

TABLE 18

Thermal characterization of PP-001 Form B.

| | |
|---|---|
| DSC (5° C./min) | Sharp endotherm onset at 224.9° C. (73 J/g) likely corresponding to a melt |
| DSC (10° C./min) | Sharp endotherm onset at 225.8° C. (92 J/g) likely corresponding to a melt. |
| DSC (20° C./min) | Sharp endotherm onset at 226.9° C. (92 J/g) likely corresponding to a melt. |
| DSC (50° C./min) | Beginning of a sharp endotherm with an onset at 230.7° C. and a peak max of 231.5° C., likely corresponding to a melt. * |

* tail end of endotherm lost due to high ramp rate; hence J/g cannot be calculated accurately.

Example 7—Thermodynamic Stability Analysis

The aim of this work was to investigate the order of stability of the scaled-up Form A and Form B via competitive slurrying of the materials in a range of solvents at 5° C., 25° C. and 50° C.

In addition, the thermodynamic solubility and the IDR of the two forms was compared in selected media.

The proposed solvents were aliquoted (1 ml) into HPLC vials and held at 5° C., 25° C. and 50° C. respectively, equilibrating at 300 rpm. To each vial, PP-001 was added in increasing amounts until a sustained suspension was observed at the desired temperature. The saturated solutions were allowed to equilibrate overnight.

Approximately 300 mg of Form B, prepared as described previously in Example 5, and the Form A were added to a 20 ml scintillation vial. The vial was subjected to turbula mixing for over 2 hours to ensure the mixture was homogenous. Approximately 30 mg of a mixture of Form A and Form B was added to a series HPLC vials. The vials were placed at 5, 25 and 50° C., 300 rpm. The suspensions prepared previously were filtered through a PTFE syringe directly into each vial to suspend the prepared form mixture in a saturated solution of the target solvent. Polymorph turnover was investigated by taking a 30-50 μl aliquot of the suspension and analyzing by XRPD.

Figure 21:
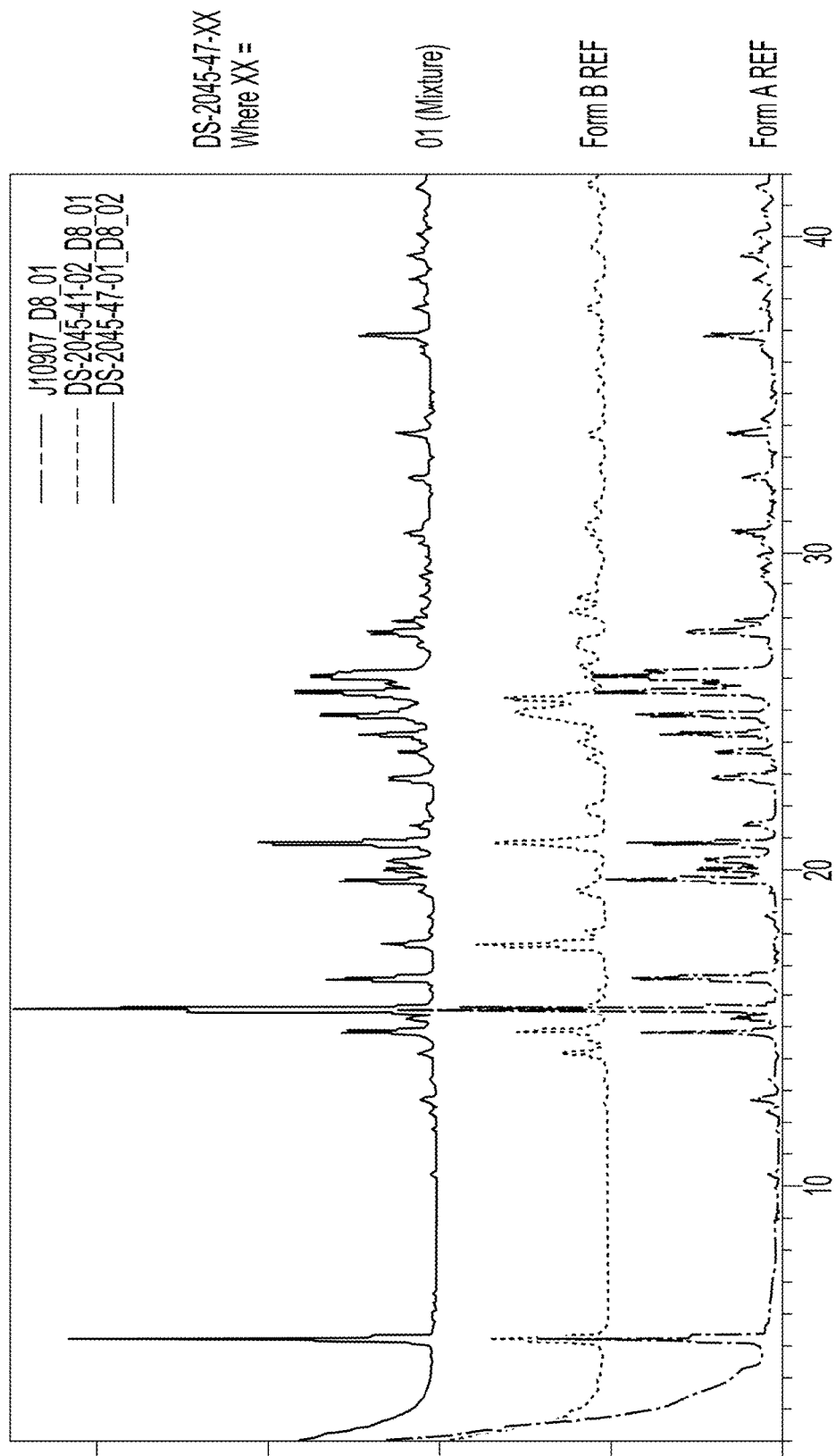
FIG. 21 shows an XRPD overlay of PP-001 Form A, PP-001 Form B, and a mixture of PP-001 Forms A and B (DS-2054-47).
Figure 22:
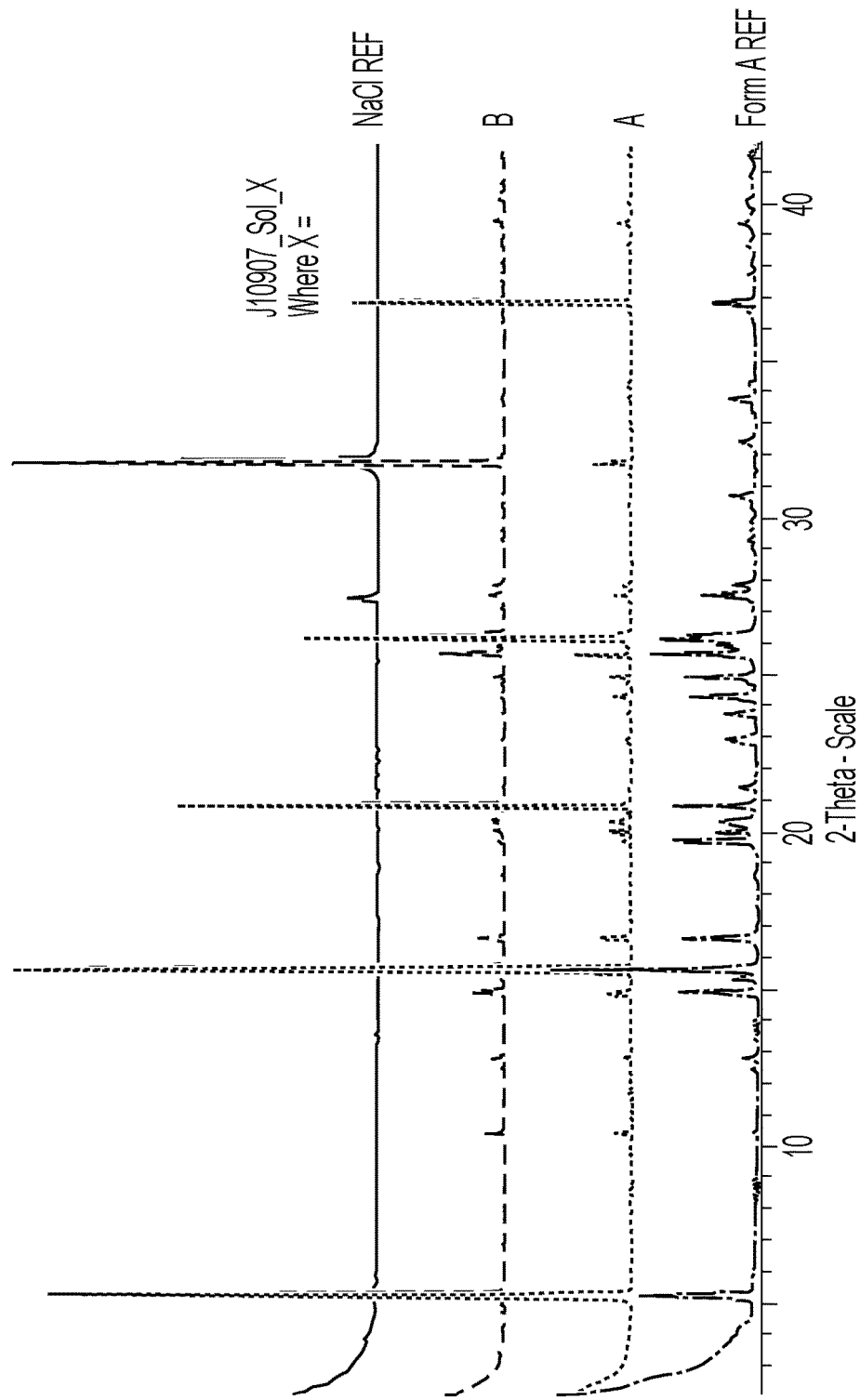
FIG. 22 shows an XRPD overlay of aliquots taken during competitive slurrying of PP-001 Form A and Form B after 5 days.
Figure 23:
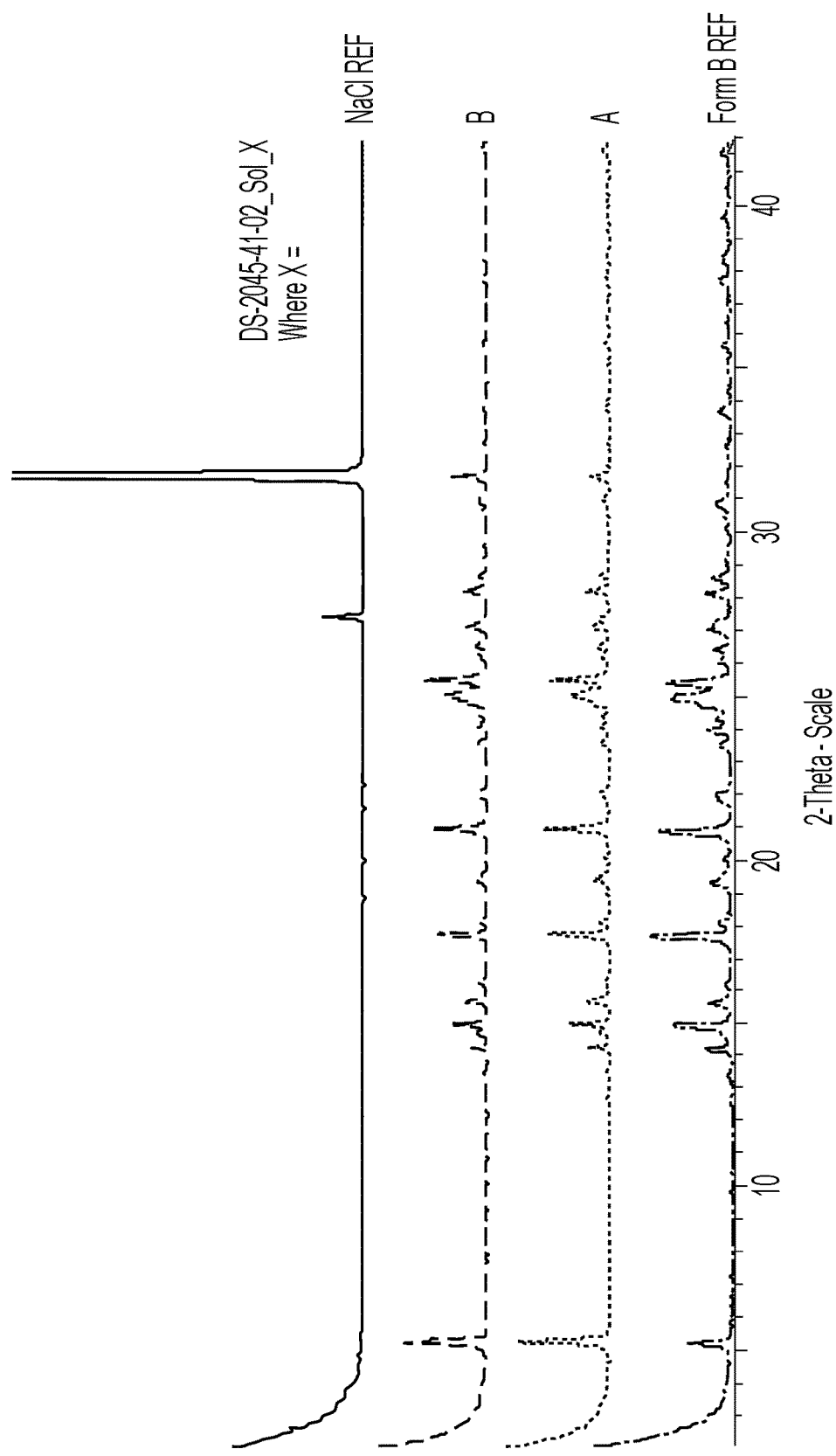
FIG. 23 shows an XRPD of PP-001 Form B after thermodynamic solubility determination.

The results from competitive slurrying of Form A and Form B are shown in FIGS. 21-23, and summarized in FIG. 24.

As can be seen from FIG. 24, Form A was obtained in all solvents and temperature tested. The results would suggest that Form A is therefore the preferred form under the investigated solvents system and temperature range. It was noted that IPA and IPA/water mixtures at high temperature showed some solvent evaporation, giving clear solutions with solid present on the side of the vial above the solvent line. To confirm no false positive result may be present, additional solid form mixture (Form A+Form B) was added to these samples, which were left to mature for an additional 24 hours. In each case a sustained suspension was observed 24 hours after addition of more solid mixture. An aliquot was taken for analysis (DS-2045-48-XX-B, total time 5 days). XRPD confirmed presence of only Form A.

In addition to the competitive slurrying, Form A and Form B were both submitted to thermodynamic solubility measurements in FaSSIF media, as well as IDR in pH 7.4 phosphate buffer. The results are shown in Table 19 The full reports for both measurements can be found in Appendix 2—Analytical Service Reports.

TABLE 19

Thermodynamic stability and Intrinsic Dissolution Rate (IDR) of Form A and Form B.

| Identity | Form A, Anhydrous | Form B, Anhydrous |
|---|---|---|
| Thermodynamic solubility (TS) in FaSSIF | 0.76 mg/ml | 0.93 mg/ml |
| XRPD post-TS | Unchanged, residual NaCl from media detected | Unchanged, residual NaCl from media detected |
| Dissolution rate (pH 7.4 buffer) | 0.071 mg/min/cm$^2$ | 0.15 mg/min/cm$^2$ |
| XRPD post-IDR | Unchanged | Unchanged |

The results from Table 19 show that both forms have very low aqueous solubility (<1 mg/ml) with a slow dissolution rate (<0.1 g/min·cm2). In thermodynamic solubility measurements and IDR measurements, Form A displayed the lower solubility and slower dissolution rate compared to Form B. The results are in agreement with the competitive slurrying measurements which suggest that Form A is the thermodynamically more stable form.

Figure 25:
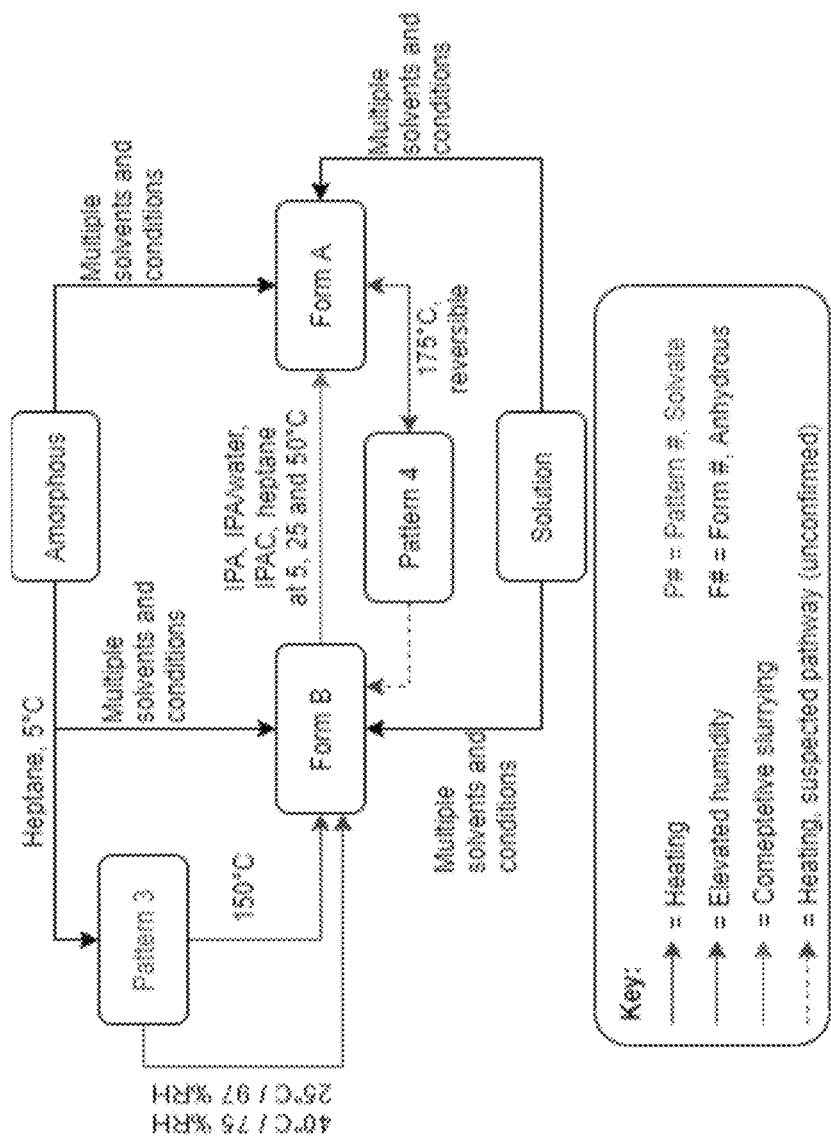
FIG. 25 shows a diagram showing the different polymorphic forms of PP-001.

A form diagram based on the experiments described herein is shown in FIG. 25. Full characterization was completed on Form B and Pattern 3, which were both successfully scaled up. Analysis indicates that Form B is a non-solvated anhydrous form, suitable for thermodynamic stability studies with Form A. Pattern 3 was found to be a non-stoichiometric heptane solvate, which is unstable and transitions to Form B. FIG. 16 shows that most solvents and conditions result in the crystallization of either Form B or Form A. The only exception is maturation of amorphous material in heptane at 5° C., which results in Pattern 3. Characterization of Pattern 3 showed the solvate to be unstable and will transition to Form B under elevated humidity or by heating/drying.

Both Form A and Form B are stable, anhydrous forms of PP-001, however, competitive slurrying of Form A and Form B revealed that Form A is the preferred form over all conditions and solvents tested. Therefore, Form A is likely to be the most thermodynamically favorable and the form recommended for further scale-up. The results from the competitive slurrying were consistent with the results from the thermodynamic solubility and IDR measurements, where Form A showed the lower solubility compared to Form B, suggesting that Form A is the more stable form.

Finally, an additional high temperature form (Pattern 4) accessed by heating Form A above 175° C. was observed. The transition from Form A to Pattern 4 is reversible, with Pattern 4 only visible at elevated temperatures. Based on the thermal data gathered on Form A and Form B, it is theorized that the transition from Form A to Pattern 4 is followed by a transition from Pattern 4 to Form B on heating up to the sample melt. However, direct measurements of this transition could not be observed due to the closeness of the thermal event to the melting point. Pattern 4 is unlikely to be the form of concern in terms of crystallization process development, due to the high temperatures required to access Pattern 4.

Example 7—Crystallization Development on PP-001 Form A

PP-001 Form A was selected for crystallization development as it was found to be the most thermodynamically stable form.

The strategy for crystallization development was to select Class III crystallization solvents from the previously performed solubility assessment (Example 1). Solubility curves of Form A in these solvent/antisolvents mixtures were then obtained and the data regressed using DynoChem to generate solubility models of Form a as a function of both solvent composition and temperature.

Small (1 g) scale crystallizations were then subsequently performed based on the solubility models generated to assess the validity of the models, and the crystallization kinetics of Form A in the solvent mixtures. Finally, the optimum process performed on 1 g scale was scaled-up to 5 g scale and monitored with PAT (process-analytical technology) to assess the robustness of process on multigram scale with overhead stirring.

Method 1. PP-001 Form A 1 g was dispensed into a 20 ml scintillation vial. To this, a stirrer bar was added and 11.2 vol IPA (11.2 ml) and 1.2 vol H$_2$O (1.2 ml) were charged. The resulting suspension was heated to 65° C. using a Polar Bear (Cambridge Reactor Designs heat/cool block) with 500 rpm magnetic stirring to give a clear solution.

The solution was cooled to 58° C. (Ssat ratio 1.2), and 5 wt % PP-001 Form A seeds (5 wt %, 50 mg) were added. The seeds were observed to sustain, and the suspension was stirred for 1 hour.

The suspension was then cooled to 5° C. at a rate of 0.1° C./min, then held isothermally overnight.

The suspension was then isolated by filtration, dried under suction for 30 minutes, and the solid transferred to a vacuum oven for drying overnight at RT.

Method 2. PP-001 Form A 1 g was dispensed into a 20 ml scintillation vial. To this, a stirrer bar was added and 11.2 vol IPA (11.2 ml) and 1.2 vol H$_2$O (1.2 ml) were charged. The resulting suspension was heated to 65° C. using a Polar Bear (Cambridge Reactor Designs heat/cool block) with 500 rpm magnetic stirring to give a clear solution.

The solution was cooled to 58° C. (Ssat ratio 1.2), and 5 wt % PP-001 Form A seeds (5 wt %, 50 mg) were added. The seeds were observed to sustain, and the suspension was stirred for 1 hour. 7 vol H$_2$O (7 ml) was then charged by syringe pump over two hours. The suspension was then cooled to 5° C. at a rate of 0.1° C./min, then held isothermally overnight.

The suspension was then isolated by filtration, dried under suction for 30 minutes, and the solid transferred to a vacuum oven for drying overnight at RT.

Method 3. PP-001 Form A 1 g was dispensed into a 20 ml scintillation vial. To this, a stirrer bar was added and 6.4 vol acetone (6.4 ml) and 0.6 vol H$_2$O (0.6 ml) were charged. The resulting suspension was heated to 40° C. using a Polar Bear (Cambridge Reactor Designs heat/cool block) with 500 rpm magnetic stirring to give a clear solution.

The solution was cooled to 30° C. (Ssat ratio 1.2), and 5 wt % PP-001 Form A seeds (5 wt %, 50 mg) were added. The seeds were observed to sustain, and the suspension was stirred for 1 hour. 3 vol H$_2$O (3 ml) was then charged by syringe pump over two hours. The suspension was then cooled to 5° C. at a rate of 0.1° C./min, then held isothermally overnight.

The suspension was then isolated by filtration, dried under suction for 30 minutes, and the solid transferred to a vacuum oven for drying overnight at RT.

Method 4. PP-001 Form A 1 g was dispensed into a 20 ml scintillation vial. To this, a stirrer bar was added and 4.2 vol acetone (4.2 ml) and 0.33 vol H$_2$O (0.33 ml) were charged. The resulting suspension was heated to 50° C. using a Polar Bear (Cambridge Reactor Designs heat/cool block) with 500 rpm magnetic stirring to give a clear solution.

The solution was cooled to 40° C. (Ssat ratio 1.2), and 5 wt % PP-001 Form A seeds (5 wt %, 50 mg) were added. The seeds were observed to sustain, and the suspension was stirred for 1 hour. 3 vol H$_2$O (3 ml) was then charged by syringe pump over two hours. The suspension was then cooled to 5° C. at a rate of 0.1° C./min, then held isothermally overnight.

The suspension was then isolated by filtration, dried under suction for 30 minutes, and the solid transferred to a vacuum oven for drying overnight at RT.

Results. The results of characterization of the solids isolated from the 1 g scale experiments are shown in Table 20. In all four protocols performed dissolution of PP-001 Form A was observed at the dissolution temperature identified using the DynoChem model, and the seed was observed to sustain at the seeding temperature. These observations indicate the accuracy of the solubility models generated. In all four of the experiments performed phase pure Form A was obtained in high purity (99.8% by HPLC) and low residual solvent content (as demonstrated by 4 H-NMR). The material was obtained in varying yield with process 2 (IPA/water) giving the highest recovery (88.7%). Based on the solubility models generated yields in excess of 90% were theoretically possible for each of the processes. The difference in obtained and predicted yield can be explained by the rate of crystal growth of Form A in the solvent mixtures, in all instances the solution was still supersaturated at the point of solid isolation, indicating that the growth kinetics are slow.

TABLE 20

Results of 1 g scale-up experiments

| | Sample ID | | | |
|---|---|---|---|---|
| | JH-2045-62-01 | JH-2045-62-02 | JH-2045-62-03 | JH-2045-62-04 |
| Process solvents | IPA/H$_2$O | IPA/H$_2$O | Acetone/H$_2$O | Acetone/H$_2$O |
| Total volumes | 12.4 | 19.4 | 10 | 7.53 |
| XRPD | Form A | Form A | Form A | Form A |
| $^1$H-NMR | Consistent with structure. 0.003 mol. eq. IPA | Consistent with structure. 0.002 mol. eq. IPA | Consistent with structure. 0.002 mol. eq. acetone | Consistent with structure. 0.002 mol. eq. acetone |
| PLM | Plates ca. 10 μm diameter | Plates ca. 10 μm diameter | Plates ca. 10 μm diameter | Plates ca. 10 μm diameter |
| HPLC | 99.8% | 99.8% | 99.8% | 99.8% |
| Recovery/Yield | 880 mg/ 84.8% | 940 mg/ 88.7% | 878 mg/ 83.0% | 881 mg/ 83.2% |

Figure 26:
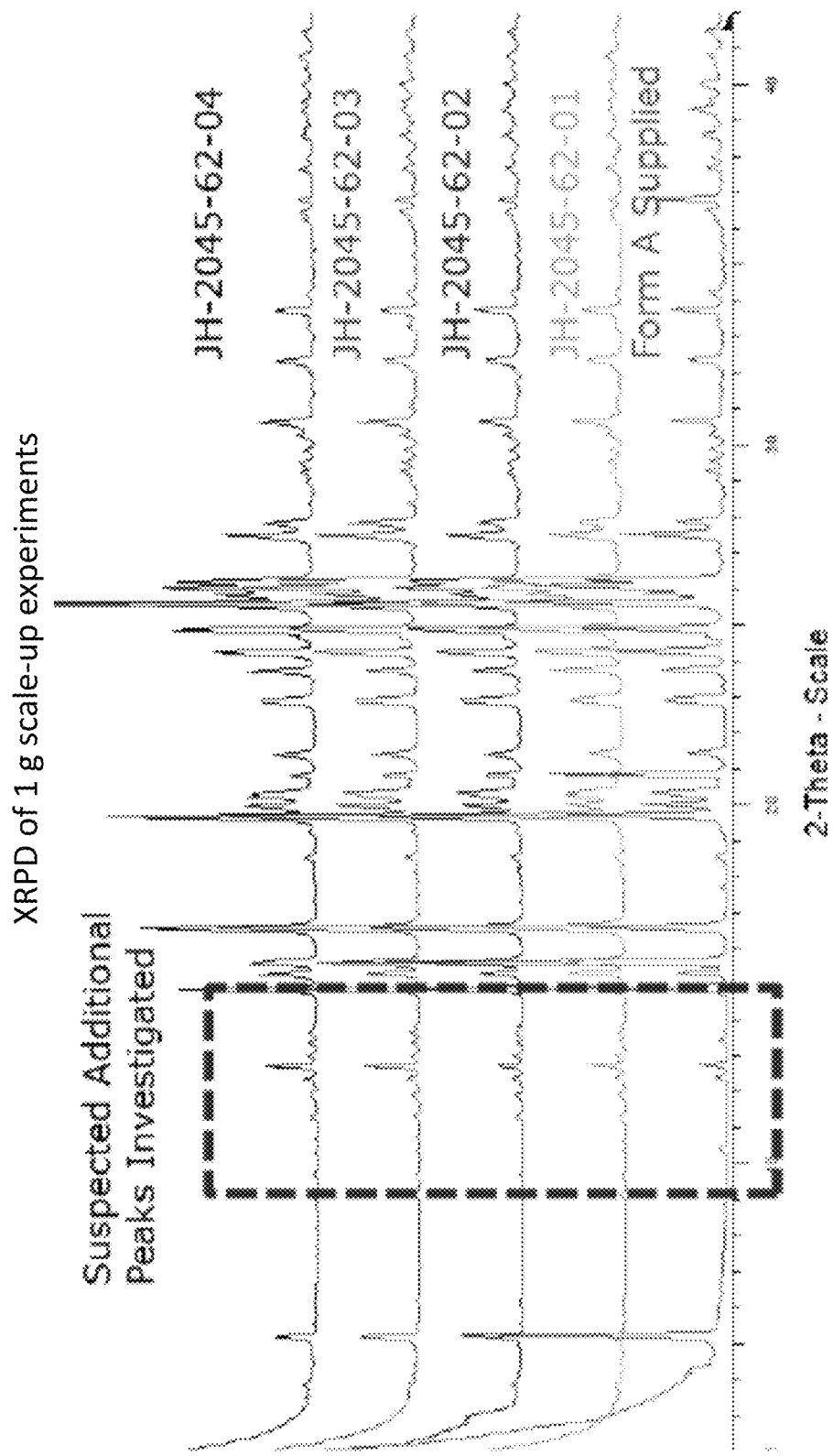
FIG. 26 shows XRPD analysis of the 1 g crystallization scale-up of PP-001 Form A.
Figure 27:
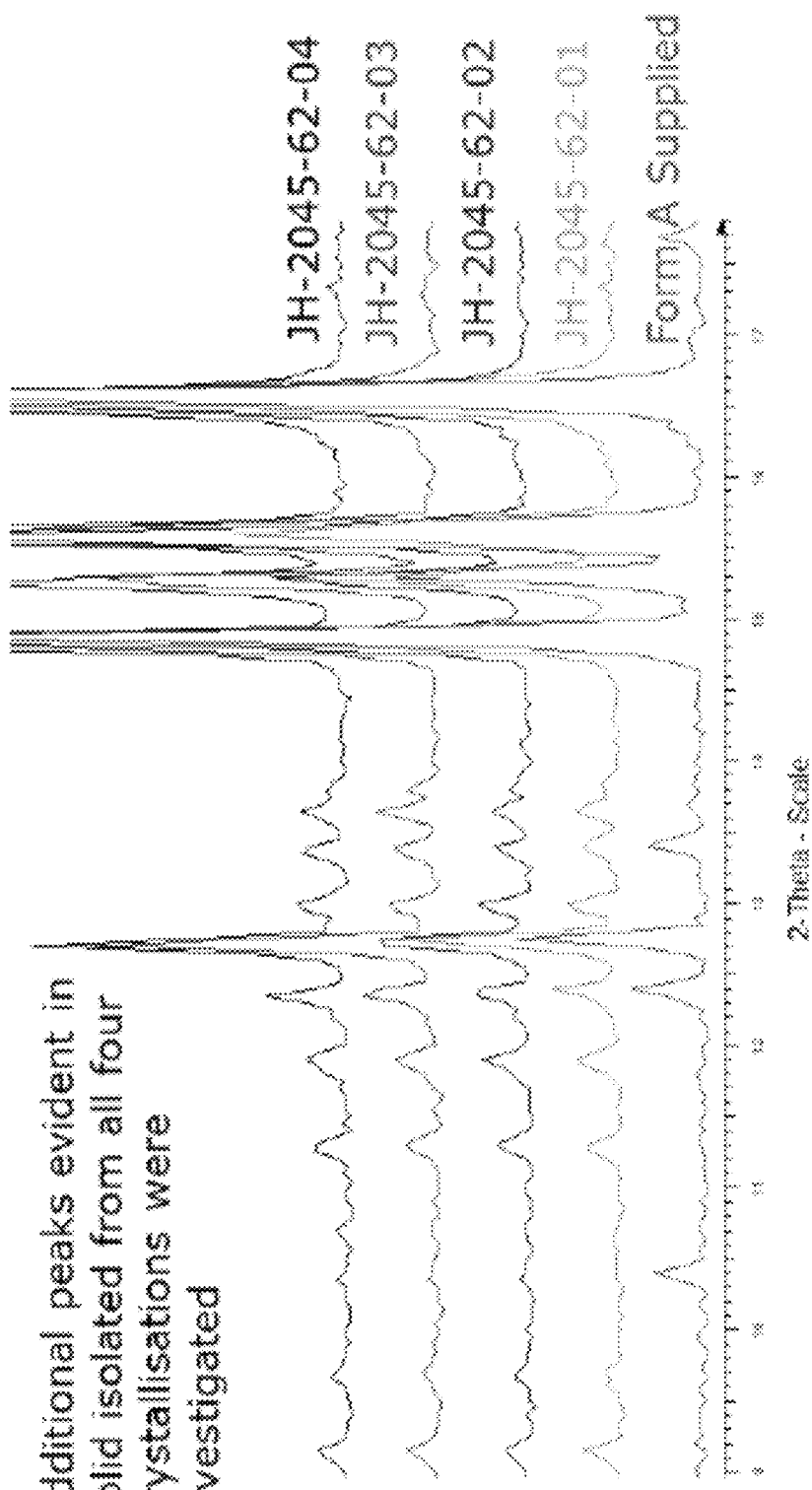
FIG. 27 shows a comparison of XRPD profiles of supplied PP-001 Form A, and PP-001 Form A crystalized using 4 crystallization methods.
Figure 29:
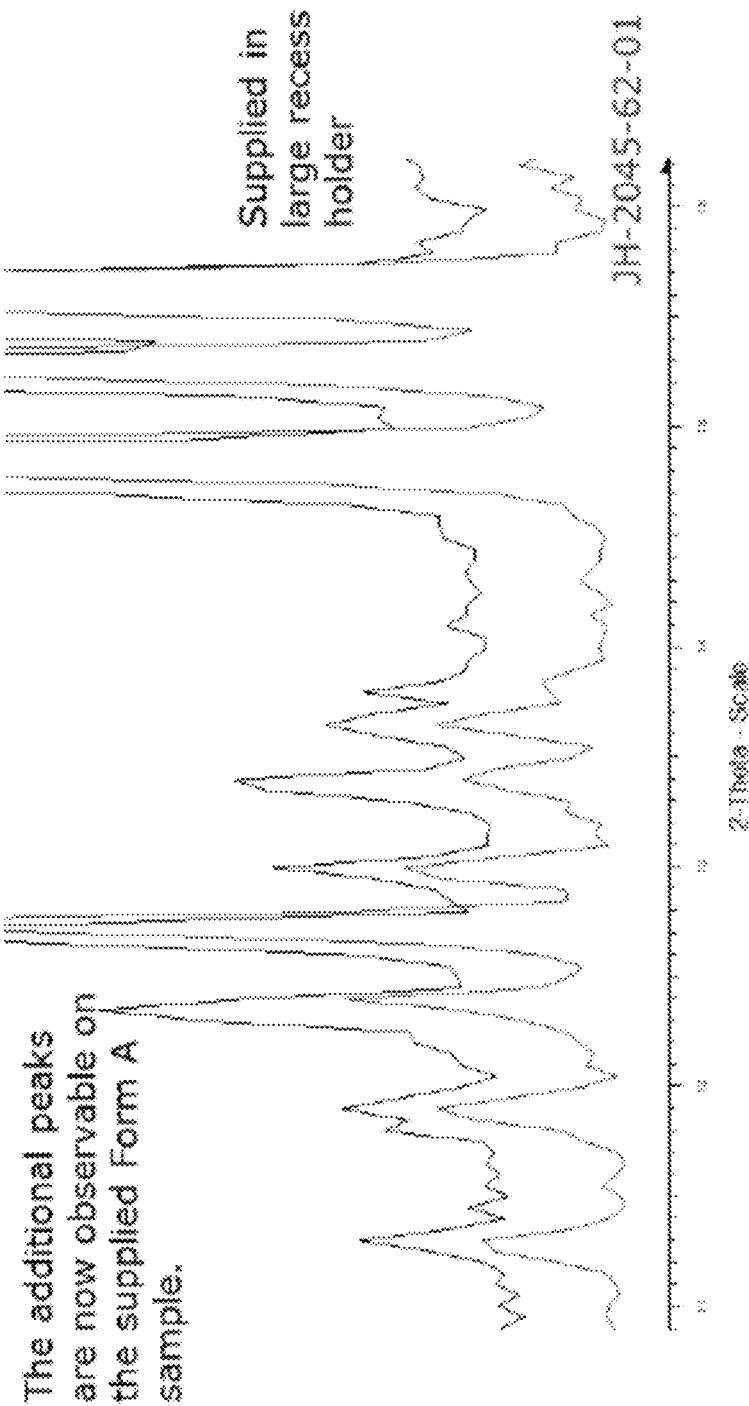
FIG. 29 shows the XRPD profiles of PP-001 Form A crystallized using a large-recess sample holder.
Figure 30:
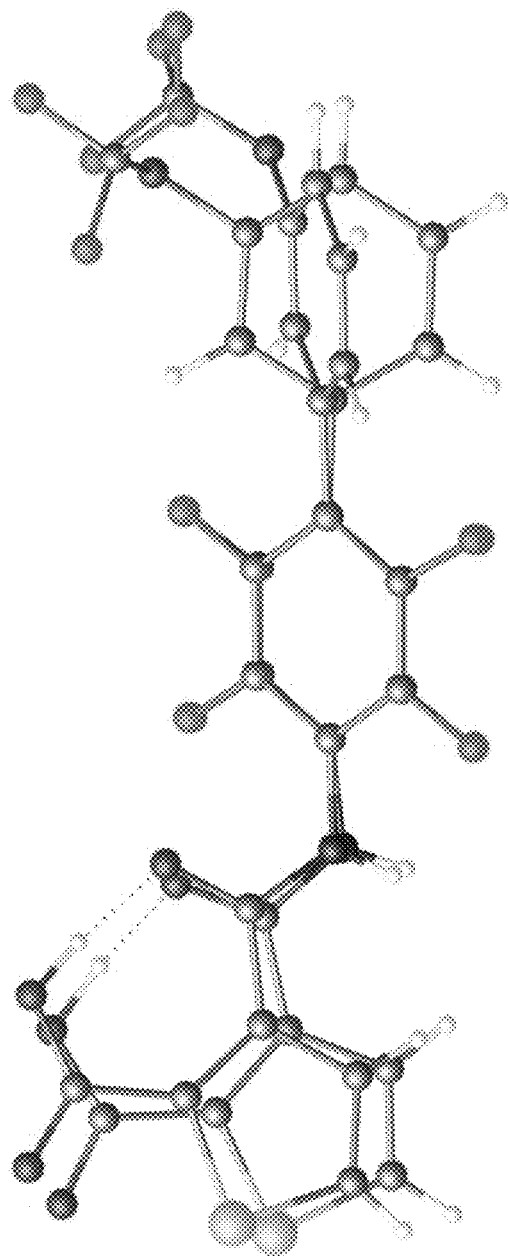
FIG. 30 shows an overlay of the crystal structures of Forms A and B.

In the XRPD pattern of each of the four solids isolated from the 1 g experiments additional peaks were observed in the 2q range 11-14' when compared to the supplied Form A (FIG. 26 and FIG. 27). These peaks are consistent between the samples and of low magnitude. Examination of the PLM of the supplied sample of Form A demonstrates it to be composed of large plates ca. 100 μm in diameter (FIG. 28). The particles obtained from the scale-ups were however composed of much smaller particles ca. 10 μm in diameter. When samples are prepared for XRPD measurements they are pressed flat onto the sample holder. The geometry of large plates (such as those in the supplied material) means that when pressed flat they typically lie with their largest face parallel to the sample holder. This means that some planes of the crystal are presented at lower frequency to the incoming X-rays than others resulting in a lower number of peaks evident in the XRPD pattern, an effect called preferred orientation. The orientation of smaller plates (such as those in samples (JH-2045-62-04) are more likely to be randomly distributed during sample preparation presenting more crystal planes to the incoming X-rays resulting in an XRPD pattern with a larger number of peaks. To assess whether the additional peaks observed in the XRPD patterns of the 1 g scale-up samples resulted from preferred orientation a sample of the supplied material was remeasured using a larger sample holder. Use of a larger sample holder allows for the crystals to be positioned in more orientations and therefore a greater number of reflections to be measured. The XRPD pattern of the supplied material measured using a large holder is shown in FIG. 29. The XRPD pattern displays the additional peaks seen from the 1 g scale-up samples demonstrating that these reflections are present in crystals of Form A.

What is claimed is:

1. A polymorph of 3-(2,3,5,6-tetrafluoro-3'-trifluoromethoxy-biphenyl-4-ylcarbamoyl)-thiophene-2-carboxylic acid as shown in Formula I:

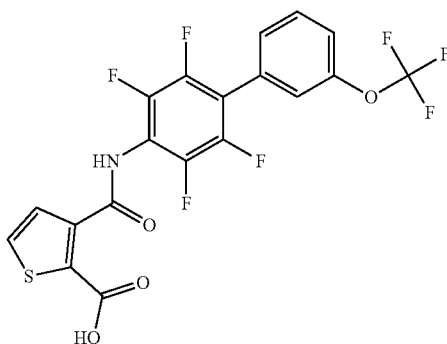

Formula I wherein the polymorph is

Form A comprising an X-ray powder diffraction (XRPD) comprising three or more 2θ values selected from 14.8±0.2, 15.6±0.2, 16.5±0.2, 19.6±0.2, 20.8±0.2, 25.6±0.2 and 26.1±0.2; or Form B comprising an X-ray powder diffraction (XRPD) comprising three or more 2θ values selected from 14.9±0.2, 17.6±0.2, 19.3±0.2, 20.9±0.2, 24.0±0.2, 24.9±0.2 and 25.4±0.2.

2. The polymorph of claim 1, wherein the polymorph is Form A.

3. The polymorph of claim 2, wherein the polymorph comprises four or more 2θ values selected from 14.8±0.2, 15.6±0.2, 16.5±0.2, 19.6±0.2, 20.8±0.2, 25.6±0.2 and 26.1±0.2.

4. The polymorph of claim 2, wherein Form A comprises the XRPD pattern shown in FIG. 2A.

5. The polymorph of claim 2 further comprising one or more characteristics selected from:
a. a DSC spectrum (5° C./min) comprising an endotherm onset at 178.3±1.0° C., and a second endotherm onset at 227.3=1.0° C.;
b. a DSC spectrum (10° C./min) comprising an endotherm onset at 177.6±1.0° C., and an endotherm onset at 227.9±1.0° C.;
c. a DSC spectrum (20° C./min) comprising an endotherm onset at 178.5±1.0° C., and an endotherm onset at 222.5±1.0° C. and 224.3±1.0° C., followed by an endotherm onset at 227.8±1.0° C.;
d. a DSC spectrum (50° C./min) comprising double endotherm onsets at 88.0±1.0° C. and 92.6±1.0° C., a second endotherm onset at 180.5±1.0° C., a sharp endo/exo onset at 224.7±1.0° C., and an endotherm onset at 229.5±1.0° C.;
e. a melt-quench-cool (MDSC) comprising an endotherm onset at 177.7±1.0° C., an endotherm onset at 227.8±1.0° C.; or
f. a VT-XRPD pattern with observable changes at 200° C.

6. The polymorph of claim 1, wherein the polymorph is Form B.

7. The polymorph of claim 6, wherein the polymorph comprises four or more 2θ values selected from 14.8±0.2, 17.6±0.2, 19.3±0.2, 20.9±0.2, 24.0±0.2, 24.9±0.2 and 25.4±0.2.

8. The polymorph of claim 6, wherein Form B comprises the XRPD pattern shown in FIG. 2B.

9. A pharmaceutical composition comprising the polymorph Form A or Form B of claim 1.

10. A kit comprising the polymorph Form A or Form B of claim 1.

11. A method of preparing polymorph Form A of 3-(2,3,5,6-tetrafluoro-3'-trifluoromethoxy-biphenyl-4-ylcarbamoyl)-thiophene-2-carboxylic acid, the method comprising:
a) obtaining a sample comprising 3-(2,3,5,6-tetrafluoro-3'-trifluoromethoxy-biphenyl-4-ylcarbamoyl)-thiophene-2-carboxylic acid;
b) dissolving the sample of (a) in a solvent comprising $C_1$-$C_5$ alcohol, $C_1$-$C_5$ ketone, or $C_1$-$C_5$ acetate solvent at 20° C. to 60° C. to form a solution; and
c) removing the solvent from the solution to obtain the polymorph Form A of claim 1.

12. The method of claim 11, wherein the $C_1$-$C_5$ alcohol is selected from methanol, ethanol, 1-propanol, isopropanol, 1-butanol, 2-butanol, 1-pentanol, 2-pentanol, or isopentanol, the $C_1$-$C_5$ ketone is selected from methyl ethyl ketone (MEK), methylisobutyl ketone (MIBK), or acetone, and the $C_1$-$C_5$ acetate is selected from methyl acetate, ethyl acetate, propyl acetate, butyl acetate, or pentyl acetate.

13. The method of claim 11, wherein the solution is greater than 80% $C_1$-$C_5$ alcohol, $C_1$-$C_5$ ketone, or $C_1$-$C_5$ acetate.

14. The method of claim 11, wherein the solution comprises 0% to 20% water.

15. The method of claim 11, wherein after the dissolving in (b), the solution is cooled to an incubation temperature of 1° C. to 10° C. for a period of time.

16. The method of claim 15, wherein the cooling to the incubation temperature is at a rate of about 0.02° C./min to about 1° C./min until the incubation temperature is reached.

17. The method of claim 15, wherein the period of time for the incubation temperature is about 1 hour to about 48 hours.

18. The method of claim 11, wherein the removing of the solvent is performed by evaporation or filtration.

19. The method of claim 18, wherein the evaporation occurs at about 20° C. to about 35° C.

20. A method of treating or ameliorating a disease or condition in a subject in need thereof comprising administering to the subject a pharmaceutically effective amount of polymorph Form A of claim 1, wherein the disease or condition is an inflammatory disease or disorder.

* * * * *

UNITED STATES PATENT AND TRADEMARK OFFICE
CERTIFICATE OF CORRECTION

PATENT NO. : 12,209,073 B2
APPLICATION NO. : 18/172656
DATED : January 28, 2025
INVENTOR(S) : Stefan Sperl et al.

It is certified that error appears in the above-identified patent and that said Letters Patent is hereby corrected as shown below:

In the Specification

Column 8, Line 27, delete "FIG. 2A One" and insert -- FIG. 2A. One --.

Column 8, Line 44, delete "or 0.1° C." and insert -- or ±0.1° C. --.

Column 19, Line 44 (approx.), delete "and IPLC characteristics" and insert -- and HPLC characteristics --.

Column 21, Line 10-11, delete "or 50° C. to 60° C." and insert -- 50° C., or 60° C." --.

Column 21, Line 13, delete "to 5° C.," and insert -- to 50° C., --.

Column 21, Line 14, delete "50° C. 60° C." and insert -- 50° C. to 60° C. --.

Column 23, Line 58, delete "pulmonary sarcosis, bone" and insert -- pulmonary sarcoidosis, bone --.

Column 27, Line 15, delete "vol (450 l) at" and insert -- vol (450 µl) at --.

Column 28, Line 8, delete "by XRPD" and insert -- by XRPD. --.

Column 30, Line 55, delete "a 20 scan" and insert -- a 2θ scan --.

Column 31, Line 10, delete "vol (1600 l) of" and insert -- vol (1600 µl) of --.

Column 32, Line 14 (approx.), delete "water (30%) for" and insert -- water (3%) for --.

Signed and Sealed this
Thirtieth Day of December, 2025

John A. Squires
*Director of the United States Patent and Trademark Office*

CERTIFICATE OF CORRECTION (continued)
U.S. Pat. No. 12,209,073 B2

Column 32, Line 16-17, delete "ketone, methyisobutyl ketone," and insert -- ketone, methylisobutyl ketone, --.

Column 33, Line 18 (approx.), delete "Microscopy (SEAM). For" and insert -- Microscopy (SEM). For --.

Column 33, Line 31, delete "and 111B, respectively)" and insert -- and 11B, respectively) --.

Column 35-36, Line 18 (TABLE 14), delete "small peaket 17.6" and insert -- small peak at 17.6 --.

Column 36, Line 19-20, delete "Stimulated" and insert -- Simulated --.

Column 37, Line 67, delete "(FIGS. 15A-15B)" and insert -- (FIGS. 15A-15B). --.

Column 43, Line 44-45, delete "by 4 H-NMR)." and insert -- by 1H-NMR). --.

Column 44, Line 26 (approx.), delete "11-14' when" and insert -- 11-14° when --.

In the Claims

Column 45, Claim 5, Line 38, delete "227.3=1.0° C.;" and insert -- 227.3±1.0° C.; --.